(12) United States Patent
Seidah et al.

(10) Patent No.: US 9,879,093 B2
(45) Date of Patent: Jan. 30, 2018

(54) SINGLE DOMAIN ANTIBODIES AS INHIBITORS OF PCSK9

(71) Applicants: ADAERATA, LIMITED PARTNERSHIP, Montreal (CA); NATIONAL RESEARCH COUNCIL CANADA, Ottawa (CA)

(72) Inventors: Nabil G. Seidah, Verdun (CA); Jianbing Zhang, Ottawa (CA)

(73) Assignees: ADAERATA, LIMITED PARTNERSHP, Montreal (CA); NATIONAL RESEARCH COUNCIL OF CANADA, Ottawa (CA)

(*) Notice: Subject to any disclaimer, the term of this patent is extended or adjusted under 35 U.S.C. 154(b) by 806 days.

(21) Appl. No.: 14/366,345

(22) PCT Filed: Dec. 20, 2012

(86) PCT No.: PCT/CA2012/050923
§ 371 (c)(1),
(2) Date: Jun. 18, 2014

(87) PCT Pub. No.: WO2013/091103
PCT Pub. Date: Jun. 27, 2013

(65) Prior Publication Data
US 2015/0017183 A1    Jan. 15, 2015

Related U.S. Application Data

(60) Provisional application No. 61/578,000, filed on Dec. 20, 2011.

(51) Int. Cl.
*C07K 16/40* (2006.01)
*G01N 33/573* (2006.01)

(52) U.S. Cl.
CPC ......... *C07K 16/40* (2013.01); *G01N 33/5735* (2013.01); *C07K 2317/22* (2013.01); *C07K 2317/565* (2013.01); *C07K 2317/567* (2013.01); *C07K 2317/569* (2013.01); *C07K 2317/76* (2013.01); *C07K 2317/77* (2013.01); *C07K 2317/92* (2013.01); *G01N 2333/96433* (2013.01)

(58) Field of Classification Search
None
See application file for complete search history.

(56) References Cited

U.S. PATENT DOCUMENTS 5,631,169 A    5/1997    Lakowicz et al.

FOREIGN PATENT DOCUMENTS

| WO | WO2003/046560 | 6/2003 |
|---|---|---|
| WO | 2008063382 | 5/2008 |
| WO | WO2008057457 A2 | 5/2008 |
| WO | WO2008057459 A2 | 5/2008 |
| WO | WO2008125623 A2 | 10/2008 |
| WO | WO2009/055783 | 4/2009 |
| WO | WO2010/029513 | 3/2010 |
| WO | WO2011/020183 A1 | 2/2011 |
| WO | 2011072263 | 6/2011 |

OTHER PUBLICATIONS

Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Muyldermans S., 2001. Single domain camel antibodies: current statusReviews in Molecular Biotechnology, 74: 277-302.
Reason for Rejection dated Sep. 20, 2016 in Japanese Application No. 2014-547652 to Seidah et al.
Communication pursuant to Article 94(3) of the EPC dated Jun. 1, 2016 in European Application No. 12859390.2 to Seidah et al.
Office Action dated Oct. 17, 2016 in Chinese Application No. 201280070110 to Seidah et al.
Office Action dated Dec. 16, 2015 in Chinese Application No. 201280070110 to Seidah et al.
Abhinandan, et al., "Analysis and improvements to Kabat and structurally correct numbering of antibody variable domains", Molecular Immunology, 45, 3832-3839, (2008).
Abifadel et al., "Mutations in PCSK9 cause autosomal dominant hypercholesterolemia", Nat. Genetics 34:154-156, (2003).
Baldi et al., Recombinant protein production by large-scale transient gene expression in mammalian cells: state of the art and future perspectives, Biotechnology Letters, 29(5):677-684, (2007).
Bell et al., Differential tumor-targeting abilities of three single-domain antibody formats, Cancer Letters 289:81-90, (2010).
Benjannet et al, "Zymogen Cleavage and Effects on the Low Density Lipoprotein (LDL) Receptor and LDL Cholesterol", J. Biol. Chem. 279 : 48865-48875, (2004).
Benjannet et al., "Effects of the Prosegment and pH on the Activity of PCSK9, Evidence for additional processing events", J Biol Chem. 285 :40965-40978, (2010).
Berge et al., "Pharmaceutical Salts", J. Pharm. Sci. 66 :1-19, (1977).
Berntzen et al., Prolonged and increased expression of soluble Fc receptors, IgG and a TCR-Ig fusion protein by transiently transfected adherent 293E cells, Journal of Immunological Methods, 298 (1-2): 93-104, (2005).

(Continued)

*Primary Examiner* — Sharon Wen
(74) *Attorney, Agent, or Firm* — Julie Gauvreau

(57) ABSTRACT

Antibodies (e.g., sdAbs) binding to PCSK9 are described. Nucleic acids encoding such Abs, host cells expressing such Abs and pharmaceutical composition comprising same are described. The use of these PCSK9-binding Abs for lowering low-density lipoprotein-cholesterol (LDL-C) levels and for the treatment of cardiovascular disorders, is also described.

22 Claims, 36 Drawing Sheets

(56) References Cited

OTHER PUBLICATIONS

Briel et al., "Statin therapy for prevention and treatment of acute and chronic cardiovascular disease: update on recent trials and metaanalyses", Curr. Opi. Lipidol., 16: 601-605, (2005).
Brown et al., "Lowering LDL—Not Only How Low, But How Long?", Science, 311: 1721-1723, (2006).
Cameron et al, "Effect of mutations in the PCSK9 gene on the cell surface LDL receptors", Human Mol. Genet. 15:1551-1558, (2006).
Cohen et al., "Sequence Variations in PCSK9, Low LDL, and Protection against Coronary Heart Disease" N. Engl. J. Med. 354 :1264-1272, (2006).
De Kruif et al., "Leucine Zipper Dimerized Bivalent and Bispecific scFv Antibodies from a Semi-synthetic Antibody Phage Display Library", J Biol Chem, 271, 7630-7634 (1996).
Dubuc et al., "Statins Upregulate PCSK9, the Gene Encoding the Proprotein Convertase Neural Apoptosis-Regulated Convertase-I Implicated in Familial Hyperchoesterolemia" , Artheroscler thromb Vasc Biol. 24:1454-1459, (2004).
Dubuc et al., "A new method for measurement of total plasma PCSK9: clinical applications", J. Lipid Res. 51 :140-149, (2010).
Durocher et al., "High-level and high-throughput recombinant protein production by transient transfection of suspension-growing human 293-EBNA1 cells", Nucleic Acids Research, 30(2):E9, (2002).
Herbert et al., "Increased Secretion of Lipoproteins in Transgggenic Mice Expressing Human D374Y PCSK9 Under Physiological Genetic Control", Artheriosclerosis, Thrombosis, and Vascular Biology, 30(7) :1333-1339,(2010).
Johnson et al. "NCBI Blast: a better web interface", Nucleic acids Res. 36:W5-W9, (2008).
Lakoski et al, "Genetic and Metabolic Determinants of Plasma PCSK9 Levels", The Journal of Clinical Endocrinology and metabolism, 94(7): 2537-2543, (2009).
Law et al., "Quantifying effect of statins on low density lipoprotein cholesterol, ischaemic heart disease, and stroke: systematic review and meta-analysis", BMJ 326 :1423-1427, (2003).
Leren, T.P., "Mutations in the PCSK9 gene in Norwegian subjects with autosomal dominant hypercholesterolemia", Clin. Genet. 65:419-422, (2004).
Maxwell et al., "Novel putative SREBP and LXR target genes identified by microarray analysis in liver of cholesterol-fed mice", J Lipid Res. 44 :2109-2119, (2003).
Maxwell et al., "Adenoviral-mediated expression of Pcsk9 in mice results in a low-density lipoprotein receptor knockout phenotype", Proc. Natl. Acad. Sci USA 101:7100-7105, (2004).
Miller A. D. , "Progress Toward Human Gene Theraty", Blood 76 :271-278, (1990).
Nielsen et al., "Targeting of Bivalent Anti-ErbB2 Diabody Antibody Fragments to Tumor Cells Is Independent of the Intrinsic Antibody Affinity", Cancer Research 60, 6434-6440 (2000).
Papadopoulos et al., "Cobalt: constraint-based alignment tool for multiple protein sequences", Bioinformatics 23:1073-1079, (2007).
Poirier et al., Dissection of the Endogenous Cellular Pathways of PCSK9-induced Low Density Lipoprotein Receptor Degradation, J. Biol. Chem. 284 :28856-28864, (2009).
Ranade, V.V., Drug Delivery Systems. 1. Site-Specific Drug Delivery Using Liposomes as Carriers, J. Clin. Pharmacol. 29 : 685-694, (1989).
Rashid et al., "Decreased plasma cholesterol and hypersensitivity to statins in mice lacking Pcsk9", Proc. Natl. Acad. Sci. 102(15) : 5374-5379, (2005).
Ridgway et al, "Knobs-into-holes" engineering of antibody CH3 domains for heavy chain heerodimerization, Protein Eng 9, 617-621 (1996).
Riechmann et al., "Single domain antibodies: comparison of camel VH and camelised human VH domains", J. Immunol. Methods, 231 (1-2):25-38, (1999 ).
Seidah et al., "The secretory proprotein convertase neural apoptosis-regulated convertase 1 (NARC-1): Liver regeneration and neuronal differentiation", Proc. Natl. Acad. Sci. USA 100:928-933, (2003).
Stephan et al. , "Rapid fluorometric assay of LDL receptor activity by DiI-labeled LDL", J. Lipid res. 34:325-330, (1993).
Tall A.R. N. "Protease Variants, LDL' and Coronary Heart Disease", Engl. J. Med., 354:1310-1312, (2006).
Timms et al., "A mutation in PCSK9 causing autosomal-dominant hypercholesterolemia in a Utah pedigree", Hum. Genetics 114:349-353, (2004).
Wesolowski et al., "Single domain antibodies: promising experimental and therapeutic tools in infection and immunity", Med. Microbiol. Immunol., 198(3): 157-174, (2009).
Wurm, et al., "Large-scale transient expression in mammalian cells for recombinant protein production" Current Opinion in Biotechnology, 10(2): 156-159, (1999).
Zaid et al., "Proprotein Convertase Subtilisin/Kexin Type 9 (PCSK9)': Hepatocyte-Specific Low-Density Lipoprotein Receptor Degradation and Critical Role in Mouse Liver Regeneration" Hepatology, 48 (2): 646-654, (2008).
Zhang et al., "A Pentavalent Single-domain Antibody Approach to Tumor Antigen Discovery and the Development of Novel Proteomics Reagents", J. Mol. 341, 161-169 (2004).
Zhang et al., "Pentamerization of Single-domain Antibodies from Phage Libraries: A Novel Strategy for the Rapid Generation of High-avidity Antobody Reagents", J. et al J. Mol. 335, 49-56 (2004).
International Search Report and Written Opinion dated Feb. 20, 2013 in PCT/CA2012/050923 to Seidah, Nabil G.
Supplementary European Search Report and Written Opinion dated Aug. 28, 2015 in EP12859390.2 to Seidah, Nabil G.

* cited by examiner

```
                                                         V5
PKE2   MGTVSSRRSWWPLPLLLLLLLLLGPAGARAQEDGKPIPNPLLGLDSTQVKLEESGGGLVQ 60
PKF8   MGTVSSRRSWWPLPLLLLLLLLLGPAGARAQEDGKPIPNPLLGLDSTQVQLVESGGGLVQ 60
PKF1   MGTVSSRRSWWPLPLLLLLLLLLGPAGARAQEDGKPIPNPLLGLDSTQVKLEESGGGLVQ 60
PKG1   MGTVSSRRSWWPLPLLLLLLLLLGPAGARAQEDGKPIPNPLLGLDSTQVQLVESGGGLVQ 60
P1.70  MGTVSSRRSWWPLPLLLLLLLLLGPAGARAQEDGKPIPNPLLGLDSTQVQLVESGGGLVQ 60
PKE1   MGTVSSRRSWWPLPLLLLLLLLLGPAGARAQEDGKPIPNPLLGLDSTQVKLEESGGGLVQ 60
P2.57  MGTVSSRRSWWPLPLLLLLLLLLGPAGARAQEDGKPIPNPLLGLDSTQVKLEESGGGLVQ 60
P2.55  MGTVSSRRSWWPLPLLLLLLLLLGPAGARAQEDGKPIPNPLLGLDSTQVKLEESGGGLVQ 60
P1.40  MGTVSSRRSWWPLPLLLLLLLLLGPAGARAQEDGKPIPNPLLGLDSTQVKLEESGGGLVQ 60
PKE9   MGTVSSRRSWWPLPLLLLLLLLLGPAGARAQEDGKPIPNPLLGLDSTQVKLEESGGGLVQ 60
       *****************************************************:* ********

PKE2   AGGSLRLSCVASGRTINDYILGWFRQAPGKKREFVAAIRCSGAIRGREGSTFYVDSVKGR 120
PKF8   AGGSLRLSCLASDRTVNNYIVGYFRQAPGKEREFVAAIRCSGAIRGREGSTYYADSVKGR 120
PKF1   AGGSLRLSCVASGRTINDYILGWFRQAPGKKREFVAAIRESGS------STYYADSVKGR 114
PKG1   AGGSLRLSCAASGRTPRHYILGWFRQAPGKQREFVAAIRESGS------STYYADSVKGR 114
P1.70  AGGSLRLSCAASGRTFSVYAMGWFRQAPGKEREFVAAITSPGD------SIPYAHSVKGR 114
PKE1   AGGSLRLSCAASGRTFSVYAMGWFRQAPGKEREFVTAITSSGD------SIPYAHSVKGR 114
P2.57  AGGSLRLSCAASGRTFNDYAMGWFRQAPGKEREFVAAAAQSGD------SSAYARSVKGR 114
P2.55  AGGSLRLSCAASGLTFSNYAMGWFRQAPGTEREFVCQISQVDG------FTYYEDSVKGR 114
P1.40  AGGSLRLSCSPSDRTFSAYAMGWFRQVPGREREFVATIRDSDA------SIYYTDSVKGR 114
PKE9   AGGSLRLSCAAPRSGVVIAYMAWYRQAPEKQRELVASISSGT-------TNYAVFAKGR 113
       ********  ..         :.::**.*  :**:*  .      *   .***

PKE2   YTISKDNAKNTVDLQMNSLKPEDSATYYCAVDRFPTPEFSTQVG-HYDYWGQGTQVTVSS 179
PKF8   FSISKDNAKNTIYLQMNSLKPEDSAVYYCALDRFPTPEFTTQVG-HYDVWGRGTQVTVSS 179
PKF1   YTISRNNTKNAVDLQMNSLKPEDSATYYCAVDQYPTPEFSTQVG-HYDYWGQGTQVTVSS 173
PKG1   YTISRDNTKNAVDLQMNSLKPEDSATYYCAVDQYPTPEFSTQVG-HYDYWGQGTQVTVSS 173
P1.70  FTISRDNAKNTLYLQMNSLKPEDTAAYYCAATKSCNYNYMGPDPKKYHYWGQGTQVTVSS 174
PKE1   FTISRDNAKNTVYLQMNSLKPEDTAAYYCAATTSCTYNYMGPDPKEYVYWGQGTQVTVSS 174
P2.57  FTISRDCAKNTAYLQMDSLKPEDTAAYYCAATTRGSYEYMGPDPKKYEYWGQGTQVTVSS 174
P2.55  FTISRDNAKNTVYLQMNSLKPDDTAVYYCAAALA----FPTTSSNTYAYSGQGTQVTVSS 170
P1.40  FTISRDNAKNTVYLQMNSLIPDDTAVYYCAARQYYSGRVYSTFREEYDYWGQGTQVTVSS 174
PKE9   FTISADNAKNTVYLQMNSLKPEDTAVYICNAYAMS-----TETMVSQDYWGQGTQVTVSS 168
       ::** :.:**: ***:** *:*:*.* *                 *:********

PKE2   GS----------HHHHHH 187
PKF8   GS----------HHHHHH 187
PKF1   GS----------HHHHHH 181
PKG1   GS----------HHHHHH 181
P1.70  GS----------HHHHHH 182
PKE1   GS----------HHHHHH 182
P2.57  GSEQKLISEEDLNHHHHHH 193
P2.55  GSEQKLISEEDLNHHHHHH 189
P1.40  GS----------HHHHHH 182
PKE9   GS----------HHHHHH 176
       **          ******
```

QVKLEESGGGLVQAGGSLRLSCAASGLTFSNYAMGWFRQAPGAEREFVGQISQVDGFTYYEDSVKGRFTISRDNAKNTVY
LQMSSLKPDDTAVYYCAATYSGTYNYMGADPKEYVYWGQGTQVTVSSGSEQKLISEEDLNHHHHHH

PKC2

QVKLEESGGGPVQAGGSLRLSCLASGRFVNSPTMAWFRQAPGEERKFVAAIRSRDDSTYYSNSVKGRFTISLDNAKNTAY
LRMDSLQPEDTAVYYCAGDPRTIDLSSRLLWGSWGQGTQVTVSSGSHHHHHH

PKG1-2

QVQLVESGGGLVQAGGSMRLSCAASGRTPRHYILGWFRQAPGKQREFVAAIRESGSRTYYADSVRGRDTISRDNTKNAGD
LQMNSLKPEDSATYYCAVDQYPTTEFSTQVGHYDYWGQGTEVTISSGSHHHHHH

PKA6

QVKLEESGGGLVQAGGSLRLSCAASGRTPRHYIVGWFRQAPGKEREFVAAVRESGSSTEYAENVKGRFVISKDNVKSTVF
LQMNSLKPEDSAVYYCALDRFPTPEFSDRVGHYDLWGQGTQVTVSSGSHHHHHH

PKA11

QVQLVESGGGLVQAGGSMRLSCAASGRTPRHYILGWFRQAPGKQREFVAAIRESGSRTYYADSVRGRYTISRDNTKNAVD
LQMNSLKPEDSATYYCAVDQYPTPEFSTQVGHYDYWGQGTQVTVSSGSHHHHHH

PKC1

QVKLEESGGGLVQAGGSLRLSCAASGRTPRHYILGWFRQAPGKLPEFVAAVREPGSSTYYADSVKGRDTISKDHTKNAVD
LQMNSLKPEDSATYYCAVDPYPTPEFTTHVGHYDYWGQGTQVTVSSGSHHHHHH

PKD8

QVKLEESGGGLVQAGDSLRLSCAASGRIFNHYVTSWFRQAPDQEREFVAGVTAHAGVTADVESTDYSDSVKGRFTVSRDY
SKNTVYLQMNSLKPEDTAVYYCAAPSGFYRTIPHVHSNYDHWGQGTQVTVSSGSHHHHHH

Figure 2B

```
        [-------------FR1------------] [CDR1 [-----FR2----] [-------CDR2
PKE2    QVKLEESGGGLVQAGGSLRLSCVASGRTINDYILGWFRQAPGKKREFVAAIRGSGAIRGR 60
PKF8    QVQLVESGGGLVQAGGSLRLSCLASDRTVNNYIVGYFRQAPGKEREFVAAIRGSGAIRGR 60
PKF1    QVKLEESGGGLVQAGGSLRLSCVASGRTINDYILGWFRQAPGKKREFVAAIRESGS---- 56
PKG1    QVQLVESGGGLVQAGGSLRLSCAASGRTPRHYILGWFRQAPGKQREFVAAIRESGS---- 56
P1.70   QVQLVESGGGLVQAGGSLRLSCAASGRTFSVYAMGWFRQAPGKEREFVAAITSPGD---- 56
PKE1    QVKLEESGGGLVQAGGSLRLSCAASGRTFSVYAMGWFRQAPGKEREFVTAITSSGD---- 56
P2.57   QVKLEESGGGLVQAGGSLRLSCAASGRTFNDYAMGWFRQAPGKEREFVAAAQSGD---- 56
P2.55   QVKLEESGGGLVQAGGSLRLSCAASGLTFSNYAMGWFRQAPGTEREFVGQISQVDG---- 56
P1.40   QVKLEESGGGLVQAGGSLRLSCSPSDRTFSAYAMGWFRQVPGREREFVATIRDSDA---- 56
PKE9    QVKLEESGGGLVQAGGSLRLSCAAPRSGVVIAYMAWYRQAPEKQRELVASISSGGT---- 56

-----------] [-------------FR3--------------] [------CDR3-----
PKE2    EGSTFYVDSVKGRYTISKDNAKNTVDLQMNSLKPEDSATYYCAVDRFPTPEFSTQVG-HY 119
PKF8    EGSTYYADSVKGRFSISKDNAKNTIYLQMNSLKPEDSAVYYCALDRFPTPEFTTQVG-HY 119
PKF1    --STYYADSVKGRYTISRNNTKNAVDLQMNSLKPEDSATYYCAVDQYPTPEFSTQVG-HY 113
PKG1    --STYYADSVKGRYTISRDNTKNAVDLQMNSLKPEDSATYYCAVDQYPTPEFSTQVG-HY 113
P1.70   --SIPYAHSVKGRFTISRDNAKNTLYLQMNSLKPEDTAAYYCAATKSGNYNYMGPDPKKY 114
PKE1    --SIPYAHSVKGRFTISRDNAKNTVYLQMNSLKPEDTAAYYCAATTSGTYNYMGPDPKEY 114
P2.57   --SSAYARSVKGRFTISRDGAKNTAYLQMDSLKPEDTAAYYCAATTRGSYEYMGPDPKKY 114
P2.55   --FTYYEDSVKGRFTISRDNAKNTVYLQMNSLKPDDTAVYYCAAALA----FPTTSSNTY 110
P1.40   --SIYYTDSVKGRFTISRDNAKNTVYLQMNSLIPDDTAVYYCAARQYYSGRVYSTFREEY 114
PKE9    ---TNYAVFAKGRFTISADNAKNTVYLQMNSLKPEDTAVYICNAYAMS-----TETMVSQ 108

-] [----FR4--]
PKE2    DYWGQGTQVTVSSGS 134
PKF8    DVWGRGTQVTVSSGS 134
PKF1    DYWGQGTQVTVSSGS 128
PKG1    DYWGQGTQVTVSSGS 128
P1.70   HYWGQGTQVTVSSGS 129
PKE1    VYWGQGTQVTVSSGS 129
P2.57   EYWGQGTQVTVSSGSEQKLISEEDLN 140
P2.55   AYSGQGTQVTVSSGSEQKLISEEDLN 136
P1.40   DYWGQGTQVTVSSGS 129
PKE9    DYWGQGTQVTVSSGS 123
```

Figure 3A

```
           [-------------FR1------------] [CDR1 [-----FR2----] [-------CDR2
P2.20   QVKLEESGGGLVQAGGSLRLSCAASGLTFSNYAMGWFRQAPGAEREFVGQISQVDG----  56
PKC2    QVKLEESGGGPVQAGGSLRLSCLASGRFVNSPTMAWFRQAPGEERKFVAAIRSRDD----  56
PKG1-2  QVQLVESGGGLVQAGGSMRLSCAASGRTPRHYILGWFRQAPGKQREFVAAIRESGS----  56
PKA6    QVKLEESGGGLVQAGGSLRLSCAASGRTPRHYIVGWFRQAPGKEREFVAAVRESGS----  56
PKA11   QVQLVESGGGLVQAGGSMRLSCAASGRTPRHYILGWFRQAPGKQREFVAAIRESGS----  56
PKC1    QVKLEESGGGLVQAGGSLRLSCAASGRTPRHYILGWFRQAPGKLPEFVAAVREPGS----  56
PKD8    QVKLEESGGGLVQAGDSLRLSCAASGRIFNHYVTSWFRQAPDQEREFVAGVTAHAGVTAD  60

-----------] [-------------FR3---------------] [------CDR3-----
P2.20   --FTYYEDSVKGRFTISRDNAKNTVYLQMSSLKPDDTAVYYCAATYSGTYNYMGADPKEY 114
PKC2    --STYYSNSVKGRFTISLDNAKNTAYLRMDSLQPEDTAVYYCAGDPR-TIDLSSRLLWGS 113
PKG1-2  --RTYYADSVRGRDTISRDNTKNAGDLQMNSLKPEDSATYYCAVDQYPTTEFSTQVG-HY 113
PKA6    --STEYAENVKGRFVISKDNVKSTVFLQMNSLKPEDSAVYYCALDRFPTPEFSDRVG-HY 113
PKA11   --RTYYADSVRGRYTISRDNTKNAVDLQMNSLKPEDSATYYCAVDQYPTPEFSTQVG-HY 113
PKC1    --STYYADSVKGRDTISKDHTKNAVDLQMNSLKPEDSATYYCAVDPYPTPEFTTHVG-HY 113
PKD8    VESTDYSDSVKGRFTVSRDYSKNTVYLQMNSLKPEDTAVYYCAAPSGFYRTIPHVHS-NY 119

-] [----FR4--]
P2.20   VYWGQGTQVTVSSGSEQKLISEEDLN 140
PKC2    --WGQGTQVTVSSGS 126
PKG1-2  DYWGQGTEVTISSGS 128
PKA6    DLWGQGTQVTVSSGS 128
PKA11   DYWGQGTQVTVSSGS 128
PKC1    DYWGQGTQVTVSSGS 128
PKD8    DHWGQGTQVTVSSGS 134
```

Figure 3B

```
         [------------FR1------------] [CDR1 [-----FR2----] [-------CDR2
PKE2     QVKLEESGGGLVQAGGSLRLSCVASGRTINDYILGWFRQAPGKKREFVAAIRGSGAIRGR 60
PKF8     QVQLVESGGGLVQAGGSLRLSCLASDRTVNNYIVGYFRQAPGKEREFVAAIRGSGAIRGR 60
PKF1     QVKLEESGGGLVQAGGSLRLSCVASGRTINDYILGWFRQAPGKKREFVAAIRESGS---- 56
PKG1     QVQLVESGGGLVQAGGSLRLSCAASGRTPRHYILGWFRQAPGKQREFVAAIRESGS---- 56
P1.70    QVQLVESGGGLVQAGGSLRLSCAASGRTFSVYAMGWFRQAPGKEREFVAAITSPGD---- 56
PKE1     QVKLEESGGGLVQAGGSLRLSCAASGRTFSVYAMGWFRQAPGKEREFVTAITSSGD---- 56
P2.57    QVKLEESGGGLVQAGGSLRLSCAASGRTFNDYAMGWFRQAPGKEREFVAAAQSGD---- 56
P2.55    QVKLEESGGGLVQAGGSLRLSCAASGLTFSNYAMGWFRQAPGTEREFVGQISQVDG---- 56
P1.40    QVKLEESGGGLVQAGGSLRLSCSPSDRTFSAYAMGWFRQVPGREREFVATIRDSDA---- 56
PKE9     QVKLEESGGGLVQAGGSLRLSCAAPRSGVVIAYMAWYRQAPEKQRELVASISSGGT---- 56
P2.20    QVKLEESGGGLVQAGGSLRLSCAASGLTFSNYAMGWFRQAPGAEREFVGQISQVDG---- 56
PKC2     QVKLEESGGGPVQAGGSLRLSCLASGRFVNSPTMAWFRQAPGEERKFVAAIRSRDD---- 56
PKG1-2   QVQLVESGGGLVQAGGSMRLSCAASGRTPRHYILGWFRQAPGKQREFVAAIRESGS---- 56
PKA6     QVKLEESGGGLVQAGGSLRLSCAASGRTPRHYIVGWFRQAPGKEREFVAAVRESGS---- 56
PKA11    QVQLVESGGGLVQAGGSMRLSCAASGRTPRHYILGWFRQAPGKQREFVAAIRESGS---- 56
PKC1     QVKLEESGGGLVQAGGSLRLSCAASGRTPRHYILGWFRQAPGKLPEFVAAVREPGS---- 56
PKD8     QVKLEESGGGLVQAGDSLRLSCAASGRIFNHYVTSWFRQAPDQEREFVAGVTAHAGVTAD 60

-----------] [-------------FR3---------------] [------CDR3-----
PKE2     EGSTFYVDSVKGRYTISKDNAKNTVDLQMNSLKPEDSATYYCAVDRFPTPEFSTQVG-HY 119
PKF8     EGSTYYADSVKGRFSISKDNAKNTIYLQMNSLKPEDSAVYYCALDRFPTPEFTTQVG-HY 119
PKF1     --STYYADSVKGRYTISRNNTKNAVDLQMNSLKPEDSATYYCAVDQYPTPEFSTQVG-HY 113
PKG1     --STYYADSVKGRYTISRDNTKNAVDLQMNSLKPEDSATYYCAVDQYPTPEFSTQVG-HY 113
P1.70    --SIPYAHSVKGRFTISRDNAKNTLYLQMNSLKPEDTAAYYCAATKSGNYNYMGPDPKKY 114
PKE1     --SIPYAHSVKGRFTISRDNAKNTVYLQMNSLKPEDTAAYYCAATTSGTYNYMGPDPKEY 114
P2.57    --SSAYARSVKGRFTISRDGAKNTAYLQMDSLKPEDTAAYYCAATTRGSYEYMGPDPKKY 114
P2.55    --FTYYEDSVKGRFTISRDNAKNTVYLQMNSLKPDDTAVYYCAAALA----FPTTSSNTY 110
P1.40    --SIYYTDSVKGRFTISRDNAKNTVYLQMNSLIPDDTAVYYCAARQYYSGRVYSTFREEY 114
PKE9     ---TNYAVFAKGRFTISADNAKNTVYLQMNSLKPEDTAVYICNAYAMS-----TETMVSQ 108
P2.20    --FTYYEDSVKGRFTISRDNAKNTVYLQMSSLKPDDTAVYYCAATYSGTYNYMGADPKEY 114
PKC2     --STYYSNSVKGRFTISLDNAKNTAYLRMDSLQPEDTAVYYCAGDPR-TIDLSSRLLWGS 113
PKG1-2   --RTYYADSVRGRDTISRDNTKNAGDLQMNSLKPEDSATYYCAVDQYPTTEFSTQVG-HY 113
PKA6     --STEYAENVKGRFVISKDNVKSTVFLQMNSLKPEDSAVYYCALDRFPTPEFSDRVG-HY 113
PKA11    --RTYYADSVRGRYTISRDNTKNAVDLQMNSLKPEDSATYYCAVDQYPTPEFSTQVG-HY 113
PKC1     --STYYADSVKGRDTISKDHTKNAVDLQMNSLKPEDSATYYCAVDPYPTPEFTTHVG-HY 113
PKD8     VESTDYSDSVKGRFTVSRDYSKNTVYLQMNSLKPEDTAVYYCAAPSGFYRTIPHVHS-NY 119
```

Figure 3C

```
         -][----FR4--]
PKE2    DYWGQGTQVTVSSGS 134
PKF8    DVWGRGTQVTVSSGS 134
PKF1    DYWGQGTQVTVSSGS 128
PKG1    DYWGQGTQVTVSSGS 128
P1.70   HYWGQGTQVTVSSGS 129
PKE1    VYWGQGTQVTVSSGS 129
P2.57   EYWGQGTQVTVSSGSEQKLISEEDLN 140
P2.55   AYSGQGTQVTVSSGSEQKLISEEDLN 136
P1.40   DYWGQGTQVTVSSGS 129
PKE9    DYWGQGTQVTVSSGS 123
P2.20   VYWGQGTQVTVSSGSEQKLISEEDLN 140
PKC2    --WGQGTQVTVSSGS 126
PKG1-2  DYWGQGTEVTISSGS 128
PKA6    DLWGQGTQVTVSSGS 128
PKA11   DYWGQGTQVTVSSGS 128
PKC1    DYWGQGTQVTVSSGS 128
PKD8    DHWGQGTQVTVSSGS 134
```

Figure 3C (continued)

1) 80.95% identity

```
[PKG1-2]   QVQLVESGGGLVQAGGSMRLSCAASGRTPRHYILGWFRQAPGKQREFVAAIRESGSRTYY 60
[PKA11]    QVQLVESGGGLVQAGGSMRLSCAASGRTPRHYILGWFRQAPGKQREFVAAIRESGSRTYY 60
[PKG1]     QVQLVESGGGLVQAGGSLRLSCAASGRTPRHYILGWFRQAPGKQREFVAAIRESGSSTYY 60
[PKF1]     QVKLEESGGGLVQAGGSLRLSCVASGRTINDYILGWFRQAPGKKREFVAAIRESGSSTYY 60
[PKC1]     QVKLEESGGGLVQAGGSLRLSCAASGRTPRHYILGWFRQAPGKLPEFVAAVREPGSSTYY 60
           **:* *************:****.*****  .************  *****:**.** ***

[PKG1-2]   ADSVRGRDTISRDNTKNAGDLQMNSLKPEDSATYYCAVDQYPTTEFSTQVGHYDYWGQGT 120
[PKA11]    ADSVRGRYTISRDNTKNAVDLQMNSLKPEDSATYYCAVDQYPTPEFSTQVGHYDYWGQGT 120
[PKG1]     ADSVKGRYTISRDNTKNAVDLQMNSLKPEDSATYYCAVDQYPTPEFSTQVGHYDYWGQGT 120
[PKF1]     ADSVKGRYTISRNNTKNAVDLQMNSLKPEDSATYYCAVDQYPTPEFSTQVGHYDYWGQGT 120
[PKC1]     ADSVKGRDTISKDHTKNAVDLQMNSLKPEDSATYYCAVDPYPTPEFTTHVGHYDYWGQGT 120
           ****:** ***:::****  *******************.***.**:*:***********

[PKG1-2]   EVTISS 126
[PKA11]    QVTVSS 126
[PKG1]     QVTVSS 126
[PKF1]     QVTVSS 126
[PKC1]     QVTVSS 126
           :**:**
```

2) 83.46% identity

```
[P1.70]    QVQLVESGGGLVQAGGSLRLSCAASGRTFSVYAMGWFRQAPGKEREFVAAITSPGDSIPY 60
[PKE1]     QVKLEESGGGLVQAGGSLRLSCAASGRTFSVYAMGWFRQAPGKEREFVTAITSSGDSIPY 60
[P2.57]    QVKLEESGGGLVQAGGSLRLSCAASGRTFNDYAMGWFRQAPGKEREFVAAAQSGDSSAY 60
           **:* *********************.  *****************:* :...*** .*

[P1.70]    AHSVKGRFTISRDNAKNTLYLQMNSLKPEDTAAYYCAATKSGNYNYMGPDPKKYHYWGQG 120
[PKE1]     AHSVKGRFTISRDNAKNTVYLQMNSLKPEDTAAYYCAATTSGTYNYMGPDPKEYVYWGQG 120
[P2.57]    ARSVKGRFTISRDGAKNTAYLQMDSLKPEDTAAYYCAATTRGSYEYMGPDPKKYEYWGQG 120
           *:***********.**** ****:************.  *.*:*******:* *****

[P1.70]    TQVTVSS 127
[PKE1]     TQVTVSS 127
[P2.57]    TQVTVSS 127
           *******
```

3) 87.30% identity

```
[PKG1-2]   QVQLVESGGGLVQAGGSMRLSCAASGRTPRHYILGWFRQAPGKQREFVAAIRESGSRTYY 60
[PKA11]    QVQLVESGGGLVQAGGSMRLSCAASGRTPRHYILGWFRQAPGKQREFVAAIRESGSRTYY 60
[PKG1]     QVQLVESGGGLVQAGGSLRLSCAASGRTPRHYILGWFRQAPGKQREFVAAIRESGSSTYY 60
[PKF1]     QVKLEESGGGLVQAGGSLRLSCVASGRTINDYILGWFRQAPGKKREFVAAIRESGSSTYY 60
           **:* *************:****.*****  .************:************ ***

[PKG1-2]   ADSVRGRDTISRDNTKNAGDLQMNSLKPEDSATYYCAVDQYPTTEFSTQVGHYDYWGQGT 120
[PKA11]    ADSVRGRYTISRDNTKNAVDLQMNSLKPEDSATYYCAVDQYPTPEFSTQVGHYDYWGQGT 120
[PKG1]     ADSVKGRYTISRDNTKNAVDLQMNSLKPEDSATYYCAVDQYPTPEFSTQVGHYDYWGQGT 120
[PKF1]     ADSVKGRYTISRNNTKNAVDLQMNSLKPEDSATYYCAVDQYPTPEFSTQVGHYDYWGQGT 120
           ****:** ****:***** *******************.****************

[PKG1-2]   EVTISS 126
[PKA11]    QVTVSS 126
[PKG1]     QVTVSS 126
[PKF1]     QVTVSS 126
           :**:**
```

Figure 3D

Comparison of (SEQ ID NO: 93) PKE2 with other sdAbs

| Description | Max score | Total score | Query cover | E value | Max ident |
|---|---|---|---|---|---|
| (SEQ ID NO: 93); [PKE2] | 273 | 273 | 100% | 6e-100 | 100% |
| (SEQ ID NO: 94); [PKF8] | 239 | 239 | 100% | 1e-86 | 85% |
| (SEQ ID NO: 95); [PKF1] | 239 | 239 | 100% | 2e-86 | 88% |
| (SEQ ID NO: 96); [PKG1] | 225 | 225 | 100% | 4e-81 | 83% |
| (SEQ ID NO: 97); [P1.70] | 165 | 165 | 100% | 2e-57 | 64% |
| (SEQ ID NO: 98); [PKE1] | 169 | 169 | 100% | 3e-59 | 68% |
| (SEQ ID NO: 99); [P2.57] | 171 | 171 | 100% | 5e-60 | 68% |
| (SEQ ID NO: 100); [P2.55] | 167 | 167 | 100% | 1e-58 | 68% |
| (SEQ ID NO: 101); [P1.40] | 172 | 172 | 100% | 3e-60 | 67% |
| (SEQ ID NO: 102); [PKE9] | 142 | 142 | 100% | 7e-49 | 61% |
| (SEQ ID NO: 103); [P2.20] | 165 | 165 | 100% | 2e-57 | 65% |
| (SEQ ID NO: 104); [PKC2] | 157 | 157 | 100% | 2e-54 | 64% |
| (SEQ ID NO: 105); [PKG1-2] | 209 | 209 | 100% | 5e-75 | 77% |
| (SEQ ID NO: 106); [PKA6] | 210 | 210 | 100% | 4e-75 | 78% |
| (SEQ ID NO: 107); [PKA11] | 221 | 221 | 100% | 1e-79 | 81% |
| (SEQ ID NO: 108); [PKC1] | 215 | 215 | 100% | 3e-77 | 80% |
| (SEQ ID NO: 109); [PKD8] | 164 | 164 | 100% | 4e-57 | 63% |

Comparison of (SEQ ID NO: 94) PKF8 with other sdAbs

| Description | Max score | Total score | Query cover | E value | Max ident |
|---|---|---|---|---|---|
| (SEQ ID NO: 93); [PKE2] | 239 | 239 | 100% | 1e-86 | 85% |
| (SEQ ID NO: 94); [PKF8] | 273 | 273 | 100% | 8e-100 | 100% |
| (SEQ ID NO: 95); [PKF1] | 210 | 210 | 100% | 2e-75 | 76% |
| (SEQ ID NO: 96); [PKG1] | 211 | 211 | 100% | 2e-75 | 77% |
| (SEQ ID NO: 97); [P1.70] | 165 | 165 | 100% | 2e-57 | 65% |
| (SEQ ID NO: 98); [PKE1] | 160 | 160 | 100% | 1e-55 | 65% |
| (SEQ ID NO: 99); [P2.57] | 160 | 160 | 100% | 7e-56 | 65% |
| (SEQ ID NO: 100); [P2.55] | 161 | 161 | 100% | 5e-56 | 66% |
| (SEQ ID NO: 101); [P1.40] | 169 | 169 | 100% | 7e-59 | 65% |
| (SEQ ID NO: 102); [PKE9] | 137 | 137 | 100% | 9e-47 | 59% |
| (SEQ ID NO: 103); [P2.20] | 159 | 159 | 100% | 3e-55 | 64% |
| (SEQ ID NO: 104); [PKC2] | 156 | 156 | 100% | 4e-54 | 64% |
| (SEQ ID NO: 105); [PKG1-2] | 197 | 197 | 100% | 4e-70 | 73% |
| (SEQ ID NO: 106); [PKA6] | 209 | 209 | 100% | 6e-75 | 77% |
| (SEQ ID NO: 107); [PKA11] | 207 | 207 | 100% | 4e-74 | 75% |
| (SEQ ID NO: 108); [PKC1] | 196 | 196 | 100% | 1e-69 | 73% |
| (SEQ ID NO: 109); [PKD8] | 158 | 158 | 100% | 8e-55 | 60% |

Figure 3E

Comparison of (SEQ ID NO: 95) PKF1 with other sdAbs

| Description | Max score | Total score | Query cover | E value | Max ident |
|---|---|---|---|---|---|
| (SEQ ID NO: 93); [PKE2] | 239 | 239 | 100% | 2e-86 | 88% |
| (SEQ ID NO: 94); [PKF8] | 210 | 210 | 100% | 2e-75 | 76% |
| (SEQ ID NO: 95); [PKF1] | 262 | 262 | 100% | 1e-95 | 100% |
| (SEQ ID NO: 96); [PKG1] | 244 | 244 | 100% | 9e-89 | 94% |
| (SEQ ID NO: 97); [P1.70] | 169 | 169 | 100% | 3e-59 | 66% |
| (SEQ ID NO: 98); [PKE1] | 174 | 174 | 100% | 4e-61 | 71% |
| (SEQ ID NO: 99); [P2.57] | 178 | 178 | 100% | 1e-62 | 70% |
| (SEQ ID NO: 100); [P2.55] | 167 | 167 | 100% | 2e-58 | 68% |
| (SEQ ID NO: 101); [P1.40] | 179 | 179 | 100% | 6e-63 | 70% |
| (SEQ ID NO: 102); [PKE9] | 142 | 142 | 100% | 1e-48 | 61% |
| (SEQ ID NO: 103); [P2.20] | 165 | 165 | 100% | 1e-57 | 66% |
| (SEQ ID NO: 104); [PKC2] | 159 | 159 | 100% | 3e-55 | 64% |
| (SEQ ID NO: 105); [PKG1-2] | 229 | 229 | 100% | 8e-83 | 87% |
| (SEQ ID NO: 106); [PKA6] | 216 | 216 | 100% | 1e-77 | 80% |
| (SEQ ID NO: 107); [PKA11] | 241 | 241 | 100% | 2e-87 | 91% |
| (SEQ ID NO: 108); [PKC1] | 231 | 231 | 100% | 1e-83 | 88% |
| (SEQ ID NO: 109); [PKD8] | 157 | 157 | 100% | 1e-54 | 62% |

Comparison of (SEQ ID NO: 96) PKG1 with other sdAbs

| Description | Max score | Total score | Query cover | E value | Max ident |
|---|---|---|---|---|---|
| (SEQ ID NO: 93); [PKE2] | 225 | 225 | 100% | 4e-81 | 83% |
| (SEQ ID NO: 94); [PKF8] | 211 | 211 | 100% | 2e-75 | 77% |
| (SEQ ID NO: 95); [PKF1] | 244 | 244 | 100% | 9e-89 | 94% |
| (SEQ ID NO: 96); [PKG1] | 261 | 261 | 100% | 1e-95 | 100% |
| (SEQ ID NO: 97); [P1.70] | 174 | 174 | 100% | 4e-61 | 69% |
| (SEQ ID NO: 98); [PKE1] | 171 | 171 | 100% | 5e-60 | 71% |
| (SEQ ID NO: 99); [P2.57] | 170 | 170 | 100% | 2e-59 | 69% |
| (SEQ ID NO: 100); [P2.55] | 164 | 164 | 100% | 3e-57 | 68% |
| (SEQ ID NO: 101); [P1.40] | 176 | 176 | 100% | 1e-61 | 69% |
| (SEQ ID NO: 102); [PKE9] | 141 | 141 | 100% | 3e-48 | 62% |
| (SEQ ID NO: 103); [P2.20] | 162 | 162 | 100% | 2e-56 | 66% |
| (SEQ ID NO: 104); [PKC2] | 150 | 150 | 100% | 6e-52 | 63% |
| (SEQ ID NO: 105); [PKG1-2] | 247 | 247 | 100% | 9e-90 | 94% |
| (SEQ ID NO: 106); [PKA6] | 224 | 224 | 100% | 6e-81 | 83% |
| (SEQ ID NO: 107); [PKA11] | 258 | 258 | 100% | 4e-94 | 98% |
| (SEQ ID NO: 108); [PKC1] | 238 | 238 | 100% | 3e-86 | 90% |
| (SEQ ID NO: 109); [PKD8] | 155 | 155 | 100% | 9e-54 | 62% |

Figure 3E (continued)

Comparison of (SEQ ID NO: 97) P1.70 with other sdAbs

| Description | Max score | Total score | Query cover | E value | Max ident |
|---|---|---|---|---|---|
| (SEQ ID NO: 93); [PKE2] | 165 | 165 | 100% | 2e-57 | 64% |
| (SEQ ID NO: 94); [PKF8] | 165 | 165 | 100% | 2e-57 | 65% |
| (SEQ ID NO: 95); [PKF1] | 169 | 169 | 100% | 3e-59 | 66% |
| (SEQ ID NO: 96); [PKG1] | 174 | 174 | 100% | 4e-61 | 69% |
| (SEQ ID NO: 97); [P1.70] | 266 | 266 | 100% | 3e-97 | 100% |
| (SEQ ID NO: 98); [PKE1] | 246 | 246 | 100% | 1e-89 | 93% |
| (SEQ ID NO: 99); [P2.57] | 223 | 223 | 100% | 1e-80 | 85% |
| (SEQ ID NO: 100); [P2.55] | 172 | 172 | 100% | 2e-60 | 71% |
| (SEQ ID NO: 101); [P1.40] | 181 | 181 | 100% | 9e-64 | 71% |
| (SEQ ID NO: 102); [PKE9] | 147 | 147 | 100% | 6e-51 | 63% |
| (SEQ ID NO: 103); [P2.20] | 205 | 205 | 100% | 2e-73 | 80% |
| (SEQ ID NO: 104); [PKC2] | 155 | 155 | 100% | 1e-53 | 62% |
| (SEQ ID NO: 105); [PKG1-2] | 165 | 165 | 100% | 1e-57 | 67% |
| (SEQ ID NO: 106); [PKA6] | 169 | 169 | 100% | 5e-59 | 65% |
| (SEQ ID NO: 107); [PKA11] | 171 | 171 | 100% | 7e-60 | 67% |
| (SEQ ID NO: 108); [PKC1] | 160 | 160 | 100% | 6e-56 | 65% |
| (SEQ ID NO: 109); [PKD8] | 167 | 167 | 100% | 2e-58 | 65% |

Comparison of (SEQ ID NO: 98) PKE1 with other sdAbs

| Description | Max score | Total score | Query cover | E value | Max ident |
|---|---|---|---|---|---|
| (SEQ ID NO: 93); [PKE2] | 169 | 169 | 100% | 3e-59 | 68% |
| (SEQ ID NO: 94); [PKF8] | 160 | 160 | 100% | 1e-55 | 65% |
| (SEQ ID NO: 95); [PKF1] | 174 | 174 | 100% | 4e-61 | 71% |
| (SEQ ID NO: 96); [PKG1] | 171 | 171 | 100% | 5e-60 | 71% |
| (SEQ ID NO: 97); [P1.70] | 246 | 246 | 100% | 1e-89 | 93% |
| (SEQ ID NO: 98); [PKE1] | 264 | 264 | 100% | 2e-96 | 100% |
| (SEQ ID NO: 99); [P2.57] | 228 | 228 | 100% | 2e-82 | 87% |
| (SEQ ID NO: 100); [P2.55] | 177 | 177 | 100% | 1e-62 | 73% |
| (SEQ ID NO: 101); [P1.40] | 186 | 186 | 100% | 1e-65 | 74% |
| (SEQ ID NO: 102); [PKE9] | 155 | 155 | 100% | 1e-53 | 66% |
| (SEQ ID NO: 103); [P2.20] | 216 | 216 | 100% | 2e-77 | 84% |
| (SEQ ID NO: 104); [PKC2] | 157 | 157 | 100% | 1e-54 | 63% |
| (SEQ ID NO: 105); [PKG1-2] | 161 | 161 | 100% | 4e-56 | 66% |
| (SEQ ID NO: 106); [PKA6] | 174 | 174 | 100% | 5e-61 | 70% |
| (SEQ ID NO: 107); [PKA11] | 167 | 167 | 100% | 1e-58 | 69% |
| (SEQ ID NO: 108); [PKC1] | 162 | 162 | 100% | 1e-56 | 69% |
| (SEQ ID NO: 109); [PKD8] | 171 | 171 | 100% | 7e-60 | 67% |

Figure 3E (continued)

Comparison of (SEQ ID NO: 99) P2.57 with other sdAbs

| Description | Max score | Total score | Query cover | E value | Max ident |
|---|---|---|---|---|---|
| (SEQ ID NO: 93); [PKE2] | 171 | 171 | 100% | 5e-60 | 68% |
| (SEQ ID NO: 94); [PKF8] | 160 | 160 | 100% | 7e-56 | 65% |
| (SEQ ID NO: 95); [PKF1] | 178 | 178 | 100% | 1e-62 | 70% |
| (SEQ ID NO: 96); [PKG1] | 170 | 170 | 100% | 2e-59 | 69% |
| (SEQ ID NO: 97); [P1.70] | 223 | 223 | 100% | 1e-80 | 85% |
| (SEQ ID NO: 98); [PKE1] | 228 | 228 | 100% | 2e-82 | 87% |
| (SEQ ID NO: 99); [P2.57] | 259 | 259 | 100% | 7e-95 | 100% |
| (SEQ ID NO: 100); [P2.55] | 173 | 173 | 100% | 9e-61 | 70% |
| (SEQ ID NO: 101); [P1.40] | 175 | 175 | 100% | 2e-61 | 70% |
| (SEQ ID NO: 102); [PKE9] | 144 | 144 | 100% | 1e-49 | 62% |
| (SEQ ID NO: 103); [P2.20] | 203 | 203 | 100% | 2e-72 | 78% |
| (SEQ ID NO: 104); [PKC2] | 161 | 161 | 100% | 5e-56 | 64% |
| (SEQ ID NO: 105); [PKG1-2] | 162 | 162 | 100% | 3e-56 | 65% |
| (SEQ ID NO: 106); [PKA6] | 173 | 173 | 100% | 9e-61 | 69% |
| (SEQ ID NO: 107); [PKA11] | 166 | 166 | 100% | 6e-58 | 66% |
| (SEQ ID NO: 108); [PKC1] | 165 | 165 | 100% | 2e-57 | 68% |
| (SEQ ID NO: 109); [PKD8] | 171 | 171 | 100% | 4e-60 | 67% |

Comparison of (SEQ ID NO: 100) P2.55 with other sdAbs

| Description | Max score | Total score | Query cover | E value | Max ident |
|---|---|---|---|---|---|
| (SEQ ID NO: 93); [PKE2] | 167 | 167 | 100% | 1e-58 | 68% |
| (SEQ ID NO: 94); [PKF8] | 161 | 161 | 100% | 5e-56 | 66% |
| (SEQ ID NO: 95); [PKF1] | 167 | 167 | 100% | 2e-58 | 68% |
| (SEQ ID NO: 96); [PKG1] | 164 | 164 | 100% | 3e-57 | 68% |
| (SEQ ID NO: 97); [P1.70] | 172 | 172 | 100% | 2e-60 | 71% |
| (SEQ ID NO: 98); [PKE1] | 177 | 177 | 100% | 1e-62 | 73% |
| (SEQ ID NO: 99); [P2.57] | 173 | 173 | 100% | 9e-61 | 70% |
| (SEQ ID NO: 100); [P2.55] | 253 | 253 | 100% | 3e-92 | 100% |
| (SEQ ID NO: 101); [P1.40] | 181 | 181 | 100% | 4e-64 | 74% |
| (SEQ ID NO: 102); [PKE9] | 143 | 143 | 100% | 4e-49 | 66% |
| (SEQ ID NO: 103); [P2.20] | 216 | 216 | 100% | 2e-77 | 85% |
| (SEQ ID NO: 104); [PKC2] | 155 | 155 | 100% | 1e-53 | 65% |
| (SEQ ID NO: 105); [PKG1-2] | 157 | 157 | 100% | 1e-54 | 65% |
| (SEQ ID NO: 106); [PKA6] | 161 | 161 | 100% | 2e-56 | 66% |
| (SEQ ID NO: 107); [PKA11] | 162 | 162 | 100% | 1e-56 | 66% |
| (SEQ ID NO: 108); [PKC1] | 159 | 159 | 100% | 3e-55 | 66% |
| (SEQ ID NO: 109); [PKD8] | 165 | 165 | 100% | 1e-57 | 67% |

Figure 3E (continued)

Comparison of (SEQ ID NO: 101) P1.40 with other sdAbs

| Description | Max score | Total score | Query cover | E value | Max ident |
|---|---|---|---|---|---|
| (SEQ ID NO: 93); [PKE2] | 172 | 172 | 100% | 3e-60 | 67% |
| (SEQ ID NO: 94); [PKF8] | 169 | 169 | 100% | 7e-59 | 65% |
| (SEQ ID NO: 95); [PKF1] | 179 | 179 | 100% | 6e-63 | 70% |
| (SEQ ID NO: 96); [PKG1] | 176 | 176 | 100% | 1e-61 | 69% |
| (SEQ ID NO: 97); [P1.70] | 181 | 181 | 100% | 9e-64 | 71% |
| (SEQ ID NO: 98); [PKE1] | 186 | 186 | 100% | 1e-65 | 74% |
| (SEQ ID NO: 99); [P2.57] | 175 | 175 | 100% | 2e-61 | 70% |
| (SEQ ID NO: 100); [P2.55] | 181 | 181 | 100% | 4e-64 | 74% |
| (SEQ ID NO: 101); [P1.40] | 261 | 261 | 100% | 3e-95 | 100% |
| (SEQ ID NO: 102); [PKE9] | 142 | 142 | 100% | 8e-49 | 63% |
| (SEQ ID NO: 103); [P2.20] | 183 | 183 | 100% | 1e-64 | 75% |
| (SEQ ID NO: 104); [PKC2] | 156 | 156 | 100% | 3e-54 | 65% |
| (SEQ ID NO: 105); [PKG1-2] | 164 | 164 | 100% | 2e-57 | 65% |
| (SEQ ID NO: 106); [PKA6] | 169 | 169 | 100% | 3e-59 | 65% |
| (SEQ ID NO: 107); [PKA11] | 171 | 171 | 100% | 5e-60 | 67% |
| (SEQ ID NO: 108); [PKC1] | 167 | 167 | 100% | 2e-58 | 65% |
| (SEQ ID NO: 109); [PKD8] | 159 | 159 | 100% | 2e-55 | 63% |

Comparison of (SEQ ID NO: 102 PKE9 with other sdAbs

| Description | Max score | Total score | Query cover | E value | Max ident |
|---|---|---|---|---|---|
| (SEQ ID NO: 93); [PKE2] | 142 | 142 | 100% | 7e-49 | 61% |
| (SEQ ID NO: 94); [PKF8] | 137 | 137 | 100% | 9e-47 | 59% |
| (SEQ ID NO: 95); [PKF1] | 142 | 142 | 100% | 1e-48 | 61% |
| (SEQ ID NO: 96); [PKG1] | 141 | 141 | 100% | 3e-48 | 62% |
| (SEQ ID NO: 97); [P1.70] | 147 | 147 | 100% | 6e-51 | 63% |
| (SEQ ID NO: 98); [PKE1] | 155 | 155 | 100% | 1e-53 | 66% |
| (SEQ ID NO: 99); [P2.57] | 144 | 144 | 100% | 1e-49 | 62% |
| (SEQ ID NO: 100); [P2.55] | 143 | 143 | 100% | 4e-49 | 66% |
| (SEQ ID NO: 101); [P1.40] | 142 | 142 | 100% | 8e-49 | 63% |
| (SEQ ID NO: 102); [PKE9] | 249 | 249 | 100% | 6e-91 | 100% |
| (SEQ ID NO: 103); [P2.20] | 144 | 144 | 100% | 1e-49 | 64% |
| (SEQ ID NO: 104); [PKC2] | 135 | 135 | 100% | 6e-46 | 60% |
| (SEQ ID NO: 105); [PKG1-2] | 131 | 131 | 100% | 2e-44 | 58% |
| (SEQ ID NO: 106); [PKA6] | 145 | 145 | 100% | 7e-50 | 62% |
| (SEQ ID NO: 107); [PKA11] | 138 | 138 | 100% | 3e-47 | 60% |
| (SEQ ID NO: 108); [PKC1] | 134 | 134 | 100% | 1e-45 | 58% |
| (SEQ ID NO: 109); [PKD8] | 142 | 142 | 100% | 9e-49 | 57% |

Figure 3E (continued)

Comparison of (SEQ ID NO: 103) P2.20 with other sdAbs

| Description | Max score | Total score | Query cover | E value | Max ident |
|---|---|---|---|---|---|
| (SEQ ID NO: 93); [PKE2] | 165 | 165 | 100% | 2e-57 | 65% |
| (SEQ ID NO: 94); [PKF8] | 159 | 159 | 100% | 3e-55 | 64% |
| (SEQ ID NO: 95); [PKF1] | 165 | 165 | 100% | 1e-57 | 66% |
| (SEQ ID NO: 96); [PKG1] | 162 | 162 | 100% | 2e-56 | 66% |
| (SEQ ID NO: 97); [P1.70] | 205 | 205 | 100% | 2e-73 | 80% |
| (SEQ ID NO: 98); [PKE1] | 216 | 216 | 100% | 2e-77 | 84% |
| (SEQ ID NO: 99); [P2.57] | 203 | 203 | 100% | 2e-72 | 78% |
| (SEQ ID NO: 100); [P2.55] | 216 | 216 | 100% | 2e-77 | 85% |
| (SEQ ID NO: 101); [P1.40] | 183 | 183 | 100% | 1e-64 | 75% |
| (SEQ ID NO: 102); [PKE9] | 144 | 144 | 100% | 1e-49 | 64% |
| (SEQ ID NO: 103); [P2.20] | 261 | 261 | 100% | 1e-95 | 100% |
| (SEQ ID NO: 104); [PKC2] | 154 | 154 | 100% | 3e-53 | 61% |
| (SEQ ID NO: 105); [PKG1-2] | 154 | 154 | 100% | 2e-53 | 62% |
| (SEQ ID NO: 106); [PKA6] | 160 | 160 | 100% | 1e-55 | 65% |
| (SEQ ID NO: 107); [PKA11] | 160 | 160 | 100% | 7e-56 | 65% |
| (SEQ ID NO: 108); [PKC1] | 157 | 157 | 100% | 2e-54 | 65% |
| (SEQ ID NO: 109); [PKD8] | 166 | 166 | 100% | 5e-58 | 66% |

Comparison of (SEQ ID NO: 104) PKC2 with other sdAbs

| Description | Max score | Total score | Query cover | E value | Max ident |
|---|---|---|---|---|---|
| (SEQ ID NO: 93); [PKE2] | 157 | 157 | 100% | 2e-54 | 64% |
| (SEQ ID NO: 94); [PKF8] | 156 | 156 | 100% | 4e-54 | 64% |
| (SEQ ID NO: 95); [PKF1] | 159 | 159 | 100% | 3e-55 | 64% |
| (SEQ ID NO: 96); [PKG1] | 150 | 150 | 100% | 6e-52 | 63% |
| (SEQ ID NO: 97); [P1.70] | 155 | 155 | 100% | 1e-53 | 62% |
| (SEQ ID NO: 98); [PKE1] | 157 | 157 | 100% | 1e-54 | 63% |
| (SEQ ID NO: 99); [P2.57] | 161 | 161 | 100% | 5e-56 | 64% |
| (SEQ ID NO: 100); [P2.55] | 155 | 155 | 100% | 1e-53 | 65% |
| (SEQ ID NO: 101); [P1.40] | 156 | 156 | 100% | 3e-54 | 65% |
| (SEQ ID NO: 102); [PKE9] | 135 | 135 | 100% | 6e-46 | 60% |
| (SEQ ID NO: 103); [P2.20] | 154 | 154 | 100% | 3e-53 | 61% |
| (SEQ ID NO: 104); [PKC2] | 256 | 256 | 100% | 2e-93 | 100% |
| (SEQ ID NO: 105); [PKG1-2] | 143 | 143 | 100% | 5e-49 | 59% |
| (SEQ ID NO: 106); [PKA6] | 153 | 153 | 100% | 4e-53 | 64% |
| (SEQ ID NO: 107); [PKA11] | 146 | 146 | 100% | 2e-50 | 60% |
| (SEQ ID NO: 108); [PKC1] | 147 | 147 | 100% | 8e-51 | 62% |
| (SEQ ID NO: 109); [PKD8] | 149 | 149 | 100% | 2e-51 | 62% |

Figure 3E (continued)

Comparison of (SEQ ID NO: 105) PKG1-2 with other sdAbs

| Description | Max score | Total score | Query cover | E value | Max ident |
|---|---|---|---|---|---|
| (SEQ ID NO: 93); [PKE2] | 209 | 209 | 100% | 5e-75 | 77% |
| (SEQ ID NO: 94); [PKF8] | 197 | 197 | 100% | 4e-70 | 73% |
| (SEQ ID NO: 95); [PKF1] | 229 | 229 | 100% | 8e-83 | 87% |
| (SEQ ID NO: 96); [PKG1] | 247 | 247 | 100% | 9e-90 | 94% |
| (SEQ ID NO: 97); [P1.70] | 165 | 165 | 100% | 1e-57 | 67% |
| (SEQ ID NO: 98); [PKE1] | 161 | 161 | 100% | 4e-56 | 66% |
| (SEQ ID NO: 99); [P2.57] | 162 | 162 | 100% | 3e-56 | 65% |
| (SEQ ID NO: 100); [P2.55] | 157 | 157 | 100% | 1e-54 | 65% |
| (SEQ ID NO: 101); [P1.40] | 164 | 164 | 100% | 2e-57 | 65% |
| (SEQ ID NO: 102); [PKE9] | 131 | 131 | 100% | 2e-44 | 58% |
| (SEQ ID NO: 103); [P2.20] | 154 | 154 | 100% | 2e-53 | 62% |
| (SEQ ID NO: 104); [PKC2] | 143 | 143 | 100% | 5e-49 | 59% |
| (SEQ ID NO: 105); [PKG1-2] | 262 | 262 | 100% | 6e-96 | 100% |
| (SEQ ID NO: 106); [PKA6] | 210 | 210 | 100% | 2e-75 | 77% |
| (SEQ ID NO: 107); [PKA11] | 251 | 251 | 100% | 1e-91 | 96% |
| (SEQ ID NO: 108); [PKC1] | 231 | 231 | 100% | 2e-83 | 86% |
| (SEQ ID NO: 109); [PKD8] | 145 | 145 | 100% | 9e-50 | 57% |

Comparison of (SEQ ID NO: 106) PKA6 with other sdAbs

| Description | Max score | Total score | Query cover | E value | Max ident |
|---|---|---|---|---|---|
| (SEQ ID NO: 93); [PKE2] | 210 | 210 | 100% | 4e-75 | 78% |
| (SEQ ID NO: 94); [PKF8] | 209 | 209 | 100% | 6e-75 | 77% |
| (SEQ ID NO: 95); [PKF1] | 216 | 216 | 100% | 1e-77 | 80% |
| (SEQ ID NO: 96); [PKG1] | 224 | 224 | 100% | 6e-81 | 83% |
| (SEQ ID NO: 97); [P1.70] | 169 | 169 | 100% | 5e-59 | 65% |
| (SEQ ID NO: 98); [PKE1] | 174 | 174 | 100% | 5e-61 | 70% |
| (SEQ ID NO: 99); [P2.57] | 173 | 173 | 100% | 9e-61 | 69% |
| (SEQ ID NO: 100); [P2.55] | 161 | 161 | 100% | 2e-56 | 66% |
| (SEQ ID NO: 101); [P1.40] | 169 | 169 | 100% | 3e-59 | 65% |
| (SEQ ID NO: 102); [PKE9] | 145 | 145 | 100% | 7e-50 | 62% |
| (SEQ ID NO: 103); [P2.20] | 160 | 160 | 100% | 1e-55 | 65% |
| (SEQ ID NO: 104); [PKC2] | 153 | 153 | 100% | 4e-53 | 64% |
| (SEQ ID NO: 105); [PKG1-2] | 210 | 210 | 100% | 2e-75 | 77% |
| (SEQ ID NO: 106); [PKA6] | 261 | 261 | 100% | 2e-95 | 100% |
| (SEQ ID NO: 107); [PKA11] | 221 | 221 | 100% | 2e-79 | 80% |
| (SEQ ID NO: 108); [PKC1] | 216 | 216 | 100% | 7e-78 | 83% |
| (SEQ ID NO: 109); [PKD8] | 161 | 161 | 100% | 5e-56 | 63% |

Figure 3E (continued)

Comparison of (SEQ ID NO: 107) PKA11 with other sdAbs

| Description | Max score | Total score | Query cover | E value | Max ident |
|---|---|---|---|---|---|
| (SEQ ID NO: 93); [PKE2] | 221 | 221 | 100% | 1e-79 | 81% |
| (SEQ ID NO: 94); [PKF8] | 207 | 207 | 100% | 4e-74 | 75% |
| (SEQ ID NO: 95); [PKF1] | 241 | 241 | 100% | 2e-87 | 91% |
| (SEQ ID NO: 96); [PKG1] | 258 | 258 | 100% | 4e-94 | 98% |
| (SEQ ID NO: 97); [P1.70] | 171 | 171 | 100% | 7e-60 | 67% |
| (SEQ ID NO: 98); [PKE1] | 167 | 167 | 100% | 1e-58 | 69% |
| (SEQ ID NO: 99); [P2.57] | 166 | 166 | 100% | 6e-58 | 66% |
| (SEQ ID NO: 100); [P2.55] | 162 | 162 | 100% | 1e-56 | 66% |
| (SEQ ID NO: 101); [P1.40] | 171 | 171 | 100% | 5e-60 | 67% |
| (SEQ ID NO: 102); [PKE9] | 138 | 138 | 100% | 3e-47 | 60% |
| (SEQ ID NO: 103); [P2.20] | 160 | 160 | 100% | 7e-56 | 65% |
| (SEQ ID NO: 104); [PKC2] | 146 | 146 | 100% | 2e-50 | 60% |
| (SEQ ID NO: 105); [PKG1-2] | 251 | 251 | 100% | 1e-91 | 96% |
| (SEQ ID NO: 106); [PKA6] | 221 | 221 | 100% | 2e-79 | 80% |
| (SEQ ID NO: 107); [PKA11] | 262 | 262 | 100% | 7e-96 | 100% |
| (SEQ ID NO: 108); [PKC1] | 234 | 234 | 100% | 8e-85 | 88% |
| (SEQ ID NO: 109); [PKD8] | 152 | 152 | 100% | 3e-52 | 60% |

Comparison of (SEQ ID NO: 108) PKC1 with other sdAbs

| Description | Max score | Total score | Query cover | E value | Max ident |
|---|---|---|---|---|---|
| (SEQ ID NO: 93); [PKE2] | 215 | 215 | 100% | 3e-77 | 80% |
| (SEQ ID NO: 94); [PKF8] | 196 | 196 | 100% | 1e-69 | 73% |
| (SEQ ID NO: 95); [PKF1] | 231 | 231 | 100% | 1e-83 | 88% |
| (SEQ ID NO: 96); [PKG1] | 238 | 238 | 100% | 3e-86 | 90% |
| (SEQ ID NO: 97); [P1.70] | 160 | 160 | 100% | 6e-56 | 65% |
| (SEQ ID NO: 98); [PKE1] | 162 | 162 | 100% | 1e-56 | 69% |
| (SEQ ID NO: 99); [P2.57] | 165 | 165 | 100% | 2e-57 | 68% |
| (SEQ ID NO: 100); [P2.55] | 159 | 159 | 100% | 3e-55 | 66% |
| (SEQ ID NO: 101); [P1.40] | 167 | 167 | 100% | 2e-58 | 65% |
| (SEQ ID NO: 102); [PKE9] | 134 | 134 | 100% | 1e-45 | 58% |
| (SEQ ID NO: 103); [P2.20] | 157 | 157 | 100% | 2e-54 | 65% |
| (SEQ ID NO: 104); [PKC2] | 147 | 147 | 100% | 8e-51 | 62% |
| (SEQ ID NO: 105); [PKG1-2] | 231 | 231 | 100% | 2e-83 | 86% |
| (SEQ ID NO: 106); [PKA6] | 216 | 216 | 100% | 7e-78 | 83% |
| (SEQ ID NO: 107); [PKA11] | 234 | 234 | 100% | 8e-85 | 88% |
| (SEQ ID NO: 108); [PKC1] | 263 | 263 | 100% | 3e-96 | 100% |
| (SEQ ID NO: 109); [PKD8] | 155 | 155 | 100% | 1e-53 | 64% |

Figure 3E (continued)

Comparison of (SEQ ID NO: 109) PKD8 with other sdAbs

| Description | Max score | Total score | Query cover | E value | Max ident |
|---|---|---|---|---|---|
| (SEQ ID NO: 93); [PKE2] | 164 | 164 | 100% | 4e-57 | 63% |
| (SEQ ID NO: 94); [PKF8] | 158 | 158 | 100% | 8e-55 | 60% |
| (SEQ ID NO: 95); [PKF1] | 157 | 157 | 100% | 1e-54 | 62% |
| (SEQ ID NO: 96); [PKG1] | 155 | 155 | 100% | 9e-54 | 62% |
| (SEQ ID NO: 97); [P1.70] | 167 | 167 | 100% | 2e-58 | 65% |
| (SEQ ID NO: 98); [PKE1] | 171 | 171 | 100% | 7e-60 | 67% |
| (SEQ ID NO: 99); [P2.57] | 171 | 171 | 100% | 4e-60 | 67% |
| (SEQ ID NO: 100); [P2.55] | 165 | 165 | 100% | 1e-57 | 67% |
| (SEQ ID NO: 101); [P1.40] | 159 | 159 | 100% | 2e-55 | 63% |
| (SEQ ID NO: 102); [PKE9] | 142 | 142 | 100% | 9e-49 | 57% |
| (SEQ ID NO: 103); [P2.20] | 166 | 166 | 100% | 5e-58 | 66% |
| (SEQ ID NO: 104); [PKC2] | 149 | 149 | 100% | 2e-51 | 62% |
| (SEQ ID NO: 105); [PKG1-2] | 145 | 145 | 100% | 9e-50 | 57% |
| (SEQ ID NO: 106); [PKA6] | 161 | 161 | 100% | 5e-56 | 63% |
| (SEQ ID NO: 107); [PKA11] | 152 | 152 | 100% | 3e-52 | 60% |
| (SEQ ID NO: 108); [PKC1] | 155 | 155 | 100% | 1e-53 | 64% |
| (SEQ ID NO: 109); [PKD8] | 276 | 276 | 100% | 5e-101 | 100% |

Figure 3E (continued)

| | | | | | | | | | |
|---|---|---|---|---|---|---|---|---|---|
| H1 | H2 | H3 | H4 | H5 | H6 | H7 | H8 | H9 | H10 |
| Q | V | K | L | E | E | S | G | G | G |
| H11 | H12 | H13 | H14 | H15 | H16 | H17 | H18 | H19 | H20 |
| L | V | Q | A | G | G | S | L | R | L |
| H21 | H22 | H23 | H24 | H25 | H26 | H27 | H28 | H29 | H30 |
| S | C | V | A | S | G | R | T | I | N |
| H31 | H32 | H33 | H34 | H35 | H36 | H37 | H38 | H39 | H40 |
| D | Y | I | L | G | W | F | R | Q | A |
| H41 | H42 | H43 | H44 | H45 | H46 | H47 | H48 | H49 | H50 |
| P | G | K | K | R | E | F | V | A | A |
| H51 | H52 | H52A | H52B | H52C | H52D | H52E | H52F | H52G | H53 |
| I | R | G | S | G | A | I | R | G | R |
| H54 | H55 | H56 | H57 | H58 | H59 | H60 | H61 | H62 | H63 |
| E | G | S | T | F | Y | V | D | S | V |
| H64 | H65 | H66 | H67 | H68 | H69 | H70 | H71 | H72 | H73 |
| K | G | R | Y | T | I | S | K | D | N |
| H74 | H75 | H76 | H77 | H78 | H79 | H80 | H81 | H82 | H82A |
| A | K | N | T | V | D | L | Q | M | N |
| H82B | H82C | H83 | H84 | H85 | H86 | H87 | H88 | H89 | H90 |
| S | L | K | P | E | D | S | A | T | Y |
| H91 | H92 | H93 | H94 | H95 | H96 | H97 | H98 | H99 | H100 |
| Y | C | A | V | D | R | F | P | T | P |
| H100A | H100B | H100C | H100D | H100E | H100F | H100G | H100H | H100I | H101 |
| E | F | S | T | Q | V | G | H | Y | D |
| H102 | H103 | H104 | H105 | H106 | H107 | H108 | H109 | H110 | H111 |
| Y | W | G | Q | G | T | Q | V | T | V |
| H112 | H113 | | | | | | | | |
| S | S | | | | | | | | |

Figure 5

| HepG2 cells | | | HuH 7 cells | |
| --- | --- | --- | --- | --- |
| S.No. | Antibody | LDLR expression (fold) | Antibody | LDLR expression (fold) |
| 1 | P 1.70 | 1.8 | P2.20 | 1.7 |
| 2 | P 2.57 | 2.5 | PKC2 | 1.5 |
| 3 | P 2.55 | 2.0 | PKF8 | 1.7 |
| 4 | P 1.33 | 2.1 | PKG1 | 1.5 |
| 5 | P 1.40 | 1.9 | PKF8 | 50% (FACS) |
| 6 | PKE1 | 2.1 | | |
| 7 | PKE2 | 2.4 | | |
| 8 | PKE9 | 2.3 | | |
| 9 | PKF1 | 2.8 | | |
| 10 | PKF8 | 1.7 | | |
| 11 | PKG1 | 1.5 | | |

SINGLE DOMAIN ANTIBODIES AS INHIBITORS OF PCSK9

CROSS-REFERENCE TO RELATED APPLICATIONS

This application is a National Entry Application of PCT application no PCT/CA2012/050923* filed on Dec. 20, 2012 and published in English under PCT Article 21(2), which itself claims benefit of U.S. provisional application Ser. No. 61/578,000, filed on 20 Dec. 2011. All documents above are incorporated herein in their entirety by reference.

TECHNICAL FIELD

The present invention generally relates to cardiovascular disorders, and more specifically to the decrease of circulating levels of low-density lipoprotein-cholesterol (LDL-C).

REFERENCE TO SEQUENCE LISTING

Pursuant to 37 C.F.R. 1.821(c), a sequence listing is submitted herewith as an ASCII compliant text file named 12810_458_ST25.TXT, created on Dec. 19, 2012 and having a size of 92 Kb kilobytes. The content of the aforementioned file is hereby incorporated by reference in its entirety.

BACKGROUND ART

Complications resulting from cardiovascular disorders are the main cause of death worldwide, affecting ~13 million individuals/year, as compared to ~6 million/year due to various forms of cancer. One of the most potent cardiovascular risk factors is elevated levels of LDL-C. The incidence of cardiovascular pathologies is expected to increase dramatically in the next two decades. Clinical trial data has demonstrated that reductions in LDL cholesterol levels are related to the rate of coronary events (Law et al., 2003 *BMJ* 326:1423-1427). Moderate lifelong reduction in plasma LDL cholesterol levels has been shown to be substantially correlated with a significant reduction in the incidence of coronary events (Cohen et al., *N. Engl. J. Med.* 354:1264-1272), even in populations with a high prevalence of non-lipid-related cardiovascular risk factors. Accordingly, there is great benefit to be gained from the managed control of LDL cholesterol levels. Among important cholesterol-lowering drugs are statins (Briel, M., Nordmann, A. J., and Bucher, H. C. *Curr. Opin. Lipidol.*, 16: 601-605, 2005). Though well tolerated by the majority of patients, adverse side effects are being compiled (https://www.statineffects.com/info/). The combination of statins with ezetimibe, an intestinal sterol transporter blocker, further reduces LDL-C by ≤20%.

Thus, there is a need for the development of efficient strategies to decrease levels of circulating LDL-C (Brown, M. S, and Goldstein, J. L. *Science,* 311: 1721-1723, 2006; Tall, A. R. *N. Engl. J Med.,* 354: 1310-1312, 2006).

The present description refers to a number of documents, the content of which is herein incorporated by reference in their entirety.

SUMMARY OF THE INVENTION

In a first aspect, the present invention provides an antibody specifically binding to human PCSK9, said antibody comprising:

(i) a complementary determining region (CDR) 1 region comprising an amino acid sequence of formula I:

$$X1-X2-X3-X4-X5 \quad (I) \qquad \text{(SEQ ID NO: 1)}$$

wherein
X1 is D, N, H, V, A, I or S;
X2 is Y, P or A;
X3 is I, A, T, V or Y;
X4 is L, V, T or M; and
X5 is G, S or A;
or a sequence substantially identical thereto;

(ii) a CDR2 region comprising an amino acid sequence of formula II:

$$Z1-Z2-Z3-Z4-Z5-Z6-Z7-Z8-Z9-Z10-Z11-Z12-Z13-Z14-Z15-Z16-Y-Z17-Z18-Z19-Z20-Z21-G \quad (II)$$
(SEQ ID NO: 2)

wherein
Z1 is A, Q, T, G or S;
Z2 is I, V or A;
Z3 is R, T, A or S;
Z4 is G, E, S, Q, A or D;
Z5 is S, P, V, R, H or G;
Z6 is G, A or D;
Z7 is A, S, D, G or T;
Z8 is I, V or is absent;
Z9 is R, T or is absent;
Z10 is G, A or is absent;
Z11 is R, D or is absent;
Z12 is E, V or is absent;
Z13 is G, E or is absent;
Z14 is S, R, F or is absent;
Z15 is T, I or S;
Z16 is F, Y, E, D, P, A or N;
Z17 is V, A, S, E or T;
Z18 is D, H, N, E, R or V;
Z19 is S, N or F;
Z20 is V or A; and
Z21 is K or R; or a sequence substantially identical thereto; and/or (iii) a CDR3 region comprising an amino acid sequence of formula III:

$$B1-B2-B3-B4-B5-B6-B7-B8-B9-B10-B11-B12-B13-B14-B14-B15-B16-B17-B18 \text{ (SEQ ID NO: 3)} \quad (III)$$

wherein
B1 is D, T, A, P, R or Y;
B2 is R, Q, K, T, L, Y, P, A or S;
B3 is F, Y, S, R, A, G or M;
B4 is P, G, Y, S, F or is absent;
B5 is T, N, S, Y or is absent;
B6 is P, Y, T, I, G, R or is absent;
B7 is E, N, R, D, T or is absent;
B8 is F, Y, L, I, V or is absent;
B9 is S, T, M, P, Y or is absent;
B10 is T, G, D, H or S;
B11 is Q, P, T, A, R, H, V or E;
B12 is V, D, L, H, S, F or T;
B13 is G, P, L, H, R, S or M, in a specific embodiment, B13 is G, P, L, R, S or M, B14 is K, N, E, W, V or is absent;
B15 is H, K, E, T, G, N or S;
B16 is Y, S or Q;
B17 is D, H, V, E, A or is absent; and
B18 is Y, L, H, V or is absent;
or a sequence substantially identical thereto.

In another embodiment, the above-mentioned CDR1 region comprises one of the following amino acid sequences: DYILG (SEQ ID NO: 4), NYIVG (SEQ ID NO: 5), HYILG (SEQ ID NO: 6), VYAMG (SEQ ID NO: 7), DYAMG (SEQ ID NO: 8), NYAMG (SEQ ID NO: 9), AYAMG (SEQ ID NO: 10), IAYMA (SEQ ID NO: 11), SPTMA (SEQ ID NO: 12), HYIVG (SEQ ID NO: 13), HYVTS (SEQ ID NO: 14) or a sequence substantially identical thereto.

In an embodiment, the above-mentioned CDR2 region comprises one of the following amino acid sequences: AIRGSGAIRGREGSTFYVDSVKG (SEQ ID NO: 15), AIRGSGAIRGREGSTYYADSVKG (SEQ ID NO: 16), AIRESGSSTYYADSVKG (SEQ ID NO: 17), AITSPGDSIPYAHSVKG (SEQ ID NO: 18), AITSSGDSIPYAHSVKG (SEQ ID NO: 19), AAAQSGDSSAYARSVKG (SEQ ID NO: 20), QISQVDGFTYYEDSVKG (SEQ ID NO: 21), TIRDSDASIYYTDSVKG (SEQ ID NO: 22), SISSGGTTNYAVFAKG (SEQ ID NO: 23), AIRSRDDSTYYSNSVKG (SEQ ID NO: 24), AIRESGSRTYYADSVRG (SEQ ID NO: 25), AVRESGSSTEYAENVKG (SEQ ID NO: 26), AVREPGSSTYYADSVKG (SEQ ID NO: 27), GVTAHAGVTADVESTDYSDSVKG (SEQ ID NO: 28), or a sequence substantially identical thereto. In an embodiment, the above-mentioned CDR3 region comprises one of the following amino acid sequences: DRFPTPEFSTQVGHYDY (SEQ ID NO: 29), DRFPTPEFTTQVGHYDV (SEQ ID NO: 30), DQYPTPEFSTQVGHYDY (SEQ ID NO: 31), TKSGNYNYMGPDPKKYHY (SEQ ID NO: 32), TTSGTYNYMGPDPKEYVY (SEQ ID NO: 33), TTRGSYEYMGPDPKKYEY (SEQ ID NO: 34), ALAFPTTSSNTYAY (SEQ ID NO: 35), RQYYSGRVYSTFREEYDY (SEQ ID NO: 36), YAMSTETMVSQDY (SEQ ID NO: 37), TYSGTYNYMGADPKEYVY (SEQ ID NO: 38), DPRTIDLSSRLLWGS (SEQ ID NO: 39), DQYPTEFSTQVGHYDY (SEQ ID NO: 40), DRFPTPEFSDRVGHYDL (SEQ ID NO: 41), DPYPTPEFTTHVGHYDY (SEQ ID NO: 42), PSGFYRTIPHVHSNYDH (SEQ ID NO: 43) or a sequence substantially identical thereto.

In an embodiment, the above-mentioned CDR1, CDR2 and CDR3 regions respectively comprise: DYILG (SEQ ID NO: 4), AIRGSGAIRGREGSTFYVDSVKG (SEQ ID NO: 15) and DRFPTPEFSTQVGHYDY (SEQ ID NO: 29), or sequences substantially identical thereto.

In an embodiment, the above-mentioned CDR1, CDR2 and CDR3 regions respectively comprise: NYIVG (SEQ ID NO: 5), AIRGSGAIRGREGSTYYADSVKG (SEQ ID NO: 16) and DRFPTPEFTTQVGHYDV (SEQ ID NO: 30), or sequences substantially identical thereto.

In an embodiment, the above-mentioned CDR1, CDR2 and CDR3 regions respectively comprise: DYILG (SEQ ID NO: 4), AIRESGSSTYYADSVKG (SEQ ID NO: 17) and DQYPTPEFSTQVGHYDY (SEQ ID NO: 31), or sequences substantially identical thereto.

In an embodiment, the above-mentioned CDR1, CDR2 and CDR3 regions respectively comprise: HYILG (SEQ ID NO: 6), AIRESGSSTYYADSVKG (SEQ ID NO: 17) and DQYPTPEFSTQVGHYDY (SEQ ID NO: 31), or sequences substantially identical thereto.

In an embodiment, the above-mentioned CDR1, CDR2 and CDR3 regions respectively comprise: VYAMG (SEQ ID NO: 7), AITSPGDSIPYAHSVKG (SEQ ID NO: 18) and TKSGNYNYMGPDPKKYHY (SEQ ID NO: 32), or sequences substantially identical thereto.

In an embodiment, the above-mentioned CDR1, CDR2 and CDR3 regions respectively comprise: VYAMG (SEQ ID NO: 7), AITSSGDSIPYAHSVKG (SEQ ID NO: 19) and TTSGTYNYMGPDPKEYVY (SEQ ID NO: 33), or sequences substantially identical thereto.

In an embodiment, the above-mentioned CDR1, CDR2 and CDR3 regions respectively comprise: DYAMG (SEQ ID NO: 8), AAAQSGDSSAYARSVKG (SEQ ID NO: 20) and TTRGSYEYMGPDPKKYEY (SEQ ID NO: 34), or sequences substantially identical thereto.

In an embodiment, the above-mentioned CDR1, CDR2 and CDR3 regions respectively comprise: NYAMG (SEQ ID NO: 9), QISQVDGFTYYEDSVKG (SEQ ID NO: 21) and ALAFPTTSSNTYAY (SEQ ID NO: 35), or sequences substantially identical thereto.

In an embodiment, the above-mentioned CDR1, CDR2 and CDR3 regions respectively comprise: AYAMG (SEQ ID NO: 10), TIRDSDASIYYTDSVKG (SEQ ID NO: 22) and RQYYSGRVYSTFREEYDY (SEQ ID NO: 36), or sequences substantially identical thereto.

In an embodiment, the above-mentioned CDR1, CDR2 and CDR3 regions respectively comprise: IAYMA (SEQ ID NO: 11), SISSGGTTNYAVFAKG (SEQ ID NO: 23) and YAMSTETMVSQDY (SEQ ID NO: 37), or sequences substantially identical thereto.

In an embodiment, the above-mentioned CDR1, CDR2 and CDR3 regions respectively comprise: NYAMG (SEQ ID NO: 9), QISQVDGFTYYEDSVKG (SEQ ID NO: 21) and TYSGTYNYMGADPKEYVY (SEQ ID NO: 38), or sequences substantially identical thereto.

In an embodiment, the above-mentioned CDR1, CDR2 and CDR3 regions respectively comprise: SPTMA (SEQ ID NO: 12), AIRSRDDSTYYSNSVKG (SEQ ID NO: 24) and DPRTIDLSSRLLWGS (SEQ ID NO: 39), or sequences substantially identical thereto.

In an embodiment, the above-mentioned CDR1, CDR2 and CDR3 regions respectively comprise: HYILG (SEQ ID NO: 6), AIRESGSRTYYADSVRG (SEQ ID NO: 25) and DQYPTTEFSTQVGHYDY (SEQ ID NO: 40), or sequences substantially identical thereto.

In an embodiment, the above-mentioned CDR1, CDR2 and CDR3 regions respectively comprise: HYIVG (SEQ ID NO: 13), AVRESGSSTEYAENVKG (SEQ ID NO: 26) and DRFPTPEFSDRVGHYDL (SEQ ID NO: 41), or sequences substantially identical thereto.

In an embodiment, the above-mentioned CDR1, CDR2 and CDR3 regions respectively comprise: HYILG (SEQ ID NO: 6), AIRESGSRTYYADSVRG (SEQ ID NO: 25) and DQYPTPEFSTQVGHYDY (SEQ ID NO: 31), or sequences substantially identical thereto.

In an embodiment, the above-mentioned CDR1, CDR2 and CDR3 regions respectively comprise: HYILG (SEQ ID NO: 6), AVREPGSSTYYADSVKG (SEQ ID NO: 27) and DPYPTPEFTTHVGHYDY (SEQ ID NO: 42), or sequences substantially identical thereto.

In an embodiment, the above-mentioned CDR1, CDR2 and CDR3 regions respectively comprise: HYVTS (SEQ ID NO: 14), GVTAHAGVTADVESTDYSDSVKG (SEQ ID NO: 28) and PSGFYRTIPHVHSNYDH (SEQ ID NO: 43), or sequences substantially identical thereto.

In another embodiment, the above-mentioned antibody further comprises a framework region (FR) 1 comprising an amino acid sequence of formula IV:

(SEQ ID NO: 44)
Q-V-X6-L-X7-E-S-G-G-G-X8-V-Q-A-G-X9-S-X10-R-L-S-C-X11-X12-X13-X14-X15-X16-X17-X18 (IV)

wherein
X6 is K or Q;
X7 is E or V;
X8 is L or P;
X9 is G or D
X10 is L or M;
X11 is V, L, S, or A;
X12 is A or P;
X13 is S or P;
X14 is G, D or R;
X15 is R, L or S;
X16 is T, F, I or G;
X17 is I, V, P or F; and
X18 is N, R, S or V
or a sequence substantially identical thereto.

In an embodiment, X6 is K; X7 is E; X8 is L; X9 is G; X10 is L; X11 is A; X12 is A; X13 is S; X14 is G; X15 is R; X16 is T; X17 is F; and/or X18 is N.

In a further embodiment, the above-mentioned FR1 comprises one of the following amino acid sequences:

(SEQ ID NO: 45)
QVKLEESGGGLVQAGGSLRLSCVASGRTIN, (SEQ ID NO: 46)
QVQLVESGGGLVQAGGSLRLSCLASDRTVN, (SEQ ID NO: 47)
QVQLVESGGGLVQAGGSLRLSCAASGRTPR, (SEQ ID NO: 48)
QVQLVESGGGLVQAGGSLRLSCAASGRTFS, (SEQ ID NO: 49)
QVKLEESGGGLVQAGGSLRLSCAASGRTFS, (SEQ ID NO: 50)
QVKLEESGGGLVQAGGSLRLSCAASGRTFN, (SEQ ID NO: 51)
QVKLEESGGGLVQAGGSLRLSCAASGLTFS, (SEQ ID NO: 52)
QVKLEESGGGLVQAGGSLRLSCSPSDRTFS, (SEQ ID NO: 53)
QVKLEESGGGLVQAGGSLRLSCAAPRSGVV, (SEQ ID NO: 54)
QVKLEESGGGPVQAGGSLRLSCLASGRFVN, (SEQ ID NO: 55)
QVQLVESGGGLVQAGGSMRLSCAASGRTPR, (SEQ ID NO: 56)
QVKLEESGGGLVQAGGSLRLSCAASGRTPR, (SEQ ID NO: 57)
QVKLEESGGGLVQAGDSLRLSCAASGRIFN, or a sequence substantially identical thereto.

In another embodiment, the above-mentioned antibody further comprises an FR2 comprising an amino acid sequence of formula V:

(SEQ ID NO: 58)
X19-X20-R-Q-X21-P-X22-X23-X24-X25-X26-X27-V-X28 (V)

wherein
X19 is W or Y;
X20 is F or Y;
X21 is A or V;
X22 is G, D or E;
X23 is K, T, R, A, E or Q;
X24 is K, E, Q or L;
X25 is R or P;
X26 is E or K;
X27 is F or L; and
X28 is A, T or G,
or a sequence substantially identical thereto.

In an embodiment, X19 is W; X20 is F; X21 is A; X22 is G; X23 is K; X24 is E; X25 is R; X26 is E; X27 is F; and/or X28 is A.

In an embodiment, the above-mentioned FR2 comprises one of the following amino acid sequences:

(SEQ ID NO: 59)
WFRQAPGKKREFVA, (SEQ ID NO: 60)
YFRQAPGKEREFVA, (SEQ ID NO: 61)
WFRQAPGKQREFVA, (SEQ ID NO: 62)
WFRQAPGKEREFVA, (SEQ ID NO: 63)
WFRQAPGKEREFVT, (SEQ ID NO: 64)
WFRQAPGTEREFVG, (SEQ ID NO: 65)
WFRQVPGREREFVA, (SEQ ID NO: 66)
WYRQAPEKQRELVA, (SEQ ID NO: 67)
WFRQAPGAEREFVG, (SEQ ID NO: 68)
WFRQAPGEERKFVA, (SEQ ID NO: 69)
WFRQAPGKLPEFVA, (SEQ ID NO: 70)
WFRQAPDQEREFVA, or a sequence substantially identical thereto.

In another embodiment, the above-mentioned antibody further comprises an FR3 comprising an amino acid sequence of formula VI:

(SEQ ID NO: 71)
R-X29-X30-X31-S-X32-X33-X34-X35-K-X36-X37-X38-X39-L-X40-M-X41-S-L-X42-P-X43-D-X44-A-X45-Y-X46-C-X47-X48 (VI)

wherein
X29 is Y, F or D;
X30 is T, S or V;

X31 is I or V;
X32 is K, R, A or L;
X33 is D or N;
X34 is N, G, H or Y;
X35 is A, T, V or S;
X36 is N or S;
X37 is T or A;
X38 is V, I, L, A or G;
X39 is Y, D or F;
X40 is Q or R;
X41 is N, D or S;
X42 is K, I or Q;
X43 is E or D;
X44 is S or T;
X45 is T, V or A;
X46 is Y or I;
X47 is A or N; and
X48 is A, V, L or G,
or a sequence substantially identical thereto.

In an embodiment, X29 is F; X30 is T; X31 is I; X32 is R; X33 is D; X34 is N; X35 is A; X36 is N; X37 is T; X38 is V; X39 is Y; X40 is Q; X41 is N; X42 is K; X43 is E; X44 is T; X45 is V; X46 is Y; X47 is A; and/or X48 is A.

In an embodiment, the above-mentioned FR3 comprises one of the following amino acid sequences:

```
                                      (SEQ ID NO: 72)
RYTISKDNAKNTVDLQMNSLKPEDSATYYCAV, (SEQ ID NO: 73)
RFSISKDNAKNTIYLQMNSLKPEDSAVYYCAL, (SEQ ID NO: 74)
RYTISRNNTKNAVDLQMNSLKPEDSATYYCAV, (SEQ ID NO: 75)
RYTISRDNTKNAVDLQMNSLKPEDSATYYCAV, (SEQ ID NO: 76)
RFTISRDNAKNTLYLQMNSLKPEDTAAYYCAA, (SEQ ID NO: 77)
RFTISRDNAKNTVYLQMNSLKPEDTAAYYCAA, (SEQ ID NO: 78)
RFTISRDGAKNTAYLQMDSLKPEDTAAYYCAA, (SEQ ID NO: 79)
RFTISRDNAKNTVYLQMNSLKPDDTAVYYCAA, (SEQ ID NO: 80)
RFTISRDNAKNTVYLQMNSLIPDDTAVYYCAA, (SEQ ID NO: 81)
RFTISADNAKNTVYLQMNSLKPEDTAVYICNA, (SEQ ID NO: 82)
RFTISRDNAKNTVYLQMSSLKPDDTAVYYCAA, (SEQ ID NO: 83)
RFTISLDNAKNTAYLRMDSLQPEDTAVYYCAG, (SEQ ID NO: 84)
RDTISRDNTKNAGDLQMNSLKPEDSATYYCAV, (SEQ ID NO: 85)
RFVISKDNVKSTVFLQMNSLKPEDSAVYYCAL, (SEQ ID NO: 86)
RDTISKDHTKNAVDLQMNSLKPEDSATYYCAV, (SEQ ID NO: 87)
RFTVSRDYSKNTVYLQMNSLKPEDTAVYYCAA,
```
or a sequence substantially identical thereto.

In another embodiment, the above-mentioned antibody further comprises an FR4 comprising an amino acid sequence of formula VII:

```
                                      (SEQ ID NO: 88)
X49-G-X50-G-T-X51-V-T-X52-S-S    (VII)
``` wherein
X49 is W or S;
X50 is R or Q;
X51 is Q or E; and
X52 is V or I,
or a sequence substantially identical thereto.

In an embodiment, X49 is W; X50 is Q; X51 is Q; and/or X52 is V, or a sequence substantially identical thereto.

In an embodiment, the above-mentioned FR4 comprises one of the following amino acid sequences: WGQGTQVTVSS (SEQ ID NO: 89), WGRGTQVTVSS (SEQ ID NO: 90), SGQGTQVTVSS (SEQ ID NO: 91), WGQGTEVTISS (SEQ ID NO: 92), or a sequence substantially identical thereto.

In an embodiment, the above-mentioned antibody comprises, or consists of, one of the following amino acid sequences:

```
                                      (SEQ ID NO: 93)
QVKLEESGGGLVQAGGSLRLSCVASGRTINDYILGWFRQAPGKKREFV

AAIRGSGAIRGREGSTFYVDSVKGRYTISKDNAKNTVDLQMNSLKPED

SATYYCAVDRFPTPEFSTQVGHYDYWGQGTQVTVSS;

(SEQ ID NO: 94)
QVQLVESGGGLVQAGGSLRLSCLASDRTVNNYIVGYFRQAPGKEREFV

AAIRGSGAIRGREGSTYYADSVKGRFSISKDNAKNTIYLQMNSLKPED

SAVYYCALDRFPTPEFTTQVGHYDVWGRGTQVTVSS;

(SEQ ID NO: 95)
QVKLEESGGGLVQAGGSLRLSCVASGRTINDYILGWFRQAPGKKREFV

AAIRESGSSTYYADSVKGRYTISRNNTKNAVDLQMNSLKPEDSATYYC

AVDQYPTPEFSTQVGHYDYWGQGTQVTVSS;

(SEQ ID NO: 96)
QVQLVESGGGLVQAGGSLRLSCAASGRTPRHYILGWFRQAPGKQREFV

AAIRESGSSTYYADSVKGRYTISRDNTKNAVDLQMNSLKPEDSATYYC

AVDQYPTPEFSTQVGHYDYWGQGTQVTVSS;

(SEQ ID NO: 97)
QVQLVESGGGLVQAGGSLRLSCAASGRTFSVYAMGWFRQAPGKEREFV

AAITSPGDSIPYAHSVKGRFTISRDNAKNTLYLQMNSLKPEDTAAYYC

AATKSGNYNYMGPDPKKYHYWGQGTQVTVSS;

(SEQ ID NO: 98)
QVKLEESGGGLVQAGGSLRLSCAASGRTFSVYAMGWFRQAPGKEREFV

TAITSSGDSIPYAHSVKGRFTISRDNAKNTVYLQMNSLKPEDTAAYYC

AATTSGTYNYMGPDPKEYVYWGQGTQVTVSS;

(SEQ ID NO: 99)
QVKLEESGGGLVQAGGSLRLSCAASGRTFNDYAMGWFRQAPGKEREFV

AAAAQSGDSSAYARSVKGRFTISRDGAKNTAYLQMDSLKPEDTAAYYC

AATTRGSYEYMGPDPKKYEYWGQGTQVTVSS;
```

-continued (SEQ ID NO: 100)
QVKLEESGGGLVQAGGSLRLSCAASGLTFSNYAMGWFRQAPGTEREFV

GQISQVDGFTYYEDSVKGRFTISRDNAKNTVYLQMNSLKPDDTAVYYC

AAALAFPTTSSNTYAYSGQGTQVTVSS;

(SEQ ID NO: 101)
QVKLEESGGGLVQAGGSLRLSCSPSDRTFSAYAMGWFRQVPGREREFV

ATIRDSDASIYYTDSVKGRFTISRDNAKNTVYLQMNSLIPDDTAVYYC

AARQYYSGRVYSTFREEYDYWGQGTQVTVSS;

(SEQ ID NO: 102)
QVKLEESGGGLVQAGGSLRLSCAAPRSGVVIAYMAWYRQAPEKQRELV

ASISSGGTTNYAVFAKGRFTISADNAKNTVYLQMNSLKPEDTAVYICN

AYAMSTETMVSQDYWGQGTQVTVSS;

(SEQ ID NO: 103)
QVKLEESGGGLVQAGGSLRLSCAASGLTFSNYAMGWFRQAPGAEREFV

GQISQVDGFTYYEDSVKGRFTISRDNAKNTVYLQMSSLKPDDTAVYYC

AATYSGTYNYMGADPKEYVYWGQGTQVTVSS;

(SEQ ID NO: 104)
QVKLEESGGGPVQAGGSLRLSCLASGRFVNSPTMAWFRQAPGEERKFV

AAIRSRDDSTYYSNSVKGRFTISLDNAKNTAYLRMDSLQPEDTAVYYC

AGDPRTIDLSSRLLWGSWGQGTQVTVSS;

(SEQ ID NO: 105)
QVQLVESGGGLVQAGGSMRLSCAASGRTPRHYILGWFRQAPGKQREFV

AAIRESGSRTYYADSVRGRDTISRDNTKNAGDLQMNSLKPEDSATYYC

AVDQYPTTEFSTQVGHYDYWGQGTEVTISS;

(SEQ ID NO: 106)
QVKLEESGGGLVQAGGSLRLSCAASGRTPRHYIVGWFRQAPGKEREFV

AAVRESGSSTEYAENVKGRFVISKDNVKSTVFLQMNSLKPEDSAVYYC

ALDRFPTPEFSDRVGHYDLWGQGTQVTVSS;

(SEQ ID NO: 107)
QVQLVESGGGLVQAGGSMRLSCAASGRTPRHYILGWFRQAPGKQREFV

AAIRESGSRTYYADSVRGRYTISRDNTKNAVDLQMNSLKPEDSATYYC

AVDQYPTPEFSTQVGHYDYWGQGTQVTVSS;

(SEQ ID NO: 108)
QVKLEESGGGLVQAGGSLRLSCAASGRTPRHYILGWFRQAPGKLPEFV

AAVREPGSSTYYADSVKGRDTISKDHTKNAVDLQMNSLKPEDSATYYC

AVDPYPTPEFTTHVGHYDYWGQGTQVTVSS;

(SEQ ID NO: 109)
QVKLEESGGGLVQAGDSLRLSCAASGRIFNHYVTSWFRQAPDQEREFV

AGVTAHAGVTADVESTDYSDSVKGRFTVSRDYSKNTVYLQMNSLKPED

TAVYYCAAPSGFYRTIPHVHSNYDHWGQGTQVTVSS;

or a sequence substantially identical thereto. For example, an antibody comprising an amino acid sequence having at least 80% sequence identity with one of the above-cited sequences (e.g., sequences 93 to 109) is substantially identical to that sequence. In another embodiment said substantially identical amino acid sequence has at least 80.95% identity with one of the above-cited sequences, in other embodiments, at least 81%, 82%, 83%, 83.46%, 84%, 85%, 86%, 87%, 87.30%, 88%, 89%, 90%, 91, 92%, 93%, 94%, 95%, 96%, 97%, 98% or 99%.

In an embodiment, the above-mentioned antibody is a single domain antibody.

In another aspect, the present invention provides a pharmaceutical composition comprising the above-mentioned antibody. In another aspect, the pharmaceutical composition further comprises at least one other of the above-mentioned antibodies.

In a further embodiment, the pharmaceutical composition further comprises a pharmaceutically acceptable carrier, excipient, and/or diluent.

In another aspect, the present invention provides the above-mentioned antibody or composition for use as a medicament.

In another aspect, the present invention provides the above-mentioned antibody or composition, for the manufacture of a medicament. In an embodiment, the above-mentioned medicament is for preventing or treating hypercholesterolemia in a subject.

In another aspect, the present invention provides a method for preventing or treating hypercholesterolemia comprising administering to a subject in need thereof an effective amount of the above-mentioned antibody or composition.

In another aspect, the present invention provides the use of the above-mentioned antibody or composition, as a medicament.

In another aspect, the present invention provides the use of the above-mentioned antibody or composition, for preventing or treating hypercholesterolemia in a subject.

In another aspect, the present invention provides the use of the above-mentioned antibody or composition, for the manufacture of a medicament for preventing or treating hypercholesterolemia in a subject.

In another aspect, the present invention provides a nucleic acid comprising a nucleotide sequence encoding the above-mentioned antibody.

In another aspect, the present invention provides a vector comprising the above-mentioned nucleic acid.

In another aspect, the present invention provides a cell comprising the above-mentioned nucleic acid or vector.

In another aspect, the present invention provides a kit for preventing or treating hypercholesterolemia in a subject comprising at least two of the above-mentioned antibodies.

In another aspect, the present invention provides a kit for detecting PCSK9 in a biological sample comprising at least two of the above-mentioned antibodies.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 2 shows [A] an amino acid alignment of representative single domain antibody (sdAb) chimeric constructs of the invention, namely PKE2 (SEQ ID NO: 110); PKF8 (SEQ ID NO: 111); PKF1 (SEQ ID NO: 112); PKG1 (SEQ ID NO: 113); P1.70 (SEQ ID NO: 114); PKE1 (SEQ ID NO: 115); P2.57 (SEQ ID NO: 116); P2.55 (SEQ ID NO: 117); P1.40 (SEQ ID NO: 118); and PKE9 (SEQ ID NO: 119). The first 30 residues correspond to the signal peptide sequence of human PCSK9. The V5 tag is bold and underlined. The last 6 residues correspond to a hexahistidine tag; in P2.55 and P2.57 the hexahistidine tag is preceded by a 10 amino acid c-Myc tag and one linker residue. [B] Amino acid sequences of other representative single domain antibody chimeric constructs of the invention, namely P2.20 (SEQ ID NO: 120); PKC2 (SEQ ID NO: 121); PKG1-2 (SEQ ID NO: 122); PKA6 (SEQ ID NO: 123); PKA11 (SEQ ID NO: 124); PKC1 (SEQ ID NO: 125); and PKD8 (SEQ ID NO: 126);

FIG. 3 shows an alignment of the sequences corresponding to the single domain antibodies depicted in [A] FIG. 2A, namely PKE2 (SEQ ID NO: 127); PKF8 (SEQ ID NO: 128); PKF1 (SEQ ID NO: 129); PKG1 (SEQ ID NO: 130); P1.70 (SEQ ID NO: 131); PKE1 (SEQ ID NO: 132); P2.57 (SEQ ID NO: 133); P2.55 (SEQ ID NO: 134); P1.40 (SEQ ID NO: 135); PKE9 (SEQ ID NO: 136); [B] FIG. 2B, namely P2.20 (SEQ ID NO: 137); PKC2 (SEQ ID NO: 138); PKG1-2 (SEQ ID NO: 139); PKA6 (SEQ ID NO: 140); PKA11 (SEQ ID NO: 141); PKC1 (SEQ ID NO: 142); and PKD8 (SEQ ID NO: 143); or [C] all sequences shown in [A] and [B], with the regions corresponding to the complementary determining regions (CDRs) and framework regions (FRs) indicated. [D] presents three alignments and corresponding sequence identity percentages for subgroups of sdABs fragments (i.e. containing the CDRs and FR regions), namely 1) PKG1-2 (SEQ ID NO: 105), PKA11 (SEQ ID NO: 107), PKG1 (SEQ ID NO: 96), PKF1 (SEQ ID NO: 95) and PKC1 (SEQ ID NO: 108); 2) P1.70 (SEQ ID NO: 97), PKE1 (SEQ ID NO: 98) and P2.57 (SEQ ID NO: 99); and 3) PKG1-2 (SEQ ID NO: 105), PKA11 (SEQ ID NO: 107), PKG1 (SEQ ID NO: 96) and PKF1 (SEQ ID NO: 95); and [E] presents sequence identity percentages calculated with a Blast™ Basic Local Alignment Search Tool for each pair of 17 sdABs fragments (i.e. all CDRS and FR regions). Each of the 17 tables presents a comparison of the sequence of a specific sdAB fragment with that of the 16 others;

FIG. 5 shows the Kabat numbering of the sequence identified herein as "PKE2" (SEQ ID NO: 93), using the Abnum antibody amino acid numbering tool;

DISCLOSURE OF INVENTION

Figure 1:
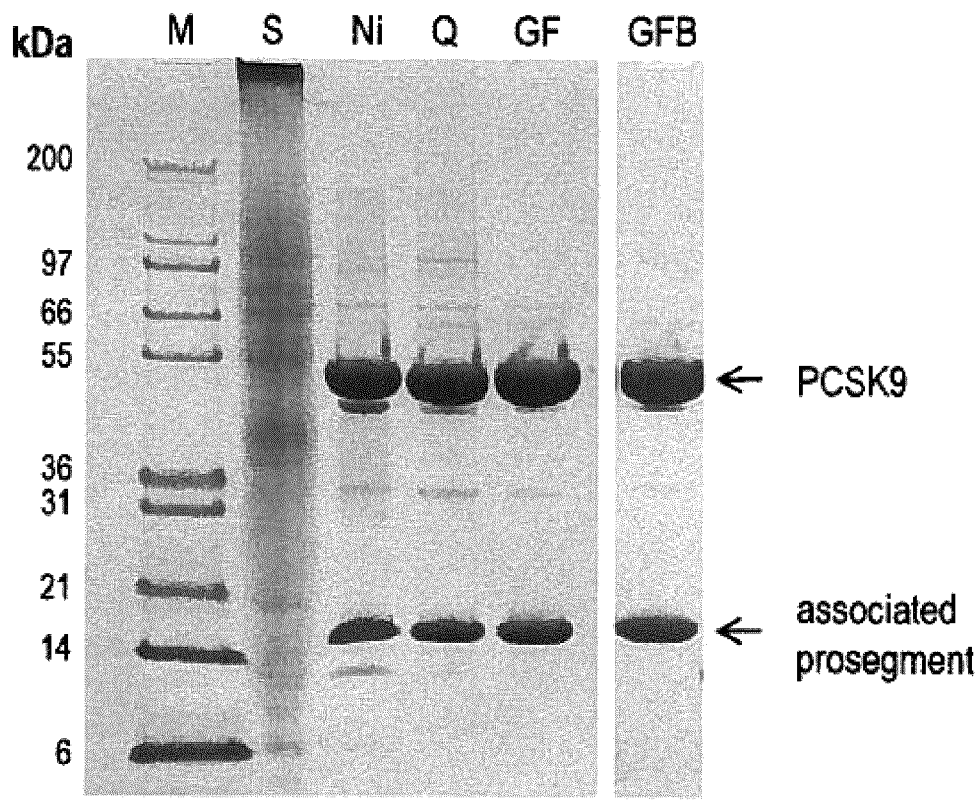
FIG. 1 shows [A] baculovirus expression and purification of human PCSK9 heterodimer complex formed of the prosegment (amino acids 31 to 152) and the catalytic subunit (amino acids 153 to 692). [B] Immune response against human purified PCSK9 by a llama immunized with the antigen as shown by ELISA and estimated by optical density of retained proteins at 450 nm ($OD_{450}$). 5 µg/ml PCSK9 was used to coat the ELISA plates. [C] Differential immune response against human PCSK9 by a llama after different repeats of immunization as shown by ELISA. ~1 µg/ml PCSK9 was used to coat the ELISA plates.

Proprotein convertase subtilisin-kexin type 9 (PCSK9) also known as neural apoptosis-regulated convertase 1 (NARC-1), is a proteinase K-Hke subtilase of 692 amino acids in human (NP_777596.2), and comprises a signal peptide (1-30) followed by a prosegment (residues 31-152), a catalytic domain (residues 153-454) and a C-terminal Cys-His-rich domain (CHRD; residues 455-692). PCSK9 is expressed in cells capable of proliferation and differentiation such as hepatocytes, kidney mesenchymal cells, intestinal ileum, colon epithelia and embryonic brain telencephalic neurons (Seidah et al., 2003, Proc. Natl. Acad. Sci. USA 100:928-933).

Following translocation in the ER, the prosegment of PCSK9 is autocatalytically cleaved at the VFAQ$_{152}$↓SIP site. In PCs, the prosegment (pro) is an intramolecular chaperone/inhibitor that is usually removed intracellularly to yield a fully active protease. Different from other PCs, PCSK9 is secreted as a stable non-covalent complex [pro≡ PCSK9]. Accordingly, enhanced degradation of the LDLR induced by PCSK9 does not require the catalytic activity of the mature PCSK9 form. In human and mouse plasma, both full-length PCSK9 (153-692) and a truncated form PCSK9-ΔN218 (219-692) can be detected. The latter, which has no activity on LDLR, is likely generated by Furin and/or PC5, since they cleave PCSK9 ex vivo at RFHR218↓.

In the studies disclosed herein, the present inventors have generated single domain antibodies directed against human PCSK9 and shown that these antibodies inhibit PCSK9-induced LDLR degradation in the HuH7 hepatocarcinoma and HepG2 cell lines.

Accordingly, in a first aspect, the present invention provides an antibody specifically binding to human PCSK9, said antibody comprising:

(i) a complementary determining region (CDR) 1 region comprising an amino acid sequence of formula I:

(SEQ ID NO: 1)
X1-X2-X3-X4-X5 (I)

wherein
X1 is D, N, H, V, A, I or S;
X2 is Y, P or A;
X3 is I, A, T, V or Y;
X4 is L, V, T or M; and
X5 is G, S or A;
or a sequence substantially identical thereto;

(ii) a CDR2 region comprising an amino acid sequence of formula II:

(SEQ ID NO: 2)
Z1-Z2-Z3-Z4-Z5-Z6-Z7-Z8-Z9-Z10-Z11-Z12-Z13-Z14-
Z15-Z16-Y-Z17-Z18-Z19-Z20-Z21-G (II)

wherein
Z1 is A, Q, T, G or S;
Z2 is I, V or A;
Z3 is R, T, A or S;
Z4 is G, E, S, Q, A or D;
Z5 is S, P, V, R, H or G;
Z6 is G, A or D;
Z7 is A, S, D, G or T;
Z8 is I, V or is absent;
Z9 is R, T or is absent;
Z10 is G, A or is absent;
Z11 is R, D or is absent;
Z12 is E, V or is absent;
Z13 is G, E or is absent;
Z14 is S, R, F or is absent;
Z15 is T, I or S;
Z16 is F, Y, E, D, P, A or N;
Z17 is V, A, S, E or T;
Z18 is D, H, N, E, R or V;
Z19 is S, N or F;
Z20 is V or A; and
Z21 is K or R; or a sequence substantially identical thereto; and/or (iii) a CDR3 region comprising an amino acid sequence of formula III:

(SEQ ID NO: 3)
B1-B2-B3-B4-B5-B6-B7-B8-B9-B10-B11-B12-B13-B14-
B14-B15-B16-B17-B18 (III)

wherein
B1 is D, T, A, P, R or Y;
B2 is R, Q, K, T, L, Y, P, A or S;
B3 is F, Y, S, R, A, G or M;
B4 is P, G, Y, S, F or is absent;
B5 is T, N, S, Y or is absent;
B6 is P, Y, T, I, G, R or is absent;
B7 is E, N, R, D, T or is absent;
B8 is F, Y, L, I, V or is absent;
B9 is S, T, M, P, Y or is absent;
B10 is T, G, D, H or S;
B11 is Q, P, T, A, R, H, V or E;
B12 is V, D, L, H, S, F or T;
B13 is G, P, L, H, R, S or M, in a specific embodiment, B13 is G, P, L, R, S or M;
B14 is K, N, E, W, V or is absent;
B15 is H, K, E, T, G, N or S;
B16 is Y, S or Q;
B17 is D, H, V, E, A or is absent; and
B18 is Y, L, H, V or is absent;
or a sequence substantially identical thereto.

In another embodiment, the above-mentioned CDR1 region comprises one of the following amino acid sequences: DYILG (SEQ ID NO: 4), NYIVG (SEQ ID NO: 5), HYILG (SEQ ID NO: 6), VYAMG (SEQ ID NO: 7), DYAMG (SEQ ID NO: 8), NYAMG (SEQ ID NO: 9), AYAMG (SEQ ID NO: 10), IAYMA (SEQ ID NO: 11), SPTMA (SEQ ID NO: 12), HYIVG (SEQ ID NO: 13), HYVTS (SEQ ID NO: 14) or a sequence substantially identical thereto.

In an embodiment, the above-mentioned CDR2 region comprises one of the following amino acid sequences: AIRGSGAIRGREGSTFYVDSVKG (SEQ ID NO: 15), AIRGSGAIRGREGSTYYADSVKG (SEQ ID NO: 16), AIRESGSSTYYADSVKG (SEQ ID NO: 17), AITSPGDSIPYAHSVKG (SEQ ID NO: 18), AITSSGDSIPYAHSVKG (SEQ ID NO: 19), AAAQSGDSSAYARSVKG (SEQ ID NO: 20), QISQVDGFTYYEDSVKG (SEQ ID NO: 21), TIRDSDASIYYTDSVKG (SEQ ID NO: 22), SISSGGTTNYAVFAKG (SEQ ID NO: 23), AIRSRDDSTYYSNSVKG (SEQ ID NO: 24), AIRESGSRTYYADSVRG (SEQ ID NO: 25), AVRESGSSTEYAENVKG (SEQ ID NO: 26), AVREPGSSTYYADSVKG (SEQ ID NO: 27), GVTAHAGVTADVESTDYSDSVKG (SEQ ID NO: 28), or a sequence substantially identical thereto. In an embodiment, the above-mentioned CDR3 region comprises one of the following amino acid sequences: DRFPTPEFSTQVGHYDY (SEQ ID NO: 29), DRFPTPEFTTQVGHYDV (SEQ ID NO: 30), DQYPTPEFSTQVGHYDY (SEQ ID NO: 31), TKSGNYNYMGPDPKKYHY (SEQ ID NO: 32), TTSGTYNYMGPDPKEYVY (SEQ ID NO: 33), TTRGSYEYMGPDPKKYEY (SEQ ID NO: 34), ALAFPTTSSNTYAY (SEQ ID NO: 35), RQYYSGRVYSTFREEYDY (SEQ ID NO: 36), YAMSTETMVSQDY (SEQ ID NO: 37), TYSGTYNYMGADPKEYVY (SEQ ID NO: 38), DPRTIDLSSRLLWGS (SEQ ID NO: 39), DQYPTTEFSTQVGHYDY (SEQ ID NO: 40), DRFPTPEFSDRVGHYDL (SEQ ID NO: 41), DPYPTPEFTTHVGHYDY (SEQ ID NO: 42), PSGFYRTIPHVHSNYDH (SEQ ID NO: 43) or a sequence substantially identical thereto.

In an embodiment, the above-mentioned CDR1, CDR2 and CDR3 regions respectively comprise: DYILG (SEQ ID NO: 4), AIRGSGAIRGREGSTFYVDSVKG (SEQ ID NO: 15) and DRFPTPEFSTQVGHYDY (SEQ ID NO: 29), or sequences substantially identical thereto.

In an embodiment, the above-mentioned CDR1, CDR2 and CDR3 regions respectively comprise: NYIVG (SEQ ID NO: 5), AIRGSGAIRGREGSTYYADSVKG (SEQ ID NO: 16) and DRFPTPEFTTQVGHYDV (SEQ ID NO: 30), or sequences substantially identical thereto.

In an embodiment, the above-mentioned CDR1, CDR2 and CDR3 regions respectively comprise: DYILG (SEQ ID NO: 4), AIRESGSSTYYADSVKG (SEQ ID NO: 17) and DQYPTPEFSTQVGHYDY (SEQ ID NO: 31), or sequences substantially identical thereto.

In an embodiment, the above-mentioned CDR1, CDR2 and CDR3 regions respectively comprise: HYILG (SEQ ID NO: 6), AIRESGSSTYYADSVKG (SEQ ID NO: 17) and DQYPTPEFSTQVGHYDY (SEQ ID NO: 31), or sequences substantially identical thereto.

In an embodiment, the above-mentioned CDR1, CDR2 and CDR3 regions respectively comprise: VYAMG (SEQ ID NO: 7), AITSPGDSIPYAHSVKG (SEQ ID NO: 18) and TKSGNYNYMGPDPKKYHY (SEQ ID NO: 32), or sequences substantially identical thereto.

In an embodiment, the above-mentioned CDR1, CDR2 and CDR3 regions respectively comprise: VYAMG (SEQ ID NO: 7), AITSSGDSIPYAHSVKG (SEQ ID NO: 19) and TTSGTYNYMGPDPKEYVY (SEQ ID NO: 33), or sequences substantially identical thereto.

In an embodiment, the above-mentioned CDR1, CDR2 and CDR3 regions respectively comprise: DYAMG (SEQ ID NO: 8), AAAQSGDSSAYARSVKG (SEQ ID NO: 20) and TTRGSYEYMGPDPKKYEY (SEQ ID NO: 34), or sequences substantially identical thereto.

In an embodiment, the above-mentioned CDR1, CDR2 and CDR3 regions respectively comprise: NYAMG (SEQ ID NO: 9), QISQVDGFTYYEDSVKG (SEQ ID NO: 21) and ALAFPTTSSNTYAY (SEQ ID NO: 35), or sequences substantially identical thereto.

In an embodiment, the above-mentioned CDR1, CDR2 and CDR3 regions respectively comprise: AYAMG (SEQ ID NO: 10), TIRDSDASIYYTDSVKG (SEQ ID NO: 22) and RQYYSGRVYSTFREEYDY (SEQ ID NO: 36), or sequences substantially identical thereto.

In an embodiment, the above-mentioned CDR1, CDR2 and CDR3 regions respectively comprise: IAYMA (SEQ ID NO: 11), SISSGGTTNYAVFAKG (SEQ ID NO: 23) and YAMSTETMVSQDY (SEQ ID NO: 37), or sequences substantially identical thereto.

In an embodiment, the above-mentioned CDR1, CDR2 and CDR3 regions respectively comprise: NYAMG (SEQ ID NO: 9), QISQVDGFTYYEDSVKG (SEQ ID NO: 21) and TYSGTYNYMGADPKEYVY (SEQ ID NO: 38), or sequences substantially identical thereto.

In an embodiment, the above-mentioned CDR1, CDR2 and CDR3 regions respectively comprise: SPTMA (SEQ ID NO: 12), AIRSRDDSTYYSNSVKG (SEQ ID NO: 24) and DPRTIDLSSRLLWGS (SEQ ID NO: 39), or sequences substantially identical thereto.

In an embodiment, the above-mentioned CDR1, CDR2 and CDR3 regions respectively comprise: HYILG (SEQ ID NO: 6), AIRESGSRTYYADSVRG (SEQ ID NO: 25) and DQYPTTEFSTQVGHYDY (SEQ ID NO: 40), or sequences substantially identical thereto.

In an embodiment, the above-mentioned CDR1, CDR2 and CDR3 regions respectively comprise: HYIVG (SEQ ID NO: 13), AVRESGSSTEYAENVKG (SEQ ID NO: 26) and DRFPTPEFSDRVGHYDL (SEQ ID NO: 41), or sequences substantially identical thereto.

In an embodiment, the above-mentioned CDR1, CDR2 and CDR3 regions respectively comprise: HYILG (SEQ ID NO: 6), AIRESGSRTYYADSVRG (SEQ ID NO: 25) and DQYPTPEFSTQVGHYDY (SEQ ID NO: 31), or sequences substantially identical thereto.

In an embodiment, the above-mentioned CDR1, CDR2 and CDR3 regions respectively comprise: HYILG (SEQ ID NO: 6), AVREPGSSTYYADSVKG (SEQ ID NO: 27) and DPYPTPEFTTHVGHYDY (SEQ ID NO: 42), or sequences substantially identical thereto.

In an embodiment, the above-mentioned CDR1, CDR2 and CDR3 regions respectively comprise: HYVTS (SEQ ID NO: 14), GVTAHAGVTADVESTDYSDSVKG (SEQ ID NO: 28) and PSGFYRTIPHVHSNYDH (SEQ ID NO: 43), or sequences substantially identical thereto.

In another embodiment, the above-mentioned antibody further comprises a framework region (FR) 1 comprising an amino acid sequence of formula IV:

(SEQ ID NO: 44)
Q-V-X6-L-X7-E-S-G-G-G-X8-V-Q-A-G-X9-S-X10-R-L-S-C-
X11-X12-X13-X14-X15-X16-X17-X18 (IV)

wherein
X6 is K or Q;
X7 is E or V;

X8 is L or P;
X9 is G or D
X10 is L or M;
X11 is V, L, S, or A;
X12 is A or P;
X13 is S or P;
X14 is G, D or R;
X15 is R, L or S;
X16 is T, F, I or G;
X17 is I, V, P or F; and
X18 is N, R, S or V
or a sequence substantially identical thereto.

In an embodiment, X6 is K; X7 is E; X8 is L; X9 is G; X10 is L; X11 is A; X12 is A; X13 is S; X14 is G; X15 is R; X16 is T; X17 is F; and/or X18 is N.

In a further embodiment, the above-mentioned FR1 comprises one of the following amino acid sequences:

```
                                       (SEQ ID NO: 45)
QVKLEESGGGLVQAGGSLRLSCVASGRTIN, (SEQ ID NO: 46)
QVQLVESGGGLVQAGGSLRLSCLASDRTVN, (SEQ ID NO: 47)
QVQLVESGGGLVQAGGSLRLSCAASGRTPR, (SEQ ID NO: 48)
QVQLVESGGGLVQAGGSLRLSCAASGRTFS, (SEQ ID NO: 49)
QVKLEESGGGLVQAGGSLRLSCAASGRTFS, (SEQ ID NO: 50)
QVKLEESGGGLVQAGGSLRLSCAASGRTFN, (SEQ ID NO: 51)
QVKLEESGGGLVQAGGSLRLSCAASGLTFS, (SEQ ID NO: 52)
QVKLEESGGGLVQAGGSLRLSCSPSDRTFS, (SEQ ID NO: 53)
QVKLEESGGGLVQAGGSLRLSCAAPRSGVV, (SEQ ID NO: 54)
QVKLEESGGGPVQAGGSLRLSCLASGRFVN, (SEQ ID NO: 55)
QVQLVESGGGLVQAGGSMRLSCAASGRTPR, (SEQ ID NO: 56)
QVKLEESGGGLVQAGGSLRLSCAASGRTPR, (SEQ ID NO: 57)
QVKLEESGGGLVQAGDSLRLSCAASGRIFN,
``` or a sequence substantially identical thereto.

In another embodiment, the above-mentioned antibody further comprises an FR2 comprising an amino acid sequence of formula V:

```
                                       (SEQ ID NO: 58)
X19-X20-R-Q-X21-P-X22-X23-X24-X25-X26-X27-V-X28

(V)
``` wherein
X19 is W or Y;
X20 is F or Y;
X21 is A or V;
X22 is G, D or E;
X23 is K, T, R, A, E or Q;
X24 is K, E, Q or L;
X25 is R or P;
X26 is E or K;
X27 is F or L; and
X28 is A, T or G,
or a sequence substantially identical thereto.

In an embodiment, X19 is W; X20 is F; X21 is A; X22 is G; X23 is K; X24 is E; X25 is R; X26 is E; X27 is F; and/or X28 is A.

In an embodiment, the above-mentioned FR2 comprises one of the following amino acid sequences:

```
                                       (SEQ ID NO: 59)
WFRQAPGKKREFVA, (SEQ ID NO: 60)
YFRQAPGKEREFVA, (SEQ ID NO: 61)
WFRQAPGKQREFVA, (SEQ ID NO: 62)
WFRQAPGKEREFVA, (SEQ ID NO: 63)
WFRQAPGKEREFVT, (SEQ ID NO: 64)
WFRQAPGTEREFVG, (SEQ ID NO: 65)
WFRQVPGREREFVA, (SEQ ID NO: 66)
WYRQAPEKQRELVA, (SEQ ID NO: 67)
WFRQAPGAEREFVG, (SEQ ID NO: 68)
WFRQAPGEERKFVA, (SEQ ID NO: 69)
WFRQAPGKLPEFVA, (SEQ ID NO: 70)
WFRQAPDQEREFVA,
``` or a sequence substantially identical thereto.

In another embodiment, the above-mentioned antibody further comprises an FR3 comprising an amino acid sequence of formula VI:

```
                                       (SEQ ID NO: 71)
R-X29-X30-X31-S-X32-X33-X34-X35-K-X36-X37-X38-X39-
L-X40-M-X41-S-L-X42-P-X43-D-X44-A-X45-Y-X46-C-X47-
X48 (VI)
``` wherein
X29 is Y, F or D;
X30 is T, S or V;
X31 is I or V;
X32 is K, R, A or L;
X33 is D or N;
X34 is N, G, H or Y;
X35 is A, T, V or S;
X36 is N or S;
X37 is T or A;
X38 is V, I, L, A or G;
X39 is Y, D or F;
X40 is Q or R;
X41 is N, D or S;
X42 is K, I or Q;

X43 is E or D;
X44 is S or T;
X45 is T, V or A;
X46 is Y or I;
X47 is A or N; and
X48 is A, V, L or G,
or a sequence substantially identical thereto.

In an embodiment, X29 is F; X30 is T; X31 is I; X32 is R; X33 is D; X34 is N; X35 is A; X36 is N; X37 is T; X38 is V; X39 is Y; X40 is Q; X41 is N; X42 is K; X43 is E; X44 is T; X45 is V; X46 is Y; X47 is A; and/or X48 is A.

In an embodiment, the above-mentioned FR3 comprises one of the following amino acid sequences:

```
                                        (SEQ ID NO: 72)
RYTISKDNAKNTVDLQMNSLKPEDSATYYCAV, (SEQ ID NO: 73)
RFSISKDNAKNTIYLQMNSLKPEDSAVYYCAL, (SEQ ID NO: 74)
RYTISRNNTKNAVDLQMNSLKPEDSATYYCAV, (SEQ ID NO: 75)
RYTISRDNTKNAVDLQMNSLKPEDSATYYCAV, (SEQ ID NO: 76)
RFTISRDNAKNTLYLQMNSLKPEDTAAYYCAA, (SEQ ID NO: 77)
RFTISRDNAKNTVYLQMNSLKPEDTAAYYCAA, (SEQ ID NO: 78)
RFTISRDGAKNTAYLQMDSLKPEDTAAYYCAA, (SEQ ID NO: 79)
RFTISRDNAKNTVYLQMNSLKPDDTAVYYCAA, (SEQ ID NO: 80)
RFTISRDNAKNTVYLQMNSLIPDDTAVYYCAA, (SEQ ID NO: 81)
RFTISADNAKNTVYLQMNSLKPEDTAVYICNA, (SEQ ID NO: 82)
RFTISRDNAKNTVYLQMSSLKPDDTAVYYCAA, (SEQ ID NO: 83)
RFTISLDNAKNTAYLRMDSLQPEDTAVYYCAG, (SEQ ID NO: 84)
RDTISRDNTKNAGDLQMNSLKPEDSATYYCAV, (SEQ ID NO: 85)
RFVISKDNVKSTVFLQMNSLKPEDSAVYYCAL, (SEQ ID NO: 86)
RDTISKDHTKNAVDLQMNSLKPEDSATYYCAV, (SEQ ID NO: 87)
RFTVSRDYSKNTVYLQMNSLKPEDTAVYYCAA,
``` or a sequence substantially identical thereto.

In another embodiment, the above-mentioned antibody further comprises an FR4 comprising an amino acid sequence of formula VII:

```
                                        (SEQ ID NO: 88)
X49-G-X50-G-T-X51-V-T-X52-S-S (VII)
``` wherein
X49 is W or S;
X50 is R or Q;
X51 is Q or E; and
X52 is V or I,
or a sequence substantially identical thereto.

In an embodiment, X49 is W; X50 is Q; X51 is Q; and/or X52 is V, or a sequence substantially identical thereto.

In an embodiment, the above-mentioned FR4 comprises one of the following amino acid sequences: WGQGTQVTVSS (SEQ ID NO: 89), WGRGTQVTVSS (SEQ ID NO: 90), SGQGTQVTVSS (SEQ ID NO: 91), WGQGTEVTISS (SEQ ID NO: 92), or a sequence substantially identical thereto.

In an embodiment, the above-mentioned antibody comprises, or consists of, one of the following amino acid sequences:

```
                                        (SEQ ID NO: 93)
QVKLEESGGGLVQAGGSLRLSCVASGRTINDYILGWFRQAPGKKREFVAA

IRGSGAIRGREGSTFYVDSVKGRYTISKDNAKNTVDLQMNSLKPEDSATY

YCAVDRFPTPEFSTQVGHYDYWGQGTQVTVSS;

(SEQ ID NO: 94)
QVQLVESGGGLVQAGGSLRLSCLASDRTVNNYIVGYFRQAPGKEREFVAA

IRGSGAIRGREGSTYYADSVKGRFSISKDNAKNTIYLQMNSLKPEDSAVY

YCALDRFPTPEFTTQVGHYDVWGRGTQVTVSS;

(SEQ ID NO: 95)
QVKLEESGGGLVQAGGSLRLSCVASGRTINDYILGWFRQAPGKKREFVAA

IRESGSSTYYADSVKGRYTISRNNTKNAVDLQMNSLKPEDSATYYCAVDQ

YPTPEFSTQVGHYDYWGQGTQVTVSS;

(SEQ ID NO: 96)
QVQLVESGGGLVQAGGSLRLSCAASGRTPRHYILGWFRQAPGKQREFVAA

IRESGSSTYYADSVKGRYTISRDNTKNAVDLQMNSLKPEDSATYYCAVDQ

YPTPEFSTQVGHYDYWGQGTQVTVSS;

(SEQ ID NO: 97)
QVQLVESGGGLVQAGGSLRLSCAASGRTFSVYAMGWFRQAPGKEREFVAA

ITSPGDSIPYAHSVKGRFTISRDNAKNTLYLQMNSLKPEDTAAYYCAATK

SGNYNYMGPDPKKYHYWGQGTQVTVSS;

(SEQ ID NO: 98)
QVKLEESGGGLVQAGGSLRLSCAASGRTFSVYAMGWFRQAPGKEREFVTA

ITSSGDSIPYAHSVKGRFTISRDNAKNTVYLQMNSLKPEDTAAYYCAATT

SGTYNYMGPDPKEYVYWGQGTQVTVSS;

(SEQ ID NO: 99)
QVKLEESGGGLVQAGGSLRLSCAASGRTFNDYAMGWFRQAPGKEREFVAA

AAQSGDSSAYARSVKGRFTISRDGAKNTAYLQMDSLKPEDTAAYYCAATT

RGSYEYMGPDPKKYEYWGQGTQVTVSS;

(SEQ ID NO: 100)
QVKLEESGGGLVQAGGSLRLSCAASGLTFSNYAMGWFRQAPGTEREFVGQ

ISQVDGFTYYEDSVKGRFTISRDNAKNTVYLQMNSLKPDDTAVYYCAAAL

AFPTTSSNTYAYSGQGTQVTVSS;

(SEQ ID NO: 101)
QVKLEESGGGLVQAGGSLRLSCSPSDRTFSAYAMGWFRQVPGREREFVAT

IRDSDASIYYTDSVKGRFTISRDNAKNTVYLQMNSLIPDDTAVYYCAARQ

YYSGRVYSTFREEYDYWGQGTQVTVSS;
```

(SEQ ID NO: 102)
QVKLEESGGGLVQAGGSLRLSCAAPRSGVVIAYMAWYRQAPEKQRELVAS

ISSGGTTNYAVFAKGRFTISADNAKNTVYLQMNSLKPEDTAVYICNAYAM

STETMVSQDYWGQGTQVTVSS;

(SEQ ID NO: 103)
QVKLEESGGGLVQAGGSLRLSCAASGLTFSNYAMGWFRQAPGAEREFVGQ

ISQVDGFTYYEDSVKGRFTISRDNAKNTVYLQMSSLKPDDTAVYYCAATY

SGTYNYMGADPKEYVYWGQGTQVTVSS;

(SEQ ID NO: 104)
QVKLEESGGGPVQAGGSLRLSCLASGRFVNSPTMAWFRQAPGEERKFVAA

IRSRDDSTYYSNSVKGRFTISLDNAKNTAYLRMDSLQPEDTAVYYCAGDP

RTIDLSSRLLWGSWGQGTQVTVSS;

(SEQ ID NO: 105)
QVQLVESGGGLVQAGGSMRLSCAASGRTPRHYILGWFRQAPGKQREFVAA

IRESGSRTYYADSVRGRDTISRDNTKNAGDLQMNSLKPEDSATYYCAVDQ

YPTTEFSTQVGHYDYWGQGTEVTISS;

(SEQ ID NO: 106)
QVKLEESGGGLVQAGGSLRLSCAASGRTPRHYIVGWFRQAPGKEREFVAA

VRESGSSTEYAENVKGRFVISKDNVKSTVFLQMNSLKPEDSAVYYCALDR

FPTPEFSDRVGHYDLWGQGTQVTVSS;

(SEQ ID NO: 107)
QVQLVESGGGLVQAGGSMRLSCAASGRTPRHYILGWFRQAPGKQREFVAA

IRESGSRTYYADSVRGRYTISRDNTKNAVDLQMNSLKPEDSATYYCAVDQ

YPTPEFSTQVGHYDYWGQGTQVTVSS;

(SEQ ID NO: 108)
QVKLEESGGGLVQAGGSLRLSCAASGRTPRHYILGWFRQAPGKLPEFVAA

VREPGSSTYYADSVKGRDTISKDHTKNAVDLQMNSLKPEDSATYYCAVDP

YPTPEFTTHVGHYDYWGQGTQVTVSS;

(SEQ ID NO: 109)
QVKLEESGGGLVQAGDSLRLSCAASGRIFNHYVTSWFRQAPDQEREFVAG

VTAHAGVTADVESTDYSDSVKGRFTVSRDYSKNTVYLQMNSLKPEDTAVY

YCAAPSGFYRTIPHVHSNYDHWGQGTQVTVSS;

or a sequence substantially identical thereto.

The term "antibody" as referred to herein includes whole antibodies and any antigen binding fragment (i.e., "antigen-binding portion"), single chains thereof, as well as single domain antibodies. Conventional antibodies typically comprise at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. See generally, Fundamental Immunology Ch. 7 (Paul, W., ed., 2nd ed. Raven Press, N.Y. (1989)).

The term "antigen-binding portion" of an antibody (or simply "antibody portion"), as used herein, refers to one or more fragments of an antibody that retain the ability to specifically bind to an antigen (e.g., PCSK9). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a $F_d$ fragment consisting of the $V_H$ and $C_{H1}$ domains; (iv) a Fv fragment consisting of the $V_L$ and $V_H$ domains of a single arm of an antibody, (v) a dAb fragment (Ward et al., Nature 341:544-546 (1989)), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). Such single chain antibodies are also intended to be encompassed within the term "antigen-binding portion" of an antibody. These antibody fragments may be obtained using any suitable technique, including conventional techniques known to those with skill in the art, and the fragments may be screened for utility in the same manner as are intact antibodies.

In an embodiment, the above-mentioned antibody is a single domain antibody. Single domain antibodies (sdAbs) as used herein, refer to antibodies whose complementary determining regions (CDR) are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, alpaca, guanaco, goat, rabbit, bovine. According to one aspect of the invention, a single domain antibody as used herein is a naturally occurring single domain antibody known as heavy chain antibody devoid of light chains. For clarity reasons, this variable domain derived from a heavy chain antibody naturally devoid of light chain is known herein as a $V_H$H or nanobody to distinguish it from the conventional $V_H$ of four chain immunoglobulins. Such a $V_H$H molecule or sdAb can be derived from antibodies raised in Camelidae species, for example in camel, llama, dromedary, alpaca and guanaco. Other species besides Camelidae may produce heavy chain antibodies naturally devoid of light chain; such $V_H$Hs are within the scope of the invention. They have also been observed in shark and are termed $V_{NAR}$s, and may be engineered based on human heavy chain sequences. As used herein, sdAbs include those directly isolated from VH, $V_H$H or $V_{NAR}$ reservoir of any origin through phage display or other display technologies and those generated through further modification of such sdAbs by humanization, affinity maturation, stabilization and other way of antibody engineering. The term also includes homologues, derivatives, or fragments that are capable of functioning as a single-domain antibody domain and which exhibits biological activity (e.g., binding to PCSK9).

As further described herein, the amino acid sequence and structure of sdAbs can be considered—without however being limited thereto—to be comprised of four framework regions or "FRs", which are referred to in the art and herein as "Framework region 1 or "FR1"; "Framework region 2" or "FR2"; "Framework region 3" or "FR3"; and "Framework region 4" or "FR4", respectively; which framework regions are interrupted by three complementary determining regions or "CDRs", which are referred to in the art as "Complementarity Determining Region 1" or "CDR1"; "Complementarity Determining Region 2" or "CDR2"; and "Complementarity Determining Region 3" or "CDR3", respectively. The total number of amino acid residues in a single domain antibody can be from about 110-140, or about 110-130. It should however be noted that parts, fragments or analogs of a single domain antibody are not particularly limited as to their length and/or size, as long as such parts, fragments or analogs meet the further requirements outlined herein and are also preferably suitable for the purposes described herein.

The amino acid residues of a single domain antibody are numbered according to the general numbering for $V_H$ domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans (Riechmann and Muyldermans, *J. Immunol. Methods* 1999 Dec. 10; 231 (1-2): 25-38; see for example FIG. 2 of said reference). According to this numbering, the FR1 of a single domain antibody comprises the amino acid residues at about positions 1-30, the CDR1 comprises the amino acid residues at about positions 31-35, the FR2 comprises the amino acids at about positions 36-49, the CDR2 comprises the amino acid residues at about positions 50-65, the FR3 comprises the amino acid residues at about positions 66-94, the CDR3 comprises the amino acid residues at about positions 95-102, and the FR4 comprises the amino acid residues at about positions 103-113. It should be noted that, as is well known in the art for $V_H$ domains and for $V_HH$ domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDRs, position 1 according to the Kabat numbering corresponds to the start of FR1, position 36 according to the Kabat numbering corresponds to the start of FR2, position 66 according to the Kabat numbering corresponds to the start of FR3, and position 103 according to the Kabat numbering corresponds to the start of FR4. Software and online tools (e.g., Abnum, http://www.bioinf.org.uk/abs/abnum/) for numbering a given antibody sequence using the Kabat numbering scheme are available (see Abhinandan, K. R. and Martin, A. C. R. (2008) Analysis and improvements to Kabat and structurally correct numbering of antibody variable domains Molecular Immunology, 45, 3832-3839).

The Kabat numbering of the sequence identified herein as "PKE2", using the Abnum antibody amino acid numbering tool, is depicted in FIG. 5.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g., size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (He or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2, BLAST-P, BLAST-N, COBALT or FASTA-N, or any other appropriate software/tool that is known in the art (Johnson M, et al. (2008) *Nucleic Acids Res.* 36:W5-W9; Papadopoulos J S and Agarwala R (2007) *Bioinformatics* 23:1073-79).

The substantially identical sequences of the present invention may be at least 75% identical; in another example, the substantially identical sequences may be at least 80, 85, 90, 95, 96, 97, 98 or 99% identical at the amino acid level to sequences described herein. The substantially identical sequences retain substantially the activity and specificity of the reference sequence.

The sdAb of the present invention may also comprise additional sequences to aid in expression, detection or purification of a recombinant antibody or fragment thereof.

For example, and without wishing to be limiting, the antibody or fragment thereof may comprise a targeting or signal sequence (for example, but not limited to ompA or PCSK9), a detection and/or purification tag (for example, but not limited to c-Myc, His-tag or V5 tag), or a combination thereof.

The sdAb of the present invention may also be in a multivalent display. Multimerization may be achieved by any suitable method of know in the art. For example, and without wishing to be limiting in any manner, multimerization may be achieved using self-assembly molecules (Zhang, J. et al. *J Mol. Biol.* 341, 161-169 (2004); Zhang, J. et al., *J Mol Biol* 335, 49-56 (2004)), as described in PCT publication No. WO 2003/046560. The described method produces pentabodies by expressing a fusion protein comprising the antibody or fragment thereof and a pentamerization domain, which assembles into a pentamer, through which a multivalent display of the antibody or fragment thereof is achieved. Each subunit of the pentamer may be the same or different. Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielsen et al. *Cancer research* 60, 6434-6440 (2000)), c-jun/Fos interaction (de Kruif, J. & Logtenberg, T. *J Biol Chem* 271, 7630-7634 (1996)), or "Knob into holes" interaction (Ridgway et al. *Protein Eng* 9, 617-621 (1996)).

The sdAb of the present invention may also be conjugated to or fused with a particular moiety, for example to increase its stability/half-life and/or to facilitate its targeting to a particular cell, organ and/or tissue and/or to facilitate cell entry. In an embodiment, the single domain antibody is fused with an Fc region of an antibody, in a further embodiment to a human IgG4-Fc region.

In an embodiment, the above-mentioned sdAb blocks or interferes with the interaction between PCSK9 and the epidermal growth factor-like repeat A (EGF-A) domain of the LDLR. In an embodiment, the above-mentioned sdAb is directed to the catalytic domain of PCSK9, in a further embodiment to a region corresponding to residues 153-156 and/or 367-381 of PCSK9.

In an embodiment, the above-mentioned single domain antibody has a dissociation constant $(K_D)$ of $1 \times 10^{-7}$ or less, or less, in further embodiments, the above-mentioned single domain antibody has a dissociation constant $(K_D)$ of $1 \times 10^{-8}$ M, $1 \times 10^{-8}$ M, $1 \times 10^{-10}$ M, $1 \times 10^{-11}$ M, or $1 \times 10^{-12}$ M or less.

Functional Characterization of the sdAbs

The functional characteristics of the sdAbs of the present invention can be tested in vitro and in vivo. For example, PCSK9-binding sdAbs can be tested for the ability to inhibit interaction of PCSK9 with LDLR, to trigger the entry of sdAbs into cell, could also be measured by inhibition of PCSK9-dependent effects on LDLR (e.g., LDLR mediated uptake of LDL-C), inhibition of PCSK9 proteolytic activity, inhibition of PCSK9-dependent LDLR degradation, and decrease LDL-C in vivo. PCSK9 binding to LDLR can be detected by surface plasmon resonance (SPR) (using BIAcore®) by immobilizing LDLR to a solid support and detecting soluble PCSK9 binding to the LDLR. Alternatively, PCSK9 can be immobilized, and LDLR binding can be detected. PCSK-9/LDLR binding can also be analyzed by ELISA (e.g., by detecting PCSK9 binding to immobilized LDLR), by fluorescence resonance energy transfer (FRET), or phage display. To perform FRET, fluorophore-labeled PCSK9 binding to LDLR in solution can be detected (see, for example, U.S. Pat. No. 5,631,169). PCSK9 binding to LDL-R has been detected by coimmunoprecipitation (Lagace et al., 2006 *J. Clin. Inv.* 116(11):2995-3005). To examine PCSK9-LDLR binding in this manner, HepG2 cells are cultured in sterol-depleted medium for 18 hours. Purified PCSK9 is added to the medium in the presence of 0.1 mM chloroquine and the cells are incubated for one hour. Cells are lysed in mild detergent (1% digitonin w/vol). PCSK9 or LDLR is immunoprecipitated from cell lysates, separated by SDS-PAGE, and immunoblotted to detect the presence of coimmunoprecipitated LDLR or PCSK9, respectively (Lagace et al., 2006, supra).

These assays may be conducted with a mutant form of PCSK9 that binds to LDLR with a higher avidity (e.g., hPCSK9 D374Y, Lagace et al., 2006, supra). Hepatocytes express LDLR on the cell surface. Addition of purified PCSK9 to cultured hepatocyte cells (e.g., HepG2 cells, ATCC HB-8065, HuH7 cells, primary human or mouse hepatocytes) produces a decrease in LDLR expression in a dose- and time-dependent manner (Lagace et al., 2006 supra). PCSK9-binding sdAbs can be tested for the ability to increase LDLR levels in hepatocytes. For example, HepG2 cells are cultured in sterol-depleted medium (DMEM supplemented with 100 U/ml penicillin, 100 µg/ml streptomycin sulfate, and 1 g/l glucose, 5% (vol/vol) newborn calf lipoprotein-deficient serum (NCLPDS), 10 µM sodium compactin, and 50 µM sodium mevalonate) for 18 hours to induce LDLR expression. Purified PCSK9 (5 µg/ml) is added to the medium. LDLR levels in cells harvested at 0, 0.5, 1, 2, and 4 hours after addition of PCSK9 are determined (Lagace et al., 2006, supra). LDLR levels can be determined by flow cytometry, FRET, immunoblotting, or other means. LDL-C uptake by cells (e.g., HepG2 cells, HuH7 cells) can be measured using fluorescently-labeled LDL-C, Dil-LDL (3,3'-dioctadecylindocarbocyanine-low density lipoprotein) as described by Stephan and Yurachek (1993, *J. Lipid Res.* 34: 325-330). Briefly, cells are incubated in culture with Dil-LDL (20-100 µg protein/ml) at 37° C. for 2 hours. Cells are washed, lysed, and the concentration of internalized Dil-LDL is quantitated using a spectrofluorometer. LDL-C uptake can be measured in cells contacted with a PCSK9 binding agent (prior to, and/or during the period in which Dil-LDL is present in the cell culture).

Transgenic mice overexpressing human PCSK9 in liver have increased levels of plasma LDL-C relative to non-transgenic mice (Lagace et al., 2006 supra). See also Maxwell and Breslow, 2004 *Proc. Natl. Acad. Sci. USA,* 101: 7100, describing overexpression of PCSK9 using an adenovirus vector in mice. PCSK9$^{-/-}$ mice have been produced (Rashid et al., 2005 *Proc. Natl. Acad. Sci.* 102(5): 5374-5379). These mice can be genetically modified to express a hPCSK9 transgene. PCSK9 binding molecules can be tested in any of these models, or in animals which are not genetically modified, for the ability to clear or reduce total cholesterol and/or LDL-C.

The kinetics of LDL clearance from plasma can be determined by injecting animals with [$^{125}$I]-labelled LDL, obtaining blood samples at 0, 5, 10, 15, and 30 minutes after injection, and quantitating [$^{125}$I]-LDL in the samples (Rashid et al., 2005 supra). The rate of LDL clearance is increased in PCSK9$^{-/-}$ mice relative to wild type mice (Rashid et al., 2005 supra). Increased LDL clearance in animals administered a PCSK9-binding sdAb indicates that the agent inhibits PCSK9 activity in vivo.

Decreases in total plasma cholesterol, plasma triglycerides, and/or LDL-C in response to treatment with a PCSK9-binding sdAb are indicative of therapeutic efficacy of the PCKS9 binding molecule. Cholesterol and lipid profiles can be determined by colorimetric, gas-liquid chromatographic, or enzymatic means using commercially available kits.

Methods/assays to determine PCSK9 activity are described below.

In Vitro Analysis of PCSk9-Dependant LDLR Degradation.

Compound is tested for its ability to inhibit the LDLR enhanced degradation by PCSK9 on human hepatocyte cell lines HepG2 or HuH7. The assay consists in the addition of wild type (WT), mutants or chimeric PCSK9, either transfected or purified, directly to the culture supernatants in the presence or absence of the tested compound. Each "dose-responses" experiment is done in triplicate for 4 to 6 different dosages. The inhibition of the PCSK9 activity is evidence by an increase of the LDLR protein expression and/or at the cell surface, as evidenced by:

Western blot analysis of cell lysates for the total LDLR;
FACS analysis for cell surface for LDLR;
Fluorescent Dil-LDL incorporation monitoring the cell surface activity of LDLR.

The Dil-LDL fluorescent uptake assay consists in the fluorescence measurement of the Dil-LDL cellular incorporation via LDLR internalization (a measurement of cell surface LDLR activity). The cells are incubated in a 96-well format in the presence or absence of different doses of tested compound for 2 h, and then Dil-LDL was added for an additional 2 h. The inhibition of the PCSK9 activity is detected by an increase in the Dil-LDL fluorescence.

a. WT PCSK9.

The assay consists in the addition of wild type (WT) PCSK9, either as conditioned media from transfected cells or purified, and added to the culture supernatants, in the presence or absence of the tested compound. The dose routinely chosen for PCSK9 added extracellularly is 1 ug/ml.

b. Mutants PCSK9 (Gain of Function).

In order to further characterize whether the tested compound can inhibit the function of a gain of function mutation, the cells are incubated with purified mutant proteins, in the presence or absence of different doses of tested compound. Purified PCSK9 mutants are PCSK9-D374Y, for example (exhibiting a ~25-fold higher affinity towards LDLR) or S127R (showing an increase stability of PCSK9). The dose routinely chosen for PCSK9 and its gain-of-function natural mutant D374Y, added extracellularly are 1 µg/ml and 0.2 µg/ml. Others PCSK9 mutants are similarly used. The assay could also be conducted using culture medium harvested from cells transfected with gain of function PCSK9 mutants.

c. sdAbs.

The assays are conducted using purified sdAbs (6His) added directly to the culture supernatants, or pre-incubated with PCSK9. These assays are also conducted using culture medium collected from cells transfected with the secretable form of sdAbs (e.g., a chimeric construct containing a signal peptide at the amino terminal end of sdAbs) that is V5-tagged.

D. Description of the Assay—Chimeric PCSK9.

Chimeric protein fusing the PCSK9 with the transmembrane and cytosolic domains of the cell surface angiotensin converting enzyme 2 (PCSK9-ACE2) is tested for measuring the activity of the tested compound on the PCSK9 extracellular pathway activity. Alternatively, chimeric protein fusing PCSK9 with the transmembrane and cytosolic domains of the Lamp-1 which directly traffic the protein to the endosomes/lysosomes (PCSK9-Lamp1) is tested for measuring the activity of the tested compound on the PCSK9 intracellular pathway activity. The stable cells expressing the chimeric PCSK9-ACE2 or PCSK9-Lamp1 are available and are be incubated in the presence or absence of different doses of tested compound.

E. Description of the Assay—Primary Human Hepatocytes.

The PCSK9 inhibitory compounds are tested on mouse and human primary hepatocytes in order to measure their effect on cell surface LDLR. The advantage of using the mouse primary hepatocytes, is that it also measure the specificity of the compound in the context of a wild type or knockout mouse expressing or lacking PCSK9, respectively. HepG2 and HuH7 cells that no longer express PCSK9 endogenously (e.g., under a shRNA knockdown) are also used for similar drug specificity purpose.

In Vitro Analysis of PCSK9 Processing and Secretion.

The propCSK9 to PCSK9 processing and secretion are tested using a biosynthetic approach and/or Western blot of PCSK9 in cells and media. Compound(s) are incubated with HEK293 (stably expressing PCSK9) and HuH7 (expressing endogenously PCSK9). For statistical significance each experiment is performed in triplicate. "Dose-dependent" responses of compound(s) are performed.

Protocols

PCSK9 Contained in Media Culture of Transfected Cells.

Human wild type PCSK9 (PCSK9-WT) and gain-of-function (PCSK9-D374Y) proteins are produced by over-expression in HEK293 cells or Huh7 cells. Briefly, HEK 293 or Huh7 cell lines are grown in Dulbecco's modified Eagle's medium with 10% fetal bovine serum (Invitrogen) and maintained at 37° C. under 5% CO2. HEK293 cells are transfected with jetPRIME™ (Polyplus transfection), and Huh7 cells are transfected with Lipofectamine 2000 (Invitrogen), according to the manufacturer's protocol. Twenty-four hours post-transfection, cells are washed and incubated in serum-free medium. Conditioned media containing secreted human PCSK9-D374Y or PCSK9-WT proteins are collected 24 hours later. The level of PCSK9 proteins in conditioned media is quantified by enzyme-linked immunosorbent assay (ELISA), as described previously (Dubuc G, Tremblay M, Paré G, Jacques H, Hamelin J, Benjannet S, Boulet L, Genest J, Bernier L, Seidah N G, Davignon J. 2010. A new method for measurement of total plasma PCSK9: clinical applications. J Lipid Res. 51:140-149.).

SdAbs Secreted in Media Culture of Transfected Cells.

The sdAb cDNAs containing a hexahistidine (6His) tag at the 3' end, or a 6H is tag and a c-Myc tag, are cloned into the pIRES2-EGFP backbone vector (Clonetech). In order to ensure secretion of the sdAbs from transfected cells, the signal peptide (SP) of human PCSK9 is introduced at the amino-terminal end of the sdAb sequence (FIG. 2). The SP is followed by a V5-tag. The control vector pIRES2 contains the signal peptide, the V5 tag and the hexahistidine tag sequences. The sdAbs are collected from the media culture of transfected HEK293 cells. Briefly, HEK 293 cells are grown in Dulbecco's modified Eagle's medium with 10% fetal bovine serum (Invitrogen) and maintained at 37° C. under 5% CO2. At 80-90% confluence, HEK293 cells are transfected with jetPRIME™ (Polyplus transfection) according to the manufacturer's protocol. Twenty-four hours post-transfection, the cells are washed and incubated in serum-free medium. Conditioned media containing the sdAbs are collected 24 hours later. The level of sdAbs (V5) in conditioned media is quantified by ELISA using an antibody against V5-tag.

Detection by Western Blot.

Cells are washed 3× in phosphate-buffered saline (PBS) and lysed in complete RIPA buffer (50 mM Tris/HCl, pH 8.0, 1% (v/v) Nonidet P40, 0.5% sodium deoxycholate, 150 mM NaCl and 0.1% (v/v) SDS) supplemented with 1× Complete Protease Inhibitor Mixture (Roche Applied Science). Proteins are separated by 8% SDS-polyacrylamide gel electrophoresis and blotted on polyvinylidene difluoride (PVDF, Perkin Elmer) membranes (GE Healthcare), which were blocked for 1 h in TBS-T (50 mM Tris-HCl, pH 7.5, 150 mM NaCl, 0.1% Tween-20) containing 5% nonfat dry milk. Membranes are then incubated 3 h in 1% nonfat milk with a polyclonal hPCSK9 antibody (1:2500) and human LDLR antibody (1:1000, R&D Systems). Appropriate horseradish peroxidase-conjugated secondary antibody (1:10,000, Sigma) is used for detection with enhanced chemiluminescence using the ECL plus kit (GE Healthcare).

Fluorescence-Activated Cell Sorting (FACS) Quantification of Cell Surface LDLR Levels.

HuH7 cells are incubated for 1-4 h at 37° C. with various PCSK9 constructs in the presence or absence of the added compound(s), and then washed 3× with calcium/magnesium free Dulbecco's phosphate-buffered saline (DPBS) containing 0.5% bovine serum albumin (Sigma) and 1 g/l glucose (solution A). Cells are then incubated 5 min at 37° C. with 500 μl of 1× Versene™ solution (Invitrogen) and layered on 5 ml of solution A. Cells are then centrifuged for 5 min at 1000 rpm and re-suspended in 1 ml of solution A containing 1:100 of monoclonal LDLR antibody C7 directed against human LDLR (mAb-C7, Santa Cruz Biotechnology) for 40 min. Cells are washed once with 5 ml of solution A, centrifuged and re-suspended for 20 min in 1 ml of PBS containing 1:250 of Alexa Fluor 647 donkey anti-mouse (Molecular Probes). Cells are washed and re-suspended in 300 μl of PBS 0.2% of propidium iodide (PI). Viable cells (PI-negative) are then analyzed by FACS for both PI and Alexa Fluor 647 using the FACS BD LSR (BD Biosciences). Immunofluorescence of LDLR in human Huh7 cells. Huh7 cells are plated on Poly-L-Lysine-coated (50 ug/ml) round microscope cover slips 1.12 mm thickness (Fisherbrand 12CIR #1) that are placed in a 24-well cell culture plate. Seeding is performed in DMEM complete media and 6 hours later the media is swapped for the serum-free incubation mixtures (300 ul/well). Cells are then incubated for 18 hours with the mixtures lacking or containing 0.5 ug/ml (~6 nM) of PCSK9 protein (WT or variant e.g., D374Y) either alone or with 50 ug/ml (~3 uM) of purified llama sdAbs. The PCSK9 is used as purified protein or as conditioned medium collected from transfected cells. Prior to addition to the Huh7 cells, the mixture containing PCSK9 and sdAb is pre-incubated for 2 hours at 37° C. At the end of the 18 hours incubation, the Huh7 cells are washed 3× with PBS and then fixed for 10 min with 3.7% paraformaldehyde. For intracellular staining, the cells are permeabilized for 5 min with 0.7% Triton X-100. After an additional 3 washes with PBS, permeabilized or non-permeabilized cells are blocked for 30 min with 1% BSA, followed by overnight incubation at 4° C. with primary antibody (1:200 goat polyclonal anti-hLDLR in 1% BSA, R&D Systems). Following a final 3 washes with PBS, antigen-antibody complexes are revealed by 1-hour incubation at room temperature with Alexa fluor-tagged secondary antibody (green labelling) and mounted in ProLong Gold Antifade Reagent containing DAPI (blue labeling) (Molecular Probes, Invitrogen). Immunofluorescence analyses are performed with a confocal microscope (Zeiss LSM-710).

The sdAbs internalization is tested by immunofluorescence in human Huh7 cells. Huh7 cells are incubated for 18 hours with i) conditioned media containing or not different constructs of PCSK9, ii) conditioned media containing or not the various V5-tagged sdAbs, or iii) with mixtures of both PCSK9-conditioned media and sdAbs(V5)-conditioned media. The presence of V5-tagged sdAbs is revealed by immunofluorescence analysis (described above) under non-permeabilized (cell-surface localization of the sdAb) or permeabilized (intra-cellular localization of the sdAb) conditions using the mAb-V5 (Invitrogen) (1:200, in 1% BSA incubated overnight at 4° C.).

Pull-Down Experiments.

Culture medium harvested from PCSK9 transfected cells (e.g., Huh7, HEK239 cells) alone or mixed with purified sdAbs(6His) are pre-incubated for 2 h at 37° C., followed by immunoprecipitation overnight, at 4° C., using 6.6 ug of anti-His Ab-agarose beads. Supernatants and material eluted from the beads are subjected to PAGE-SDS (6%) and Western blot analysis with anti-h PCSK9 Ab.

Dil-LDL Uptake Cell-Based Assay for PCSK9 Activity.

A cell culture method to assay PCSK9 functional activity on the LDLR was developed measuring cellular LDLR activity as the uptake of fluorescent labeled LDL. HepG2 cells are plated at 20,000 cells/well in 96-well format in RPMI+10% FBS, and on the second day the media is changed to RPMI+10% LPDS with 100 nM statin for 16 h. Cells were then preincubated with recombinant human PCSK9 protein at the levels indicated for 2 h, followed by the addition of 5 μg/mL Dil-LDL for a further 2 h incubation at 37° C. Uptake is stopped by the addition of 4% formaldehyde in 10 μM Hoechst-33342 for 20 min at 20° C. Cells are then washed twice with PBS, and fluorescence was measured for Hoeschst (DNA content) at ex/em 360/460 nm, (dichroic mirror=400 nm) is read. After DNA reading, the cells are lysed in 0.1 N NaOH, 0.1% SDS and shaken for 10 min followed by fluorescence reading for Dil-LDL excitation/emission at 530/580 nm (dichroic mirror=561 nm) on an LJL Analyst instrument. For data analysis, the fluorescence ratio of Dil-LDL/Hoechst 33342 is used to normalize Dil-LDL uptake value to cell count.

Transfections, Biosynthetic Analyses, Immunoprecipitations of PCSK9.

Transfections are done with $3 \times 10^5$ HEK293 cells using Effectene™ (Qiagen) and a total of 0.5 μg of cDNAs. Alternatively, $5 \times 10^5$ HuH7 or $6 \times 10^5$ HepG2 cells are transfected with a total of 4 μg of cDNAs in Lipofectamine™ 2000 (Invitrogen). Two days post-transfection, HEK293 cells are washed and then incubated for various times with either 250 μCi/ml [35S]Met/Cys (PerkinElmer Life Sciences). The cells are lysed in modified RIPA buffer (150 mM NaCl, 50 mM Tris-HCl, pH 7.5), 1% Nonidet P-40, 0.5% sodium deoxycholate, 0.1% SDS, and a protease inhibitor mixture (Roche Applied Science), after which the lysates and media are prepared for immunoprecipitation. The antibodies used are the anti-V5 mAb (Invitrogen, 1:500), and proprietary rabbit anti-PCSK9 31-454 (A-03). Immunoprecipitates are resolved by SDS-PAGE on 8% Tricine gels and autoradiographed. These experiments are repeated at least three times. Quantitation are performed on a Storm Imager™ (Amersham Biosciences) by using the ImageQuant™ version 5.2 software. This sensitive method is testing whether the compound affect propCSK9 to PCSK9 activation in the endoplasmic reticulum and the secretion of active PCSK9 complexed with its prosegment from the cells into the medium.

Cells engineered to express endogenously and stably PCSK9 or its natural mutants are be incubated with the compound(s) and the different PCSK9 forms present in the media and cell lysates are analysed for by Western blot using sensitive human PCSK9 antibodies.

Nucleic Acids, Host Cells

The present invention also relates to nucleic acids comprising nucleotide sequences encoding the above-mentioned PCSK9-binding sdAb. The nucleic acid may be codon-optimized. The nucleic acid can be a DNA or an RNA. The nucleic acid sequence can be deduced by the skilled artisan on the basis of the disclosed amino acid sequences.

The present invention also encompasses vectors (plasmids) comprising the above-mentioned nucleic acids. The vectors can be of any type suitable, e.g., for expression of said polypeptides or propagation of genes encoding said polypeptides in a particular organism. The organism may be of eukaryotic or prokaryotic origin. The specific choice of vector depends on the host organism and is known to a person skilled in the art. In an embodiment, the vector comprises transcriptional regulatory sequences or a promoter operably-linked to a nucleic acid comprising a sequence encoding a PCSK9-binding sdAb of the invention. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequence. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory sequences" or "transcriptional regulatory elements" are generic terms that refer to DNA sequences, such as initiation and termination signals, enhancers, and promoters, splicing signals, polyadenylation signals, etc., which induce or control transcription of protein coding sequences with which they are operably-linked.

A recombinant expression vector comprising a nucleic acid sequence of the present invention may be introduced into a cell, e.g., a host cell, which may include a living cell capable of expressing the protein coding region from the defined recombinant expression vector. Accordingly, the present invention also relates to cells (host cells) comprising the nucleic acid and/or vector as described above. The suitable host cell may be any cell of eukaryotic or prokaryotic (bacterial) origin that is suitable, e.g., for expression of the sdAbs or propagation of genes/nucleic acids encoding said sdAbs. The eukaryotic cell line may be of mammalian, of yeast, or invertebrate origin. The specific choice of cell line is known to a person skilled in the art. Choice of bacterial strain will depend on the task at hand and is known to a person skilled in the art. The terms "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein. Vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), Sambrook and Russell (supra) and other laboratory manuals. Methods for introducing nucleic acids into mammalian cells in vivo are also known, and may be used to deliver the vector DNA of the invention to a subject for gene therapy.

The above-mentioned nucleic acid or vector may be delivered to cells in vivo (to induce the expression of the single domain antibody) using methods well known in the art such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo. A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor. Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes.

Defective retroviruses are well characterized for use as gene therapy vectors (for a review see Miller, A. D. (1990) *Blood* 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psiCrip, psiCre, psi2 and psiAm. Retroviruses have been used to introduce a variety of genes into many different cell types, including epithelial cells, endothelial cells, lymphocytes, myoblasts, hepatocytes, bone marrow cells, in vitro and/or in vivo.

For use as a gene therapy vector, the genome of an adenovirus may be manipulated so that it encodes and expresses a nucleic acid of the invention (e.g., a nucleic acid encoding a PCSK9-binding sdAb), but is inactivated in terms of its ability to replicate in a normal lytic viral life cycle. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells, hepatocytes, and muscle cells.

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle. AAV may be used to integrate DNA into non-dividing cells. Lentiviral gene therapy vectors may also be adapted for use in the invention.

The present invention also relates to a method of producing the PCSK9-binding sdAbs of the present invention, comprising cultivating the above-mentioned host cells under conditions permitting expression of the sdAbs, and collecting (e.g., in the culture medium) the sdAbs expressed from the cell population. In an embodiment, the method further comprises submitting the collected sdAbs to one or more steps of enrichment/purification.

Pharmaceutical Compositions

In another aspect, the present invention provides a composition, e.g., a pharmaceutical composition, containing one or a combination of PCSK9-binding sdAbs of the present invention, formulated together with a pharmaceutically acceptable carrier and/or excipient.

Such compositions may include one or a combination of (e.g., two or more different) sdAbs. For example, a pharmaceutical composition of the invention can comprise a combination of PCSK9-binding sdAbs that bind to different epitopes on the target antigen and/or that have complementary activities.

Pharmaceutical compositions of the invention also can be administered in combination therapy, i.e., combined with other agents. For example, the combination therapy can include a PCSK9-binding sdAb combined with at least one other cholesterol-reducing agent. Examples of therapeutic agents that can be used in combination therapy are described in greater detail below.

As used herein, "pharmaceutically acceptable carrier" or "pharmaceutically acceptable excipient" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active sdAb may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M. et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable antioxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers or excipients include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition.

Prolonged absorption of the injectable compositions can be brought about by including in the composition an agent that delays absorption for example, monostearate salts and gelatin.

Sterile injectable solutions can be prepared by incorporating the active compound (e.g., PCSK9-binding sdAb) in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient (e.g., PCSK9-binding sdAb) which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the PCSK9-binding sdAb, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for PCSK9-binding sdAbs of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more sdAbs with different binding affinities and/or specificities are administered simultaneously, in which case the dosage of each sdAbs administered falls within the ranges indicated. The sdAb is usually administered on multiple occasions. Intervals between single dosages can be, for example, weekly, monthly, every three months or yearly. Intervals can also be irregular as indicated by measuring blood levels of sdAb in the patient. In some methods, dosage is adjusted to achieve a plasma concentration of the sdAb of about 1-1000 µg/ml and in some methods about 25-300 µg/ml.

Alternatively, a PCSK9-binding sdAb can be administered as a sustained release formulation, in which case less frequent administration is required. Dosage and frequency vary depending on the half-life of the sdAb in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response (e.g., decreased plasma LDL/cholesterol levels) for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" or "effective amount" or "therapeutically effective dosage" of PCSK9-binding sdAbs of the invention can result in a lowering of LDL-C level in a subject, a decrease in severity of at least one disease symptom (e.g., a decrease in plasma LDL-cholesterol, or a decrease in a symptom of a LDL-cholesterol-related disorder), an increase in frequency and duration of disease symptom-free periods, or a prevention of impairment or disability due to the disease affliction in the subject.

A composition of the present invention can be administered by one or more routes of administration using one or more of a variety of methods known in the art. As will be appreciated by the skilled artisan, the route and/or mode of administration will vary depending upon the desired results. Routes of administration for sdAb of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion. Alternatively, a PCSK9-binding sdAb of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. Therapeutic compositions can be administered with medical devices known in the art. For example, in one embodiment, a therapeutic composition of the invention can be administered with a needleless hypodermic injection device.

In certain embodiments, the sdAb of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. The liposomes may comprise one or more moieties which are selectively transported into specific cells, tissues or organs, thus enhance targeted drug delivery (see, e.g., V. V. Ranade, 1989 *J. Clin. Pharmacol.* 29:685). In an embodiment, the sdAb of the invention can be formulated to be delivered to the liver (i.e., to hepatocytes).

Uses of the sdAbs

PCSK9 has been implicated in cholesterol homeostasis, as it appears to have a specific role in cholesterol biosynthesis or uptake. In a study of cholesterol-fed rats, it was reported that PCSK9 was downregulated in a similar manner to other genes involved in cholesterol biosynthesis, (Maxwell et al., 2003 *J Lipid Res.* 44:2109-2119). PCSK9 expression has been found to be upregulated by statins in a manner attributed to the cholesterol-lowering effects of the drugs (Dubuc et al., 2004, *Arterioscler Thromb Vasc Biol.* 24: 1454-1459). Adenoviral expression of PCSK9 results in a time-dependent increase in circulating low density lipoprotein (LDL) cholesterol (LDL-C) (Benjannet et al., 2004 *J. Biol. Chem.* 279:48865-48875), and mice with PCSK9 gene deletions have increased levels of hepatic LDL receptors (LDLR) and clear LDL-C from the plasma more rapidly (Rashid et al., 2005 supra). Medium from HepG2 cells which are transiently transfected with PCSK9 is found to reduce the amount of cell surface LDLRs and internalization of LDL-C when transferred to untransfected HepG2 cells (Cameron et al., 2006 *Human Mol. Genet.* 15:1551-1558). Additionally, purified PCSK9 added to the medium of HepG2 cells reduced the number of cell-surface LDLRs in a dose- and time-dependent manner (Lagace et al., 2006, supra).

A number of mutations in the gene PCSK9 have been associated with autosomal dominant hypercholesterolemia (ADH), an inherited metabolism disorder which is characterized by marked elevations of LDL-C particles in the plasma that can lead to premature cardiovascular failure (e.g., Abifadel et al, 2003 *Nat. Genetics* 34:154-156; Tirnms et al, 2004 *Hum. Genetics* 114:349-353; Leren, 2004 *Clin. Genet.* 65:419-422).

Expression or upregulation of PCSK9 is associated with increased plasma levels of LDL-C, and inhibition or the lack of expression of PCSK9 is associated with low LDL-C plasma levels and lower levels of LDL-C associated with sequence variations in PCSK9 confer protection against coronary heart disease (Cohen, et al, 2006 *N. Engl. J. Med.* 354:1264-1272).

The PCSK9-binding sdAbs described herein have in vitro and in vivo diagnostic and therapeutic utilities. For example, these molecules can be administered to cells in culture, e.g., in vitro or ex vivo, or in a subject in need thereof, e.g., in vivo, to treat, prevent or diagnose a variety of disorders associated with PCSK9 activity/function.

PCSK9-binding sdAbs are particularly suitable for treating human patients having, or at risk for, elevated cholesterol or a condition associated with elevated cholesterol (e.g., LDL cholesterol), including a lipid disorder (e.g., hyperlipidemia, hypercholesterolemia, xanthomatosis).

PCSK9-binding sdAbs may also be suitable for treating human patients having ateriosclerotic conditions (e.g., atherosclerosis), coronary artery disease, cardiovascular disease, stroke, ischemia, peripheral vascular diseases, and prophylactically for patients at risk for these disorders, e.g., due to the presence of one or more risk factors (e.g., hypertension, cigarette smoking, diabetes, obesity, or hyperhomocysteinemia).

As used herein the terms "LDL-cholesterol-related diseases or disorders" refer to diseases or conditions resulting in part from a high level of circulating LDL-cholesterol in the blood stream. Without being so limited, LDL-cholesterol-related diseases or disorders include hyperlipidemia, hypercholesterolemia, xanthomatosis and cardiovascular diseases such as ateriosclerotic conditions (e.g., atherosclerosis), coronary artery disease, cardiovascular disease, stroke, ischemia, peripheral vascular diseases.

When PCSK9-binding sdAbs are administered together with another agent, the two can be administered sequentially in either order or simultaneously (in the same composition or in different compositions). In some embodiments, a PCSK9-binding sdAb is administered to a subject who is also receiving therapy with a second agent useful for treating the disease/condition (e.g., a second cholesterol-reducing agent). Cholesterol reducing agents include statins, bile acid sequestrants, niacin, fibric acid derivatives, and long chain alpha, omego-dicarboxylic acids. Statins inhibit cholesterol synthesis by blocking HMGCoA, a key enzyme in cholesterol biosynthesis. Bile acid sequestrants interrupt the recycling of bile acids from the intestine to the liver. Examples of active ingredients that may be administered in combination with of the present invention include, but are not limited to, other compounds which improve a patient's lipid profile, such as (a) HMG-CoA reductase inhibitors, (e.g., statins, including lovastatin, simvastatin, fluvastatin, rosuvastatin, pravastatin, rivastatin, atorvastatin, itavastatin, pitavastatin, cerivastatin and other statins), (b) cholesterol absorption inhibitors, such as stenol esters, beta-sitosterol, sterol glycosides such as tiqueside; and azetidinones, such as ezetimibe, (c) inhibitors of cholesterol ester transport protein (CETP) (e.g., anacetrapib or dalcetrapib) which are now in clinical trials to increase HDL and decrease LDL cholesterol, (d) niacin and related compounds, such as nicotinyl alcohol, nicotinamide, and nicotinic acid or a salt thereof, (e) bile acid sequestrants (cholestyramine, colestipol (e.g., colestipol hydrochloride), dialkylaminoalkyl derivatives of a cross-linked dextran, Colestid®, LoCholest®, (f) acyl CoA:cholesterol acyltransferase (ACAT) inhibitors, such as avasimibe and melinamide, and including selective ACAT-1 and ACAT-2 inhibitors and dual inhibitors, (g) PPARy agonists, such as gemfibrozil and fenofibric acid derivatives (fibrates), including clofibrate, fenofibrate, bezafibrate, ciprofibrate, and etofibrate, (h) microsomal triglyceride transfer protein (MTP)/ApoB secretion inhibitors, (i) anti-oxidant vitamins, such as vitamins C and E and beta carotene, (k) thyromimetics, (l) LDL receptor inducers, (m) platelet aggregation inhibitors, for example glycoprotein IIb/IIIa fibrinogen receptor antagonists and aspirin, (n) vitamin B 12 (also known as cyanocobalamin), (o) folic acid or a pharmaceutically acceptable salt or ester thereof, such as the sodium salt and the methylglucamine salt, (p) FXR and LXR ligands, including both inhibitors and agonists, (q) agents that enhance ABCA1 gene expression, and (r) ileal bile acid transporters.

A combination therapy regimen may be additive, or it may produce synergistic results (e.g., reductions in cholesterol greater than expected for the combined use of the two agents). In some embodiments, combination therapy with a PCSK9-binding sdAb and a cholesterol-reducing agent (e.g., a statin, fibrates, ezetimibe or a combination thereof) produces synergistic results (e.g., synergistic reductions in cholesterol). In some subjects, this can allow reduction in the dosage of the cholesterol-reducing agent to achieve the desired cholesterol levels. PCSK9-binding sdAbs may be useful for subjects who are intolerant to therapy with another cholesterol-reducing agent, or for whom therapy with another cholesterol-reducing agent has produced inadequate results (e.g., subjects who experience insufficient LDL-C reduction on statin therapy).

A PCSK9-binding sdAb described herein can be administered to a subject with elevated cholesterol (e.g., LDL-cholesterol) (e.g., a human subject with total plasma cholesterol levels of 200 mg/dl or greater, a human subject with LDL-C levels of 160 mg/dl or greater).

In an embodiment, the PCSK9-binding sdAb of the invention can be used to detect levels of PCSK9. This can be achieved, for example, by contacting a sample (e.g., a biological sample such as blood, serum, plasma, or a cell sample) with the PCSK9-binding sdAb under conditions that allow for the formation of a complex between the PCSK9-binding sdAb and PCSK9. Any complexes formed between the molecule and PCSK9 are detected and compared in the sample and in a control sample. For example, standard detection methods, well known in the art, such as ELISA and flow cytometric assays, can be performed using the PCSK9-binding sdAb of the invention.

Accordingly, in one aspect, the invention further provides methods for detecting the presence of PCSK9 (e.g., hPCSK9) in a sample, or measuring the amount of PCSK9 (e.g., active form of PCSK9), comprising contacting the sample with a PCSK9-binding sdAb of the invention, under conditions that allow for formation of a complex between the sdAb and PCSK9. The formation of a complex is then detected, wherein a difference in complex formation between the sample compared to a control sample is indicative of the presence of PCSK9 in the sample.

Also within the scope of the invention are kits comprising a sdAb of the invention, or the compositions of the invention and instructions for use. The kit can further contain a least one additional reagent, or one or more additional sdAbs of the invention. Kits typically include a label indicating the intended use of the contents of the kit. The term label includes any writing, or recorded material supplied on or with the kit, or which otherwise accompanies the kit. The kit may further comprise one or more container(s), reagent(s), administration device(s) (e.g., a syringe).

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

MODE(S) FOR CARRYING OUT THE INVENTION

The present invention is illustrated in further details by the following non-limiting examples.

Example 1: Production and Purification of Recombinant PCSK9 Protein

PCSK9-(His)$_6$ was produced in large quantities from 35 L baculovirus High Five™ cells and subjected to multiple steps of purification including Ni$^{2+}$-affinity followed by mono-Q™ anion exchange and finally gel filtration chromatography. Coomassie blue staining of 18 µg total proteins from each preparation separated on a 4-12% gradient in MES buffer SDS-PAGE under non-reducing conditions are shown in FIG. 1A. The position of the molecular size markers (M), total proteins in the High Five™ supernatant (S) before purification, purification by Ni$^{2+}$-affinity chromatography (Ni), SOURCE™ 15Q anion exchange (Q), and Superdex™ 200 gel filtration (GF). M: Mark 12 (25 µl); S, Supernatant (10 µl); Ni, Ni-NTA Pool (18 µg); Q, SOURCE Q Pool (18 µg); GF, Gel-filtration Pool of batch 7 (18 µg), GFB: Gel-filtration Pool of batch 7B (18 µg), GFCP, Gel-filtration Pool of batch 7CP (18 µg).

Example 2: Immunization of Llama with Purified PCSK9 Proteins

Figure 1B:
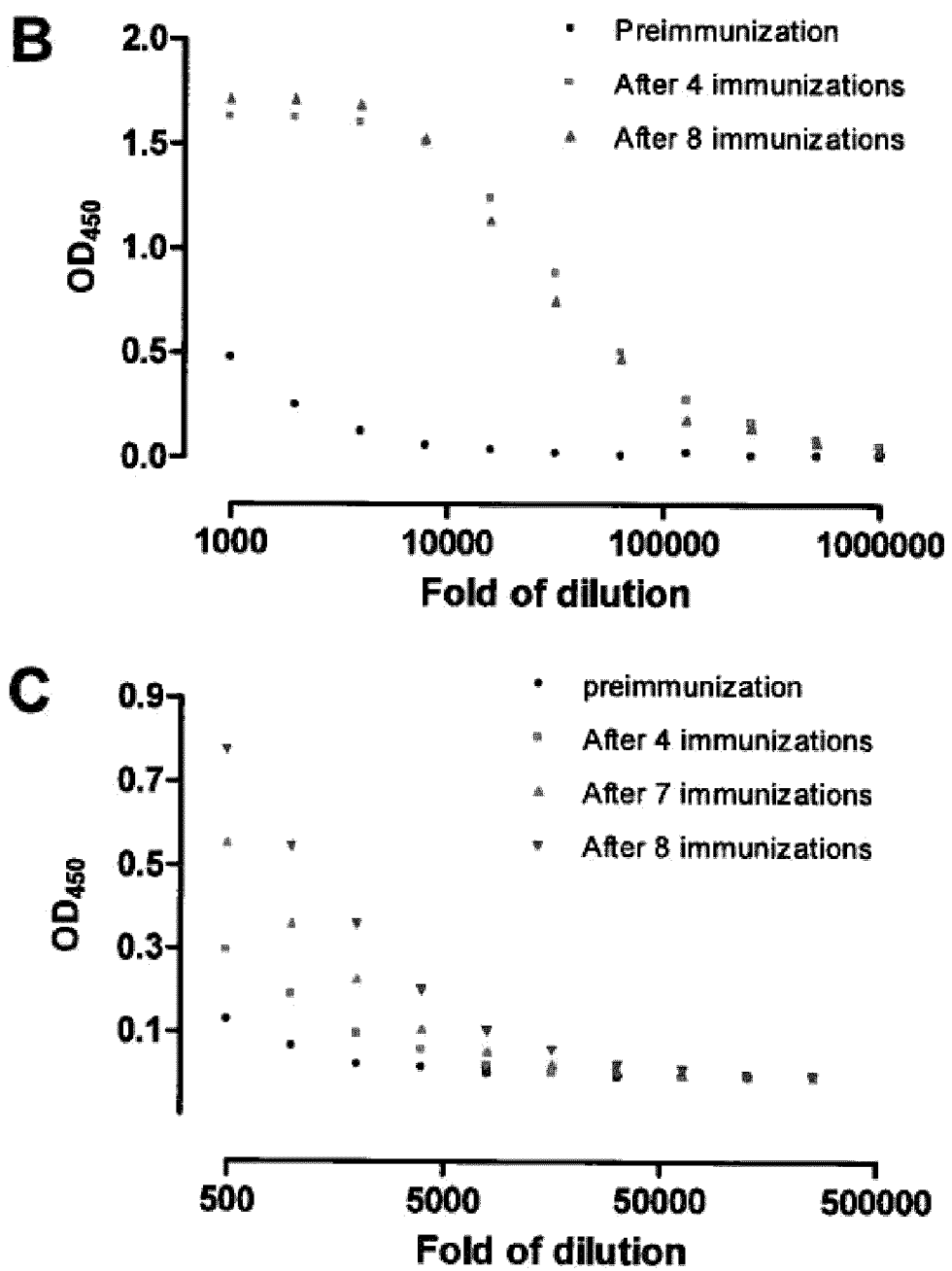

Isolation from immune phage display library is the easiest way to generate high affinity sdAbs. This involves immunization of a llama with the antigen; monitor the immune response; construction of phage display library and subsequent phage display panning. Several injections of human purified PCSK9 heterodimer complexes formed of the prosegment (amino acids 31 to 152) and the catalytic subunit (amino acids 153 to 692) were used to immunize llama. Immunization response was monitored and characterized using reactivity against PCSK9. FIGS. 1B and 1C show immune response in llama. While in [B] immune response by the llama after 4 and 8 immunizations is evident, in [C] the results suggest that the 4 and 8 immunizations are indeed different when a lower concentration of antigen (PCSK9) was used—an indication that very high affinity Abs may exist after 8 wks immunization. After immunizing a llama with a total of 1 mg of pure human PCSK9, for 4× immunizations, 2×10$^8$ lymphocytes were collected, respectively, from the animal and used as starting material for library construction. cDNA was synthesized from RNA isolated from the lymphocytes.

Example 3: Screening for V$_H$H Domains (sdAbs) Specific for PSCK9

Using primers specific for both V$_H$/V$_H$H and the hinge regions of camelid IgGs, DNA encoding V$_H$ as well V$_H$H was amplified. The V$_H$H fragments were separated from V$_H$ based on their sizes. The V$_H$H genes were amplified using primers specific for V$_H$H and cloned into a phagemid-based phage display vector. More specifically, three different sense primers (called J' and corresponding to the 5'-end of IgG) including MJ1 (GCCCAGCCGGCCATGGCCSMKGT-GCAGCTGGTGGAKTCTGGGGGA (SEQ ID NO: 144)), MJ2 (CAGCCGGCCATGGCCCAGGTAAAGCTGGAG-GAGTCTGGGGGA (SEQ ID NO: 145)) and MJ3 (GC-CCAGCCGGCCATGGCCCAGGCTCAGGTACAGCTG-GTGGAGTCT (SEQ ID NO: 146)) and two anti-sense primers, corresponding to the CH2 domain DNA sequence, CH2 (CGCCATCAAGGTACCAGTTGA (SEQ ID NO: 147)) and CH2b3 (GGGGTACCTGTCATCCACGGAC-CAGCTGA (SEQ ID NO: 148)) were used to amplify the VH-CH1-Hinge-CH2 region of conventional IgG or V$_H$H-Hinge-CH2. Amplified V$_H$H products of approximately 600 bp from the primer combination J'-CH2 were extracted from a 1% agarose gel and purified with a QIAquick™ Gel Extraction Kit (Qiagen) and the amplified products from primers J'-CH2b3 were PCR purified. In a second PCR reaction, two primers, MJ7BACK (CATGTGTA-GACTCGCGGCCCAGCCGGCCATGGCC (SEQ ID NO:

149)) and MJ8FOR (CATGTGTAGATTCCTGGCCGGC-CTGGCCTGAGGAGACGGTGACCTGG (SEQ ID NO: 150)), were used to introduce SfiI restriction sites and to amplify the final sdAb fragments from the combined J'-CH2 and J'-CH2b3 amplified products. The final PCR product was digested with SfiI and ligated into pMED1 (A. Bell, et al. *Cancer Letters* 289:81-90) and transformed into *E. coli* TG1 (New England Biolabs, Ipswich, Mass.) by electroporation. A large number of transformations were performed to make a high diversity library. The actual size of the library was measured as 2×10$^8$ independent transformants, exceeding the number of lymphocytes used for library construction. Helper phages M13KO7 (NEB) were added to exponentially grow a phagemid library to "rescue" the phage, meaning enabling the *E. coli* cells to produce all necessary proteins for phage particle auto-assembly by providing most required components missing in the phagemid constructs. Over a total of 2.3×10$^8$ candidate llama sdAbs screened, 50 sdAbs that specifically bind PCSK9 were selected and further characterized.

Example 4: Expression and Purification of sdAbs Specific for PCSK9

Following their selection, DNAs from the 47 sdAbs were subcloned into an expression vector, and recombinant proteins (r-proteins) were purified. Even though transfection of mammalian cells is a well-known technique that is widely used on a small scale for the production of microgram quantities of r-proteins, only recently this technique has been made possible at large-scale. Large-scale transfection of Human Embryonic Kidney 293 (HEK293), and to a lesser extent of Chinese Hamster Ovary (CHO) cells, is becoming a well established enabling technology allowing the production of milligram to grams quantities of r-proteins within a few days after cDNA cloning into an appropriate expression vector (Atkinson, A., Jack, G. W. (1973). *Biochimica et Biophysica Acta*, 308(7):41-52; Baldi, L., et al. (2007). *Biotechnology Letters*, 29(5): 677-684; Wurm, F., Bernard, A. (1999). *Current Opinion in Biotechnology*, 10(2):156-159). Combined with the use of expression vectors bearing the Epstein-Barr virus origin of replication (oriP), a 3-fold improvement in r-protein yield is generally obtained over a similar non-oriP vector (Berntzen, G. et al. (2005). *Journal of Immunological Methods*, 298(1-2): 93-104; Durocher, Y., Perret, S., Kamen, A. (2002). *Nucleic Acids Research*, 30(2):E9). When using a HEK293-EBNA1 cell line adapted to suspension culture in serum-free medium in combination with a highly potent expression plasmid vector, high level expression of recombinant proteins is usually obtained.

Figure 6A:
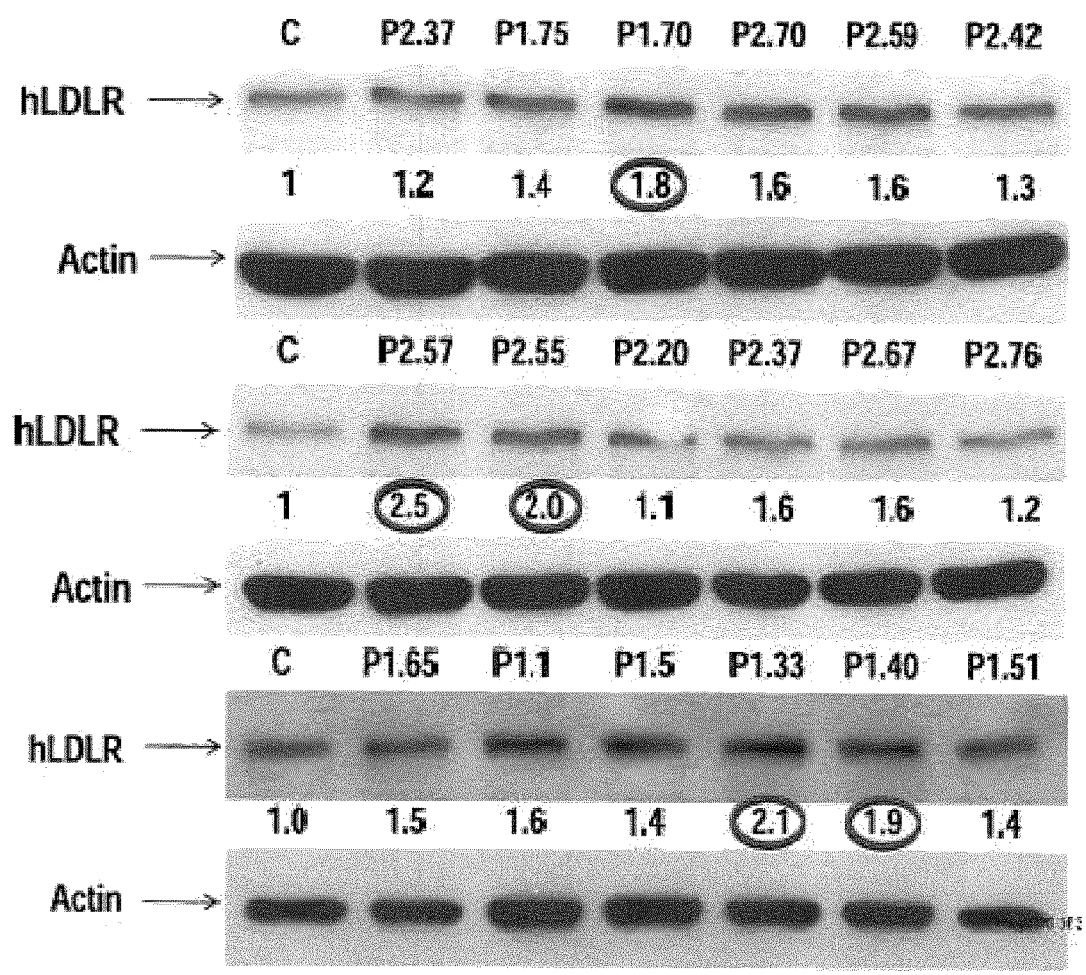
FIG. 6 [A] and [B] show LDLR expression in HepG2 cells following incubation with various single domain antibodies, as assessed by Western blot.
Figure 6B:
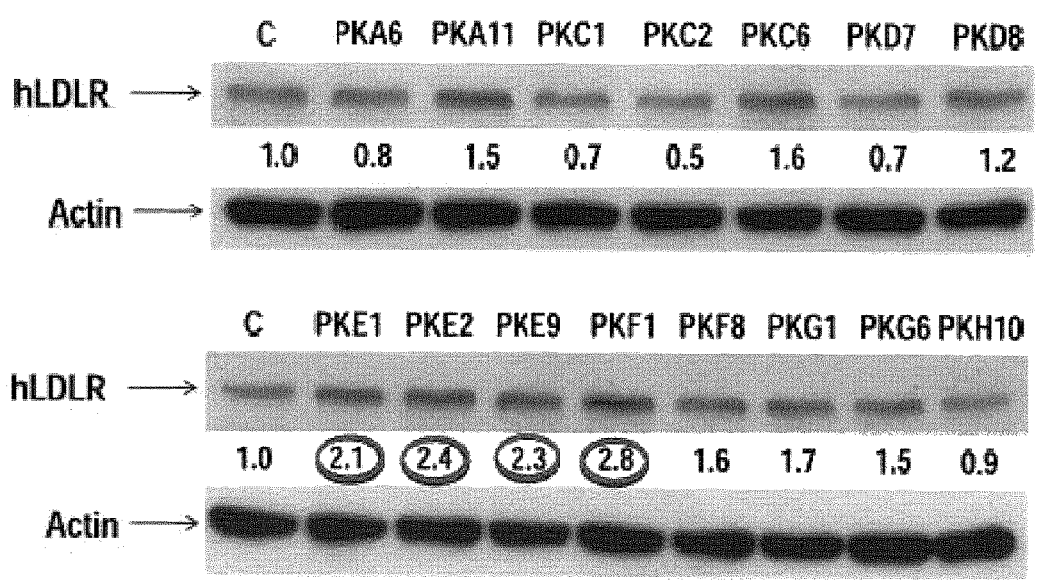
Figure 7:
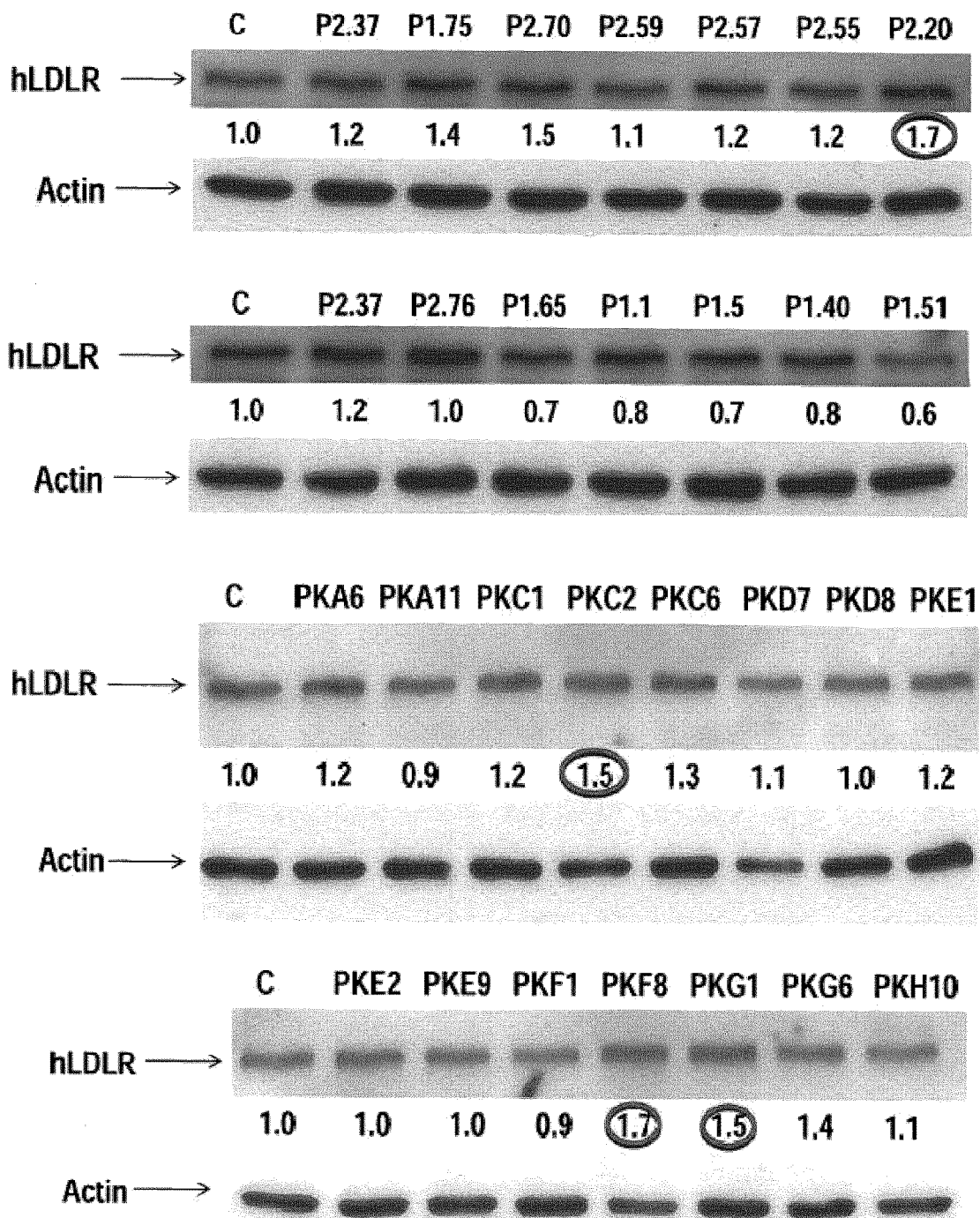
FIG. 7 shows LDLR expression in HuH7 cells following incubation with single domain antibodies, as assessed by Western blot.
Figure 8A:
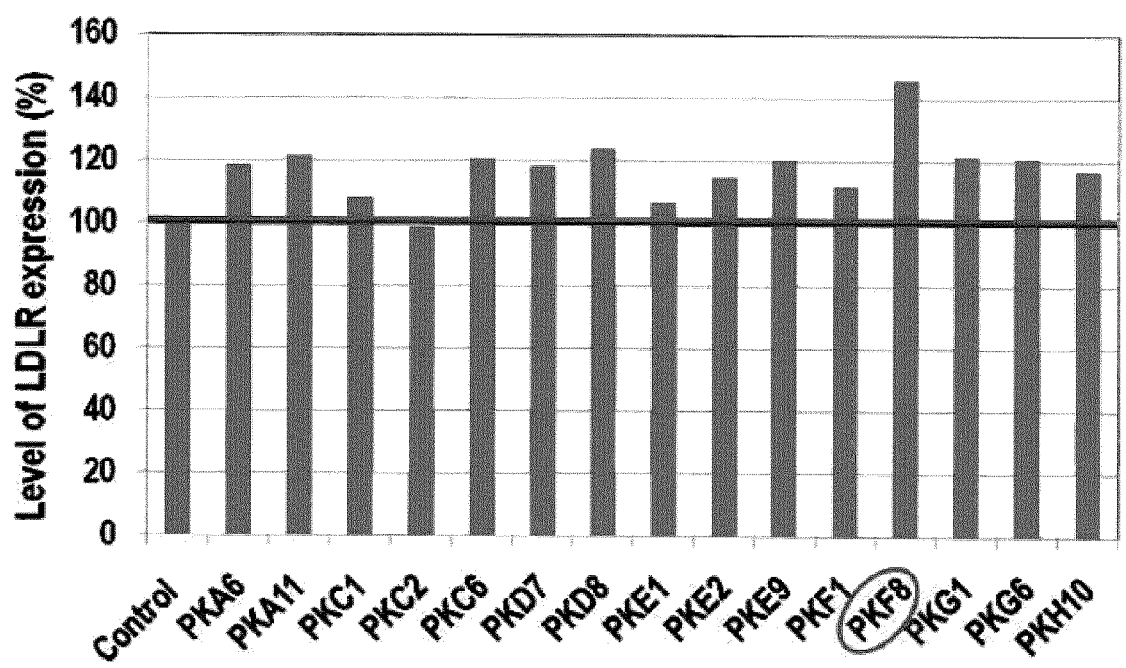
FIG. 8 depicts the most effective antibodies according to the Western blot analyses of FIGS. 6 and 7, presented as [A] a histogram; and [B] LDLR expression fold.
Figure 10:
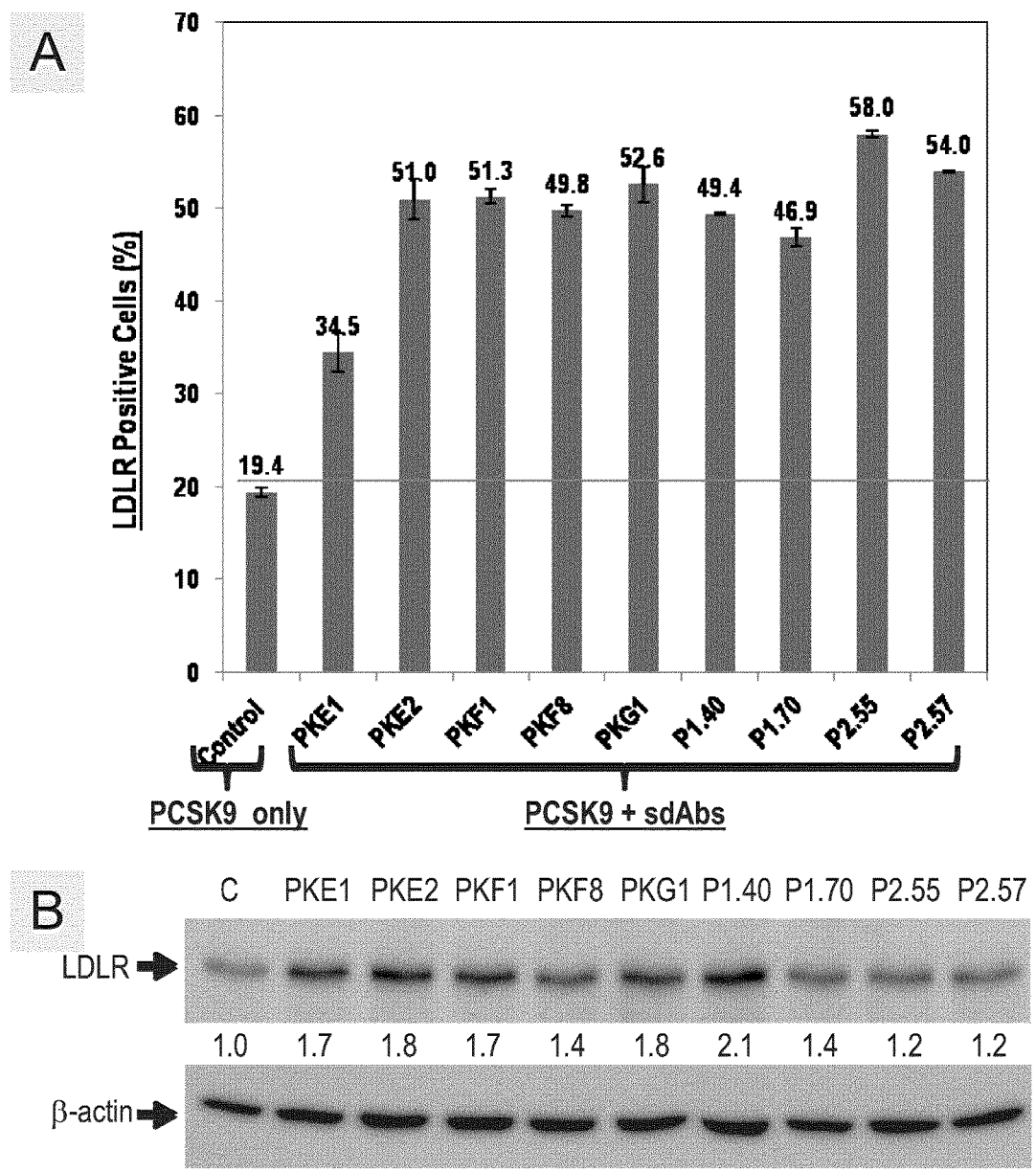
FIG. 10 shows the effect of sdAbs on WT PCSK9-induced LDLR degradation. Naive HuH7 cells were incubated with 1 μg/mL of purified WT PCSK9 for 24 h in the absence (Control) or presence of 50 μg/mL of various sdAbs to PCSK9. The cells were then detached and analyzed by [A] flow cytometry for cell surface LDLR (LDLR positive cells %); [B] Western blot for total LDLR, compared to β-actin control. The numbers represent the ratio of LDLR levels compared to β-actin control; or [C] flow cytometry of cell surface LDLR (level of LDLR Expression (A.U.)). In [D] naive HuH7 cells were incubated for 18 h in the absence [Cnt(−)] or presence of 0.7 ug/ml (~9 nM) WT PCSK9 protein alone [Cnt(+)] or mixed with 50 ug/ml (~3 uM) of various purified llama sdAbs, as indicated. The WT PCSK9 protein was used as conditioned media from transiently transfected Huh7 cells and was quantified by ELISA. Prior to addition to the Huh7 cells, the mixtures were pre-incubated for 2 h at 37° C. The level of LDLR at the cell surface was measured by FACS using anti-human LDLR antibody and a suitable secondary antibody labeled with alexa 647. Cell surface LDLR is reported relative to Cnt(−). % inhibition of PCSK9 activity was calculated as [sdAb−Cnt(+)]/[Cnt(−)−Cnt(+)]×100.

Example 5: Selection and Characterization of sdAbs Inhibiting the PCSK9-Dependent LDLR Degradation The 6×His tagged sdAbs were overexpressed and purified from HEK293 cells in amounts of about 1 mg/L. In some experiments, culture medium collected from sdAb-V5 transfected HEK293 cells were used as source of sdAbs. Each sdAb was tested for its ability to inhibit the LDLR enhanced degradation of 1 µg/ml of wild type PCSK9 added to the extracellular milieu of the human hepatocyte cell lines HepG2 and HuH7. As exemplified in HepG2 (FIGS. 6 and 8) and Huh7 (FIGS. 7, 8 and 10B) cell lines using Western blot analyses as described in Benjannet S. et al. *J. Biol. Chem.* 285: 40965-40978, 2010, several tested sdAbs inhibit the PCSK9-dependant LDLR degradation. The inhibition of the PCSK9 function is detected by an increase of LDLR expression.

Figure 9:
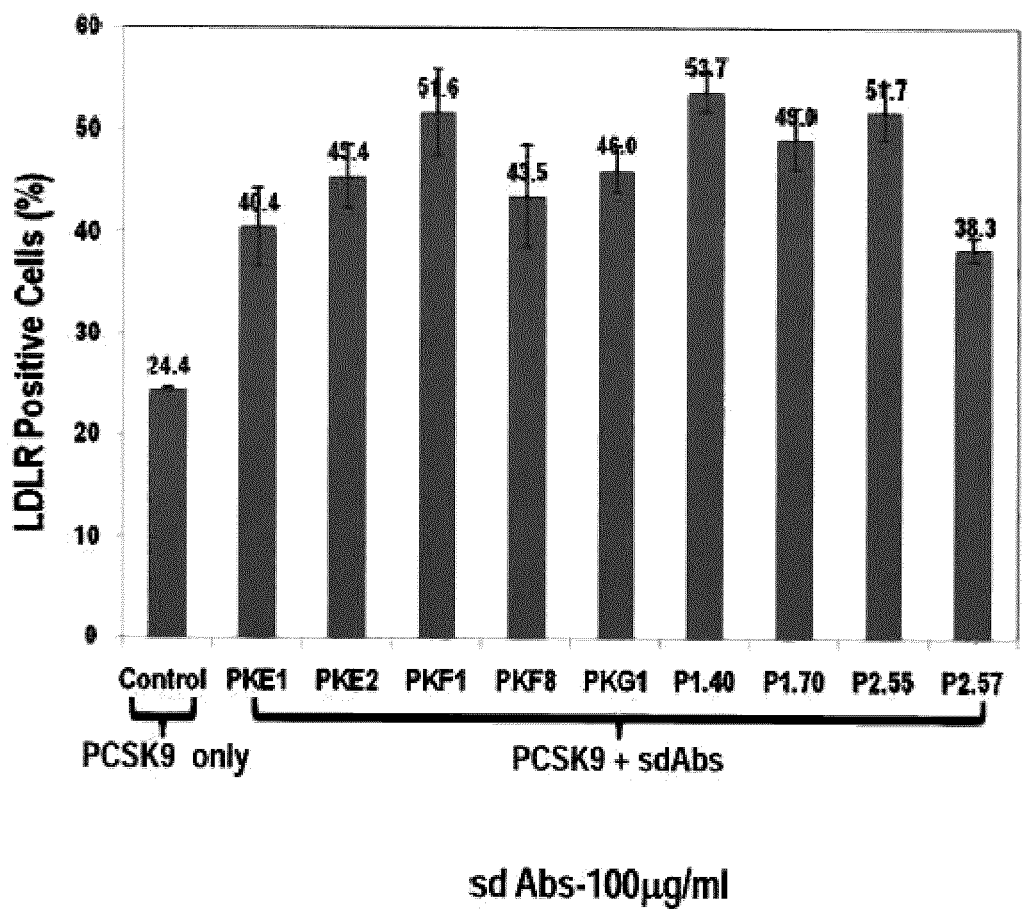
FIG. 9 shows the effect of sdAbs on wild type (WT) PCSK9-induced LDLR degradation. Naive HuH7 cells were incubated with 1 ug/mL of purified WT PCSK9 for 24 h in the absence (Control) or presence of 100 μg/mL of various sdAbs to PCSK9. The cells were then detached and analyzed by flow cytometry for cell surface LDLR (LDLR positive cells %)
Figure 10C:
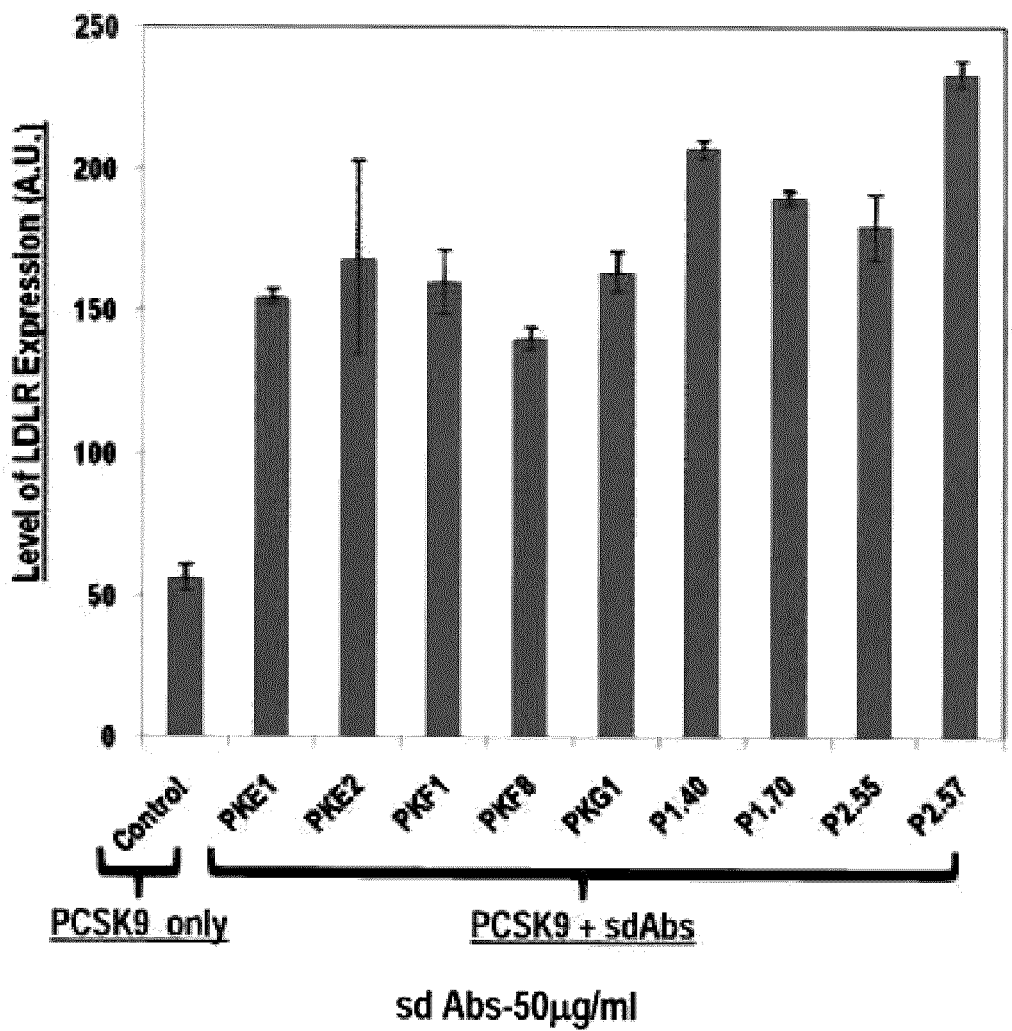

As exemplified in Huh7 cells, the presence of selected sdAbs was also shown to prevent the activity of PCSK9 on LDLR at the cell surface by using flow cytometry analyses as described in Benjannet S. et al., 2010, supra. The inhibition of the PCSK9 function in these assays is detected by an increased number of positive cells which correlated with an increased expression of LDLR at the cell surface. The analyses were performed either using a purified form of PCSK9-WT protein (FIGS. 9, 10A and 10C) or culture medium derived from WT (FIG. 10D) or D374Y (FIG. 11) PCSK9 transfected Huh7 cells and HEK293 cells, respectively.

Figure 10D:
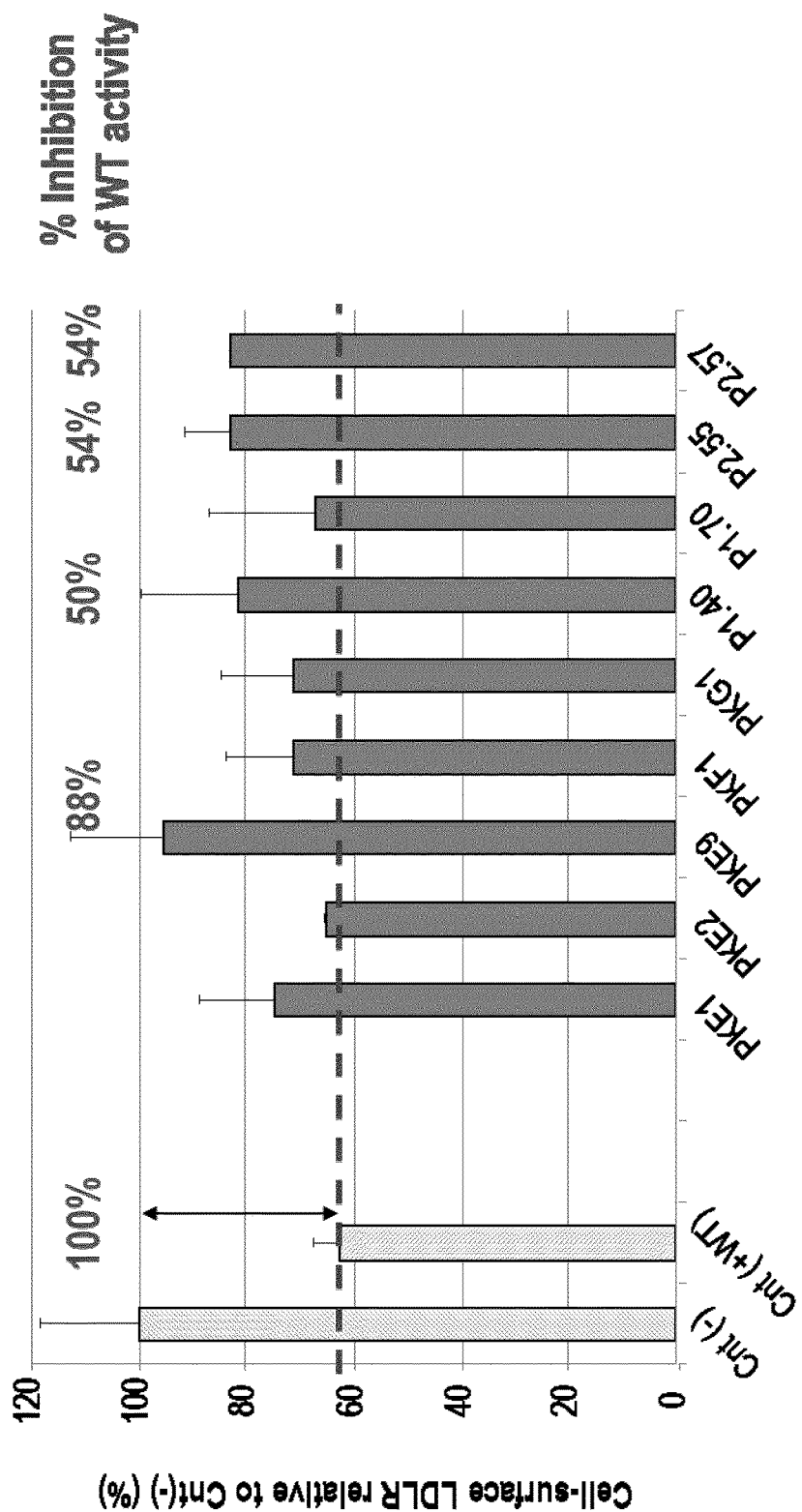

In FIG. 10D, naive HuH7 cells were incubated for 18 h in the absence [Cnt(−)] or presence 0.7 ug/ml (~9 nM) PCSK9-WT protein (as conditioned media from transfected Huh7 cells) alone [Cnt(+)] or mixed with 50 ug/ml (~3 uM) of various purified llama sdAbs. Prior to addition to the cells, the mixtures were pre-incubated for 2 h at 37° C. The level of LDLR at the cell surface was measured by FACS using anti human LDLR antibody and a suitable secondary antibody labeled with alexa 647. Cell surface LDLR is reported relative to Cnt(−). % inhibition of PCSK9 activity was calculated as [sdAb−Cnt(+)]/[Cnt(−)−Cnt(+)]×100. As shown, 4 sdAbs were able to inhibit the activity of PCSK9-WT by 54 to 88%.

Figure 11A:
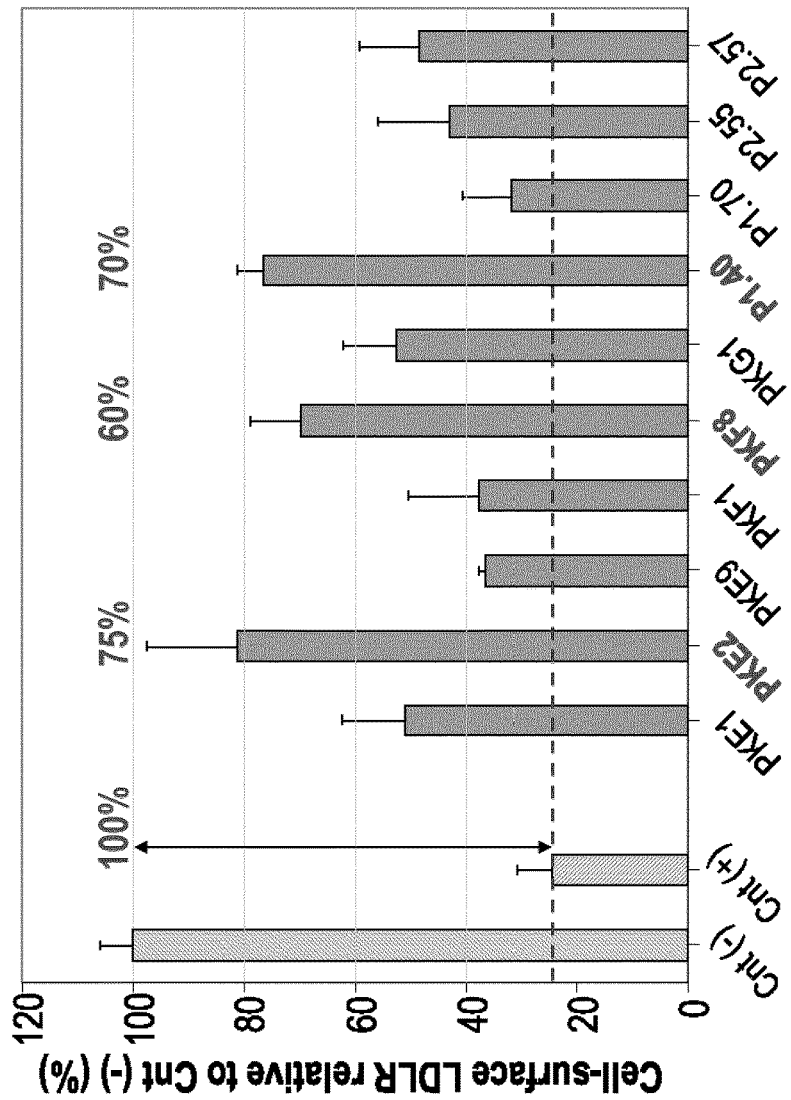
FIG. 11 shows the effect of sdAbs on the gain-of-function PCSK9-D374Y-induced LDLR degradation. [A] Naive Huh7 cells were incubated for 18 h in the absence [Cnt(−)] or presence of 0.5 ug/ml (~6 nM) PCSK9-D374Y protein alone [Cnt(+)] or mixed with 50 ug/ml (~3 uM) of various purified llama sdAbs, as indicated. Data represents the average of three independent experiments performed in duplicate; and [B] Naive Huh7 cells were incubated for 18 h in the absence [Cnt(−)] or presence of 0.5 ug/ml (~6 nM) PCSK9-D374Y protein alone [Cnt(+)] or mixed with increasing concentrations of PKE2, P1.40 or PKF8 sdAbs as indicated. Data represents an average of two independent experiments performed in duplicate. Prior to addition to the cells, the mixtures were pre-incubated for 2 h at 37° C. The level of LDLR at the cell surface was measured by FACS using anti human LDLR antibody and a suitable secondary antibody labeled with alexa 647. Cell surface LDLR is reported relative to Cnt(−). % inhibition of PCSK9 activity was calculated as [sdAb−Cnt(+)]/[Cnt(−)−Cnt(+)]×100. The gain-of-function PCSK9 protein was used as conditioned media from transiently transfected HEK293 cells and was quantified by ELISA.
Figure 11B:
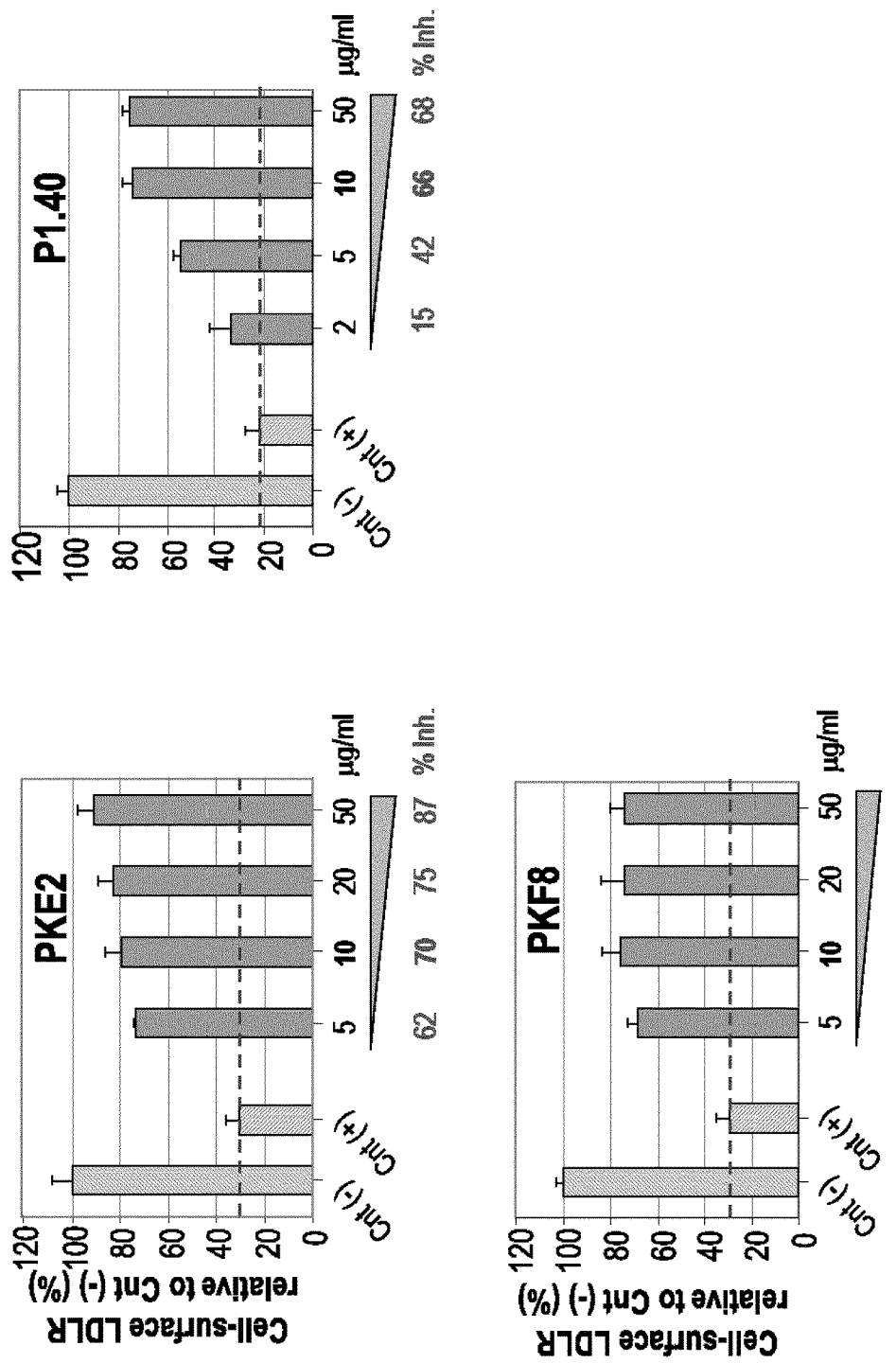

Naive HuH7 cells were also incubated for 18 h in the absence [Cnt(−)] or presence of 0.5 ug/ml (~6 nM) of PCSK9-D374Y (conditioned media from transfected HEK293 cells) alone [Cnt(+)] or mixed with 50 ug/ml (~3 uM) of various purified llama sdAb (FIG. 11A). In FIG. 11B, increasing concentrations of the PKE2, P1.40 or PKF8 sdAbs were used. These sdAbs inhibit the activity of the gain-of-function mutation (D374Y) of PCSK9 on LDLR degradation in a dose-dependent manner, reaching a maximum of 60-70% inhibition at 10 ug/ml.

Figure 12A:
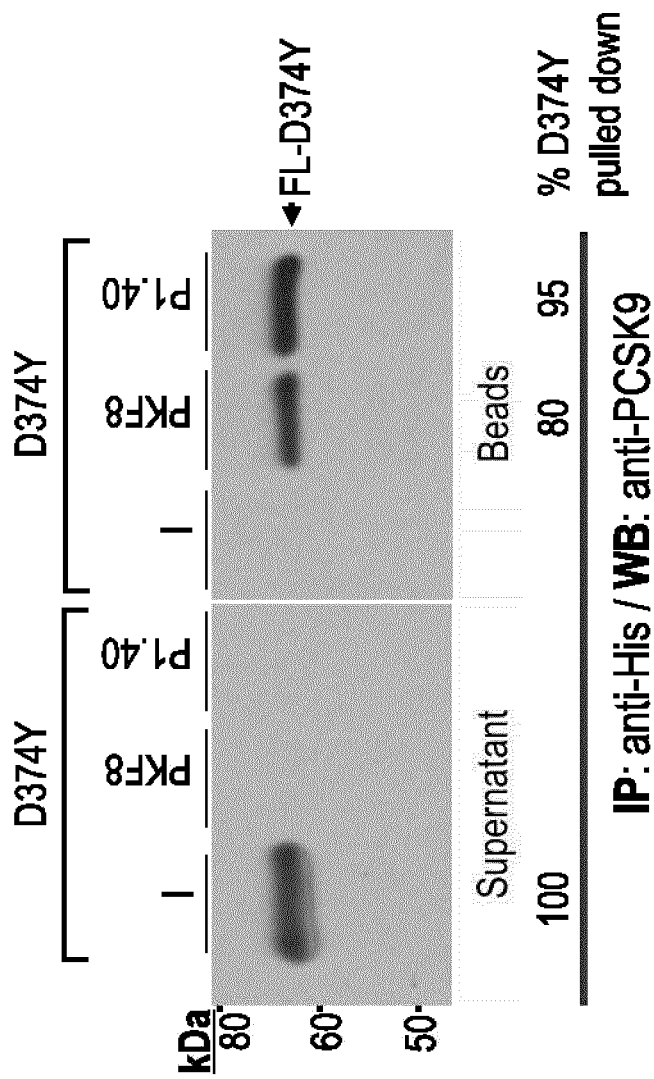
FIG. 12 shows [A] the gain-of-function PCSK9-D374Y protein pull-down experiment using PKF8 and P1.40 sdAbs. 60 ul of mixture containing 30 ng (0.5 ug/ml) of PCSK9-D374Y (as conditioned media from HEK293 cells), either alone or with 3.5 ug (50 ug/ml) purified sdAb (6His) was pre-incubated for 2 h at 37° C., followed by immunoprecipitation with 6.6 ug of anti-His Ab-agarose beads overnight, at 4° C. Supernatants and material eluted from the beads were subjected to PAGE-SDS (6%) and Western blot analysis with anti-hPCSK9 Ab. The percentage of PCSK9-D374Y pulled down was estimated by quantification of the detected bands using the ImageJ™ program; and [B] a schematical representation of the method used.
Figure 12B:
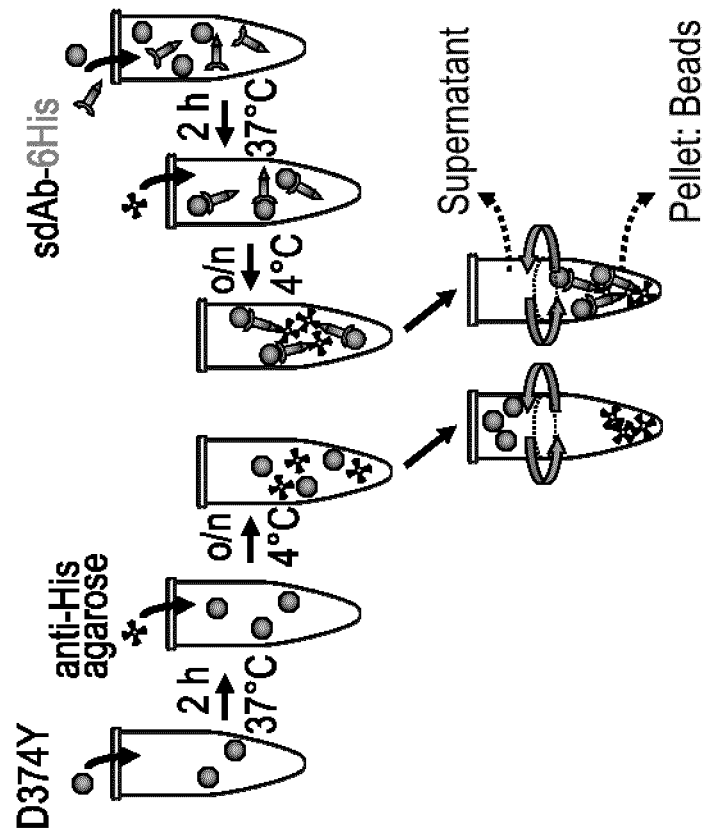

Conditioned media from HEK293 cells containing 30 ng (~6 nM) of PCSK9-D374Y, alone or mixed with 3.5 ug (~3 uM) of purified sdAbs(6His) was pre-incubated for 2 h at 37° C., followed by immunoprecipitation with 6.6 ug anti-His Ab-agarose beads overnight, at 4° C. Supernatants and material eluted from the beads were subjected to PAGE-SDS (6%) and Western blot analysis with anti-hPCSK9 Ab. Pull-down analyses show that an approximately 500 fold molar excess of PKF8 and P1.40 sdAbs over PCSK9-D374Y is able to bind approximately 90% of the PCSK9-D374Y protein (FIG. 12).

Figure 13:
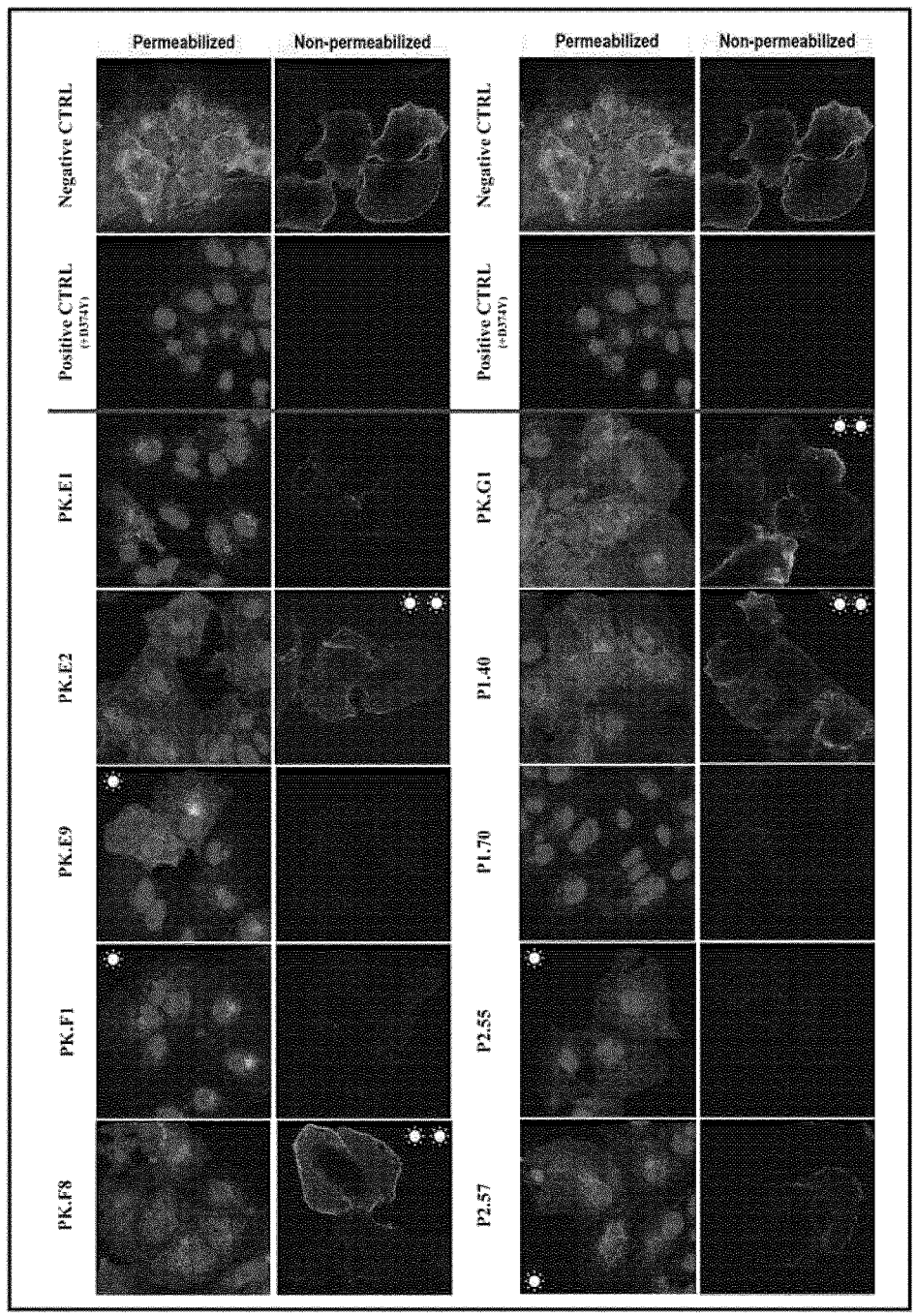
FIG. 13 shows the effect of sdAbs on LDLR at the surface of HuH7 cells. Cells were incubated 18 h in the absence (Negative CTRL) or presence of 0.5 ug/ml (~6 nM) PCSK9-D374Y protein alone (Positive CTRL) or mixed with 50 ug/ml (~3 uM) of various purified llama sdAbs, as indicated. The PCSK9-D374Y protein was used as conditioned media from transiently transfected HEK293 cells and was quantified by ELISA. Prior to addition to the cells, the mixtures were pre-incubated for 2 h at 37° C. Permeabilized or non-permeabilized HuH7 cells were analyzed by immunofluorescence. Cell nuclei were stained with DAPI (blue labeling), LDLR was stained with anti-LDLR Abs (green labeling)

Huh7 cells were incubated in the absence or presence of 0.5 ug/ml (~6 nM) of PCSK9-D374Y protein (conditioned media from transfected HEK293 cells), followed by the addition of 50 ug/ml (~3 uM) of various purified llama sdAbs. Prior to addition to the cells, the mixtures were pre-incubated for 2 h at 37° C. Permeabilized or non-permeabilized HuH7 cells were analyzed by immunofluorescence. Cell nuclei were stained with DAPI (blue labeling), LDLR was stained with anti-LDLR Abs (green labeling). As shown in FIG. 13, PKE2, PKF8, PKG1, and P1.40 increased the levels of LDLR at the cell surface of non-permeabilized HuH7 cells. LDLR immunofluorescence of permeabilized cells shows that certain sdAbs (e.g., P2.55 and P2.57) can also block LDLR intracellularly, with almost no increase in cell surface levels of LDLR.

The sdAbs internalisation analysis is also performed by immunofluorescence. Huh7 cells were incubated for 18 hours with conditioned media collected from HEK293 cells either transfected with i) a control V5-CTL+6His vector, ii) with PCSK9 (D374Y or WT) devoid of V5 tag, or iii) with V5-tagged sdAbs. Huh7 cells were also incubated for 18 hours with various 2 h-preincubated mixtures of ii) and iii). The internalization of the V5-tagged sdAbs is followed by immunofluorescence analysis of the V5 tag under non-permeabilized (cell-surface localization of the sdAb) or permeabilized (intra-cellular localization of the sdAb) conditions using a mAb-V5 (Invitrogen)

The sdAbs were also characterized using a Dil-LDL fluorescent uptake assay, as described in Poirier et al., *J. Biol. Chem.* 284: 28856-28864, 2009. The method consists of fluorescence measurement of the Dil-LDL cellular incorporation via LDLR internalization (a measurement of cell surface LDLR activity) into human hepatocyte derived HuH7 or HepG2 cell lines, in the presence or in the absence of PCSK9 purified proteins. The cells were incubated in a 96-well format with or without 10 µg/ml of sdAbs for 2 h, and then Dil-LDL was added for an additional 2 h. Cellular uptake of Dil-LDL is measured using a fluorescence plate reader. The inhibition of the PCSK9≡ LDLR functional interaction is detected by an increase in the Dil-LDL fluorescence.

Figure 14:
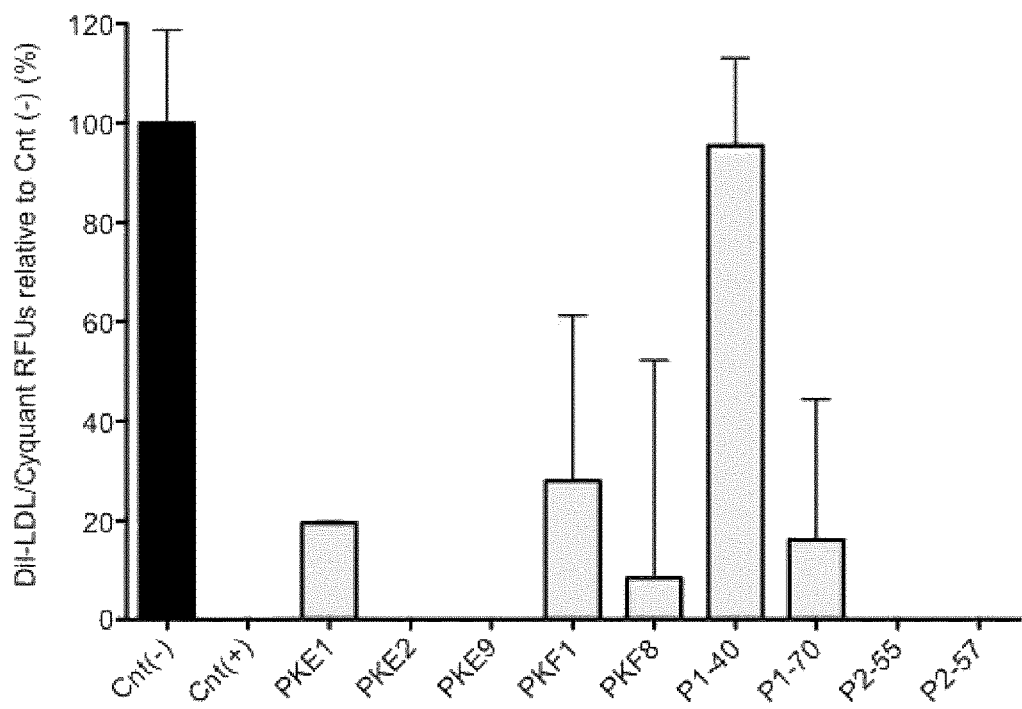
FIG. 14 shows the effect of sdAbs on PCSK9-D374Y gain-of-function mutation-induced LDLR degradation as measured with DiI-LDL uptake assay. Naive HepG2 cells were incubated for 4 h in the absence [Cnt(−)] or presence of 0.5 µg/mL purified PCSK9-mutant D374Y [Cnt(+)]. The addition of 50 µg/mL of various sdAbs is indicated below (PKE1 to P2-57)

In order to further test whether these sdAbs can also inhibit the function of a gain of function mutant D374Y of PCSK9, the cells were incubated with purified PCSK9-D374Y proteins and the antibodies activity was analyzed by using a Dil-LDL fluorescent uptake assay. The P1.40 sdAb was able to completely block the activity of PCSK9-D374Y on LDLR in HepG2 cells (FIG. 14).

Finally, the sdAbs are also tested on primary human hepatocytes in order to measure their effect on cell surface LDLR.

Figure 4:
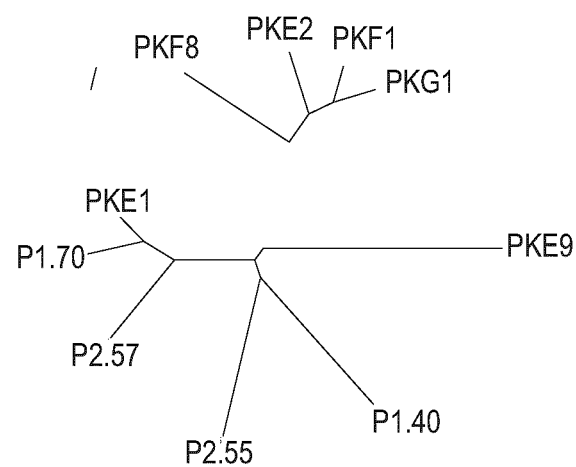
FIG. 4 shows a phylogenetic analysis deduced from the alignment of the protein sequences of the 10 sdAbs depicted in FIG. 3A.

The sdAb DNAs were sequenced. FIGS. 2 and 3 show the amino acid alignments of 17 sdAbs inhibiting the PCSK9-dependant LDLR degradation. In particular, alignments for subgroups of sdAbs are presented in FIGS. 3 D (subgroups of three to five) and E (pairs), many of which show a sequence identity of 80% or more (e.g., 80, 80.95%, 81, 83, 83.46%, 84, 85, 86, 87, 87.30%, 88, 90, 91, 93, 94, 96, 98%). FIG. 4 provides the phylogenetic tree of the sequences of the sdAbs depicted in FIGS. 2A and 3A.

Example 6: Characterisation of the sdAbs≡ PCSK9 Interaction and sdAb Properties

The PCSK9 domain which interacts with each sdAb, including P1.40, is determined by performing deletions and mutation analyses. This may be achieved, for example, by co-expressing 1) the cDNAs coding for each sdAb with 2) that of a construction allowing the expression of a specific PCSK9 domain (e.g., prosegment-V5, catalytic subunit-V5, CHRD-V5, etc.), sub fragment thereof, or PCSK9 mutant carrying a V5 tag sequence. The PCSK9≡ sdAb complex is pulled down with magnetic beads carrying a monoclonal antibody specific for the V5 sequence (mAb-V5). The sdAb is pulled down through its interaction with the PCSK9 domain, sub-fragment or mutant. The biochemical and biophysical properties of sdAbs selected are analyzed. Surface plasmon resonance (SPR) measures the affinities of the sdAbs to PCSK9. Different PCSK9 domains (e.g., prosegment, catalytic and CHRD domains) are used as antigens to assess domain specificity.

Biophysical properties are other important features of drug candidates. Properties of sdAbs are assessed for 1) formation of aggregation; and 2) resistance to proteolytic degradation. Formation of aggregation is assessed by performing size exclusion chromatography of the samples. The aggregation's molecular weight is estimated based on protein standard run under the same conditions. Comparison of such masses with their calculated molecular weight would indicate whether they exist as monomer, oligomers or mixtures of multiple formats. Monomeric sdAbs are preferentially chosen for further development.

The proteolytic stability of the isolated sdAbs may be assessed by treating the sdAbs with cathepsin B, thrombin or trypsin-like proteases, the three major proteases of human plasma.

Example 7: Possible Modifications of Selected PCSK9-Specific sdAbs

A new protein screening approach, FAst Screening of Expression, biological-properties and Affinities (FASEBA) has recently been established (U.S. Provisional Patent Application No. 61/272,119, the priority of which is claimed in WO/2011/020183). This method employs a protein anchor to attach the to-be-screened protein candidates to a carrier protein, allows estimation of multiple properties of the proteins without any protein purification and enables screening a very large number of protein candidates. This new approach may be employed to further improve the properties of sdAbs.

Affinity Maturation of sdAbs:

The solved structures of sdAb-antibody complexes revealed that the CDR3 is dominantly involved in antigen binding. Improvement of sdAb affinities is achieved by mutating both CDR3 and other CDRs (CDR1 and CDR2). For CDR3, mutations are introduced so that at each position ~50% of the residues are the original ones. For CDR1 and CDR2, this percentage is reduced to ~25%. Differential treatment of these regions is based on the importance of the CDRs in antigen binding. Whereas a large number of residues are preserved in CDR3 to generate a library with a high percentage of binders, more randomness is introduced in CDR1 and CDR2 to enhance the binding mainly mediated by CDR3. Given the huge theoretical library size when all CDRs are engineered simultaneously, a better strategy is to engineer CDR3 and CDR1/CDR2 in succession. Such mutation libraries are first screened using the FASEBA method to exclude a high percentage of sdAbs with unsatisfactory features. The remaining sdAbs are analyzed for their affinity directly by SPR without protein purification. Those with improved affinities are purified and assessed for their biophysical properties.

Humanization of sdAbs:

Humanization is performed similarly as in affinity maturation but with a different library construction strategy. Sequences of sdAbs with satisfactory affinities are compared with consensus sequences of human $V_H$, and key residues differing in camelid and human sdAbs are selected. A humanization library is constructed by replacing the camelid residues with human ones and screened using the FASEBA method to remove sdAbs with unsatisfactory properties. Affinity screening is not required as the CDRs remain the same.

Fusion of the Engineered sdAbs to IgG4-Fc and Production of Fusion Proteins:

The in vivo serum half lives of the sdAbs is extended by fusing them to human IgG4-Fc to generate IgG4 type. A large amount of such fusion protein (HCAbs-Fc) is produced in a transient mammalian expression system. The HCAbs-Fc is compared with its sdAb counterpart in functional affinities, biophysical features and ability/efficacy in inhibiting PCSK9 function.

Example 8: Characterisation of the Inhibition of PCSK9-Induced LDLR Degradation in Animal Models Drug candidates are then used in mice models expressing human PCSK9 to assess their ability in lowering plasma cholesterol levels in vivo.

Figure 15:
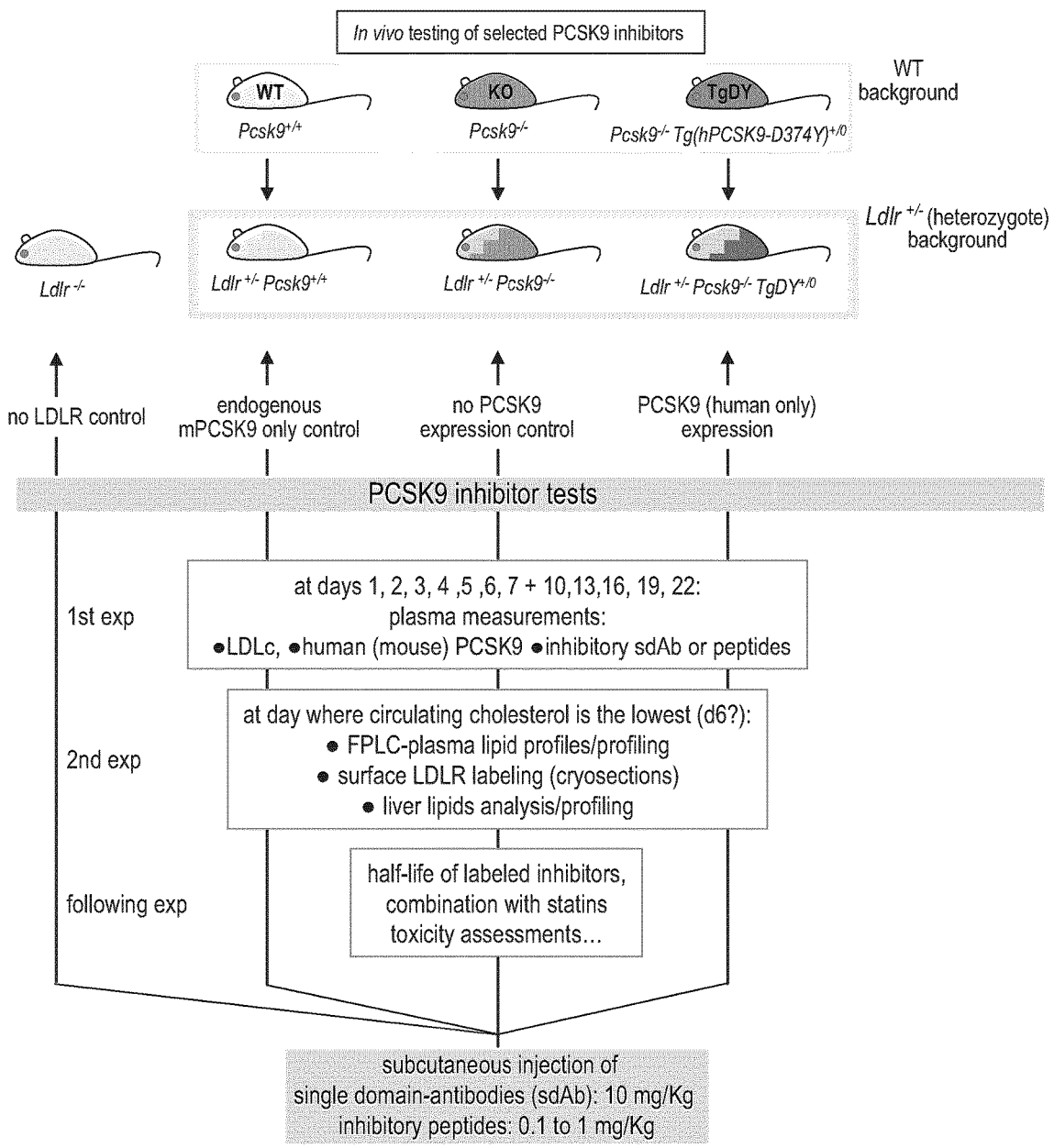
FIG. 15 shows the in vivo inhibition of PCSK9. Selected inhibitors are tested in heterozygote Ldlr$^{+/-}$ mice that exhibit "humanized" LDLc profiles (LDLc×2-3) and generated by intercrossing mice having WT and Ldlr$^{-/-}$ backgrounds. These mice express either normal levels of mouse PCSK9 (Pcsk$^{+/+}$), no PCSK9 (Pcsk9$^{-/-}$) and/or one or five copies of transgene encoding human PCSK9-D374Y from its own human promoter (TgDY). The human WT form of PCSK9 is also tested.

The PCSK9 sdAbs inhibitors are tested in mice overexpressing human PCSK9. Transgenic lines (Herbert, B., et al. (2010). *Arteriosclerosis, Thrombosis, and Vascular Biology*, 30 (7):1333-1339) that carry a ~190 kb of human genomic DNA expressing human PCSK9 (WT, D374Y low or D374Y high) from its own promoter are constructed. Further crosses generate a mouse strain expressing the human PCSK9 transgene in a $Pcsk9^{-/-}$ $Ldlr^{+/-}$ background (Ldlr heterozygote). This eliminates interference through the endogenous expression of the mouse PCSK9 genes and increases their LDLc levels (FIG. 15). By multiple backcrosses, these model mice are obtained in a pure C57BL/6 background for the homogeneity and reproducibility of the analyses. As control for specificity, the effect of the transgenes in an $Ldlr^{-/-}$ background is tested.

Mouse Injections:

The inhibitors (10 mg/Kg sdAb and 0.1-1 mg/Kg peptide) are injected intravenously to WT, $Pcsk9^{-/-}$, $Ldlr^{-/-}$ and Pcsk9-Tg mice, in 6 mice/genotype (FIG. 15). Total cholesterol (TC), LDLc and PCSK9 levels are measured every day during the first week and every third day for the next 2 weeks. The level of remaining uncomplexed PCSK9 in plasma is also measured by immunoprecipitation using a previously described antibody (Zaid, A., et al. (2008). *Hepatology*, 48(2): 646-65). In another set of experiments, 6 mice at the time point of lowest LDLc (4-7 days post-injection) are sacrificed and their FPLC plasma lipid profiles, as well as liver LDLR protein, are analyzed. If relevant, the half lives of $^{125}$I-labeled sdAb or peptide are assessed as a prelude to in vivo optimization. Any overt toxicity and/or morbidity effect is carefully monitored. The controls of $Pcsk9^{-/-}$, $Ldlr^{-/-}$ mice permit to verify that the effect observed is PCSK9-dependent.

Effect of Statin+sdAb:

The combination of atorvastatin and the best sdAb is evaluated, as statins increase PCSK9 expression while lowering that of the LDLR (Dubuc, G., et al. (2004). Arteriosclerosis, Thrombosis, and Vascular Biology, 24(8): 1454-1459; Lakoski, S. G., et al. (2009). *The Journal of Clinical Endocrinology and Metabolism*, 94(7): 2537-2543), and it was shown that statins decrease even further LDLc of $Pcsk9^{-/-}$ mice (Rashid, S., et al. (2005). *Proc Natl Acad Sci USA* 102(15):5374-5379).

Liver Steatosis:

$Pcsk9^{-/-}$ mice are protected against liver steatosis following a high cholesterol diet (Zaid, A., et al. (2008). *Hepatology*, 48(2): 646-65). Therefore mice fed for 2 weeks with a diet containing 0.2% cholesterol, are then injected with the sdAb or saline, and at the optimal post-injection time when LDLc is at its lowest, their livers are analyzed for the accumulation (or lack of) of neutral lipids using Oil-Red-0 (Zaid, A., et al. (2008). *Hepatology*, 48(2): 646-65).

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A single domain antibody specifically binding to human PCSK9, wherein the complementary determining region (CDR)1, CDR2 and CDR3 regions respectively comprise: (a) DYILG (SEQ ID NO: 4), AIRGSGAIRGREGSTFYVDSVKG (SEQ ID NO: 15) and DRFPTPEFSTQVGHYDY (SEQ ID NO: 29); (b) NYIVG (SEQ ID NO: 5), AIRGSGAIRGREGSTYYADSVKG (SEQ ID NO: 16) and DRFPTPEFTTQVGHYDV (SEQ ID NO: 30); (c) DYILG (SEQ ID NO: 4), AIRESGSSTYYADSVKG (SEQ ID NO: 17) and DQYPTPEFSTQVGHYDY (SEQ ID NO: 31); (d) HYILG (SEQ ID NO: 6), AIRESGSSTYYADSVKG (SEQ ID NO: 17) and DQYPTPEFSTQVGHYDY (SEQ ID NO: 31); (e) VYAMG (SEQ ID NO: 7), AITSPGDSIPYAHSVKG (SEQ ID NO: 18) and TKSGNYNYMGPDPKKYHY (SEQ ID NO: 32); (f) VYAMG (SEQ ID NO: 7), AITSSGDSIPYAHSVKG (SEQ ID NO: 19) and TTSGTYNYMGPDPKEYVY (SEQ ID NO: 33); (g) DYAMG (SEQ ID NO: 8), AAAQSGDSSAYARSVKG (SEQ ID NO: 20) and TTRGSYEYMGPDPKKYEY (SEQ ID NO: 34); (h) NYAMG (SEQ ID NO: 9), QISQVDGFTYYEDSVKG (SEQ ID NO: 21) and ALAFPTTSSNTYAY (SEQ ID NO: 35); (i) AYAMG (SEQ ID NO: 10), TIRDSDASIYYTDSVKG (SEQ ID NO: 22) and RQYYSGRVYSTFREEYDY (SEQ ID NO: 36); (j) IAYMA (SEQ ID NO: 11), SISSGGTTNYAVFAKG (SEQ ID NO: 23) and YAMSTETMVSQDY (SEQ ID NO: 37); (k) NYAMG (SEQ ID NO: 9), QISQVDGFTYYEDSVKG (SEQ ID NO: 21) and TYSGTYNYMGADPKEYVY (SEQ ID NO: 38); (l) SPTMA (SEQ ID NO: 12), AIRSRDDSTYYSNSVKG (SEQ ID NO: 24) and DPRTIDLSSRLLWGS (SEQ ID NO: 39); (m) HYILG (SEQ ID NO: 6), AIRESGSRTYYADSVRG (SEQ ID NO: 25) and DQYPTTEFSTQVGHYDY (SEQ ID NO: 40); (n) HYIVG (SEQ ID NO: 13), AVRESGSSTEYAENVKG (SEQ ID NO: 26) and DRFPTPEFSDRVGHYDL (SEQ ID NO: 41); (o) HYILG (SEQ ID NO: 6), AIRESGSRTYYADSVRG (SEQ ID NO: 25) and DQYPTPEFSTQVGHYDY (SEQ ID NO: 31); (p) HYILG (SEQ ID NO: 6), AVREPGSSTYYADSVKG (SEQ ID NO: 27) and DPYPTPEFTTHVGHYDY (SEQ ID NO: 42); or (q) HYVTS (SEQ ID NO: 14), GVTAHAGVTADVESTDYSDSVKG (SEQ ID NO: 28) and PSGFYRTIPHVHSNYDH (SEQ ID NO: 43).

2. The single domain antibody of claim 1, further comprising a framework region (FR) 1 comprising an amino acid sequence of formula IV:

(SEQ ID NO: 44)
Q-V-X6-L-X7-E-S-G-G-G-X8-V-Q-A-G-X9-S-X10-R-L-S-C-X11-X12-X13-X14-X15-X16-X17-X18 (IV)

wherein
X6 is K or Q;
X7 is E or V;
X8 is L or P;
X9 is G or D
X10 is L or M;
X11 is V, L, S, or A;
X12 is A or P;
X13 is S or P;
X14 is G, D or R;
X15 is R, L or S;
X16 is T, F, I or G;
X17 is I, V, P or F; and
X18 is N, R, S or V.

3. The single domain antibody of claim 2, wherein X6 is K; X7 is E; X8 is L; X9 is G; X10 is L; X11 is A; X12 is A; X13 is S; X14 is G; X15 is R; X16 is T; X17 is F; and/or X18 is N.

4. The antibody of claim 2, wherein the FR1 comprises one of the following amino acid sequences:

```
                                         (SEQ ID NO: 45)
QVKLEESGGGLVQAGGSLRLSCVASGRTIN, (SEQ ID NO: 46)
QVQLVESGGGLVQAGGSLRLSCLASDRTVN, (SEQ ID NO: 47)
QVQLVESGGGLVQAGGSLRLSCAASGRTPR, (SEQ ID NO: 48)
QVQLVESGGGLVQAGGSLRLSCAASGRTFS, (SEQ ID NO: 49)
QVKLEESGGGLVQAGGSLRLSCAASGRTFS, (SEQ ID NO: 50)
QVKLEESGGGLVQAGGSLRLSCAASGRTFN, (SEQ ID NO: 51)
QVKLEESGGGLVQAGGSLRLSCAASGLTFS, (SEQ ID NO: 52)
QVKLEESGGGLVQAGGSLRLSCSPSDRTFS, (SEQ ID NO: 53)
QVKLEESGGGLVQAGGSLRLSCAAPRSGVV, (SEQ ID NO: 54)
QVKLEESGGGPVQAGGSLRLSCLASGRFVN, (SEQ ID NO: 55)
QVQLVESGGGLVQAGGSMRLSCAASGRTPR, (SEQ ID NO: 56)
QVKLEESGGGLVQAGGSLRLSCAASGRTPR,
or
                                         (SEQ ID NO: 57)
QVKLEESGGGLVQAGDSLRLSCAASGRIFN.
```

5. The single domain antibody of claim 1, further comprising an FR2 comprising an amino acid sequence of formula V:

```
                                         (SEQ ID NO: 58)
X19-X20-R-Q-X21-P-X22-X23-X24-X25-X26-X27-V-X28

(V)
``` wherein
X19 is W or Y;
X20 is F or Y;
X21 is A or V;
X22 is G, D or E;
X23 is K, T, R, A, E or Q;
X24 is K, E, Q or L;
X25 is R or P;
X26 is E or K;
X27 is F or L; and
X28 is A, T or G.

6. The single domain antibody of claim 5, wherein X19 is W; X20 is F; X21 is A; X22 is G; X23 is K; X24 is E; X25 is R; X26 is E; X27 is F; and/or X28 is A.

7. The single domain antibody of claim 5, wherein the FR2 comprises one of the following amino acid sequences:

```
                                         (SEQ ID NO: 59)
            WFRQAPGKKREFVA, (SEQ ID NO: 60)
            YFRQAPGKEREFVA, (SEQ ID NO: 61)
            WFRQAPGKQREFVA, (SEQ ID NO: 62)
            WFRQAPGKEREFVA, (SEQ ID NO: 63)
            WFRQAPGKEREFVT, (SEQ ID NO: 64)
            WFRQAPGTEREFVG, (SEQ ID NO: 65)
            WFRQVPGREREFVA, (SEQ ID NO: 66)
            WYRQAPEKQRELVA, (SEQ ID NO: 67)
            WFRQAPGAEREFVG, (SEQ ID NO: 68)
            WFRQAPGEERKFVA, (SEQ ID NO: 69)
            WFRQAPGKLPEFVA,
or
                                         (SEQ ID NO: 70)
            WFRQAPDQEREFVA.
```

8. The single domain antibody of claim 1, further comprising an FR3 comprising an amino acid sequence of formula VI:

```
                                         (SEQ ID NO: 71)
R-X29-X30-X31-S-X32-X33-X34-X35-K-X36-X37-X38-X39-

L-X40-M-X41-S-L-X42-P-X43-D-X44-A-X45-Y-X46-C-X47-

X48 (VI)
``` wherein
X29 is Y, F or D;
X30 is T, S or V;
X31 is I or V;
X32 is K, R, A or L;
X33 is D or N;
X34 is N, G, H or Y;
X35 is A, T, V or S;
X36 is N or S;
X37 is T or A;
X38 is V, I, L, A or G;
X39 is Y, D or F;
X40 is Q or R;
X41 is N, D or S;
X42 is K, I or Q;
X43 is E or D;
X44 is S or T;
X45 is T, V or A;
X46 is Y or I;
X47 is A or N; and
X48 is A, V, L or G.

9. The single domain antibody of claim 8, wherein X29 is F; X30 is T; X31 is I; X32 is R; X33 is D; X34 is N; X35 is A; X36 is N; X37 is T; X38 is V; X39 is Y; X40 is Q; X41 is N; X42 is K; X43 is E; X44 is T; X45 is V; X46 is Y; X47 is A; and/or X48 is A.

10. The single domain antibody of claim 8, wherein the FR3 comprises one of the following amino acid sequences:

```
                                      (SEQ ID NO: 72)
RYTISKDNAKNTVDLQMNSLKPEDSATYYCAV, (SEQ ID NO: 73)
RFSISKDNAKNTIYLQMNSLKPEDSAVYYCAL, (SEQ ID NO: 74)
RYTISRNNTKNAVDLQMNSLKPEDSATYYCAV, (SEQ ID NO: 75)
RYTISRDNTKNAVDLQMNSLKPEDSATYYCAV, (SEQ ID NO: 76)
RFTISRDNAKNTLYLQMNSLKPEDTAAYYCAA, (SEQ ID NO: 77)
RFTISRDNAKNTVYLQMNSLKPEDTAAYYCAA, (SEQ ID NO: 78)
RFTISRDGAKNTAYLQMDSLKPEDTAAYYCAA, (SEQ ID NO: 79)
RFTISRDNAKNTVYLQMNSLKPDDTAVYYCAA, (SEQ ID NO: 80)
RFTISRDNAKNTVYLQMNSLIPDDTAVYYCAA, (SEQ ID NO: 81)
RFTISADNAKNTVYLQMNSLKPEDTAVYICNA, (SEQ ID NO: 82)
RFTISRDNAKNTVYLQMSSLKPDDTAVYYCAA, (SEQ ID NO: 83)
RFTISLDNAKNTAYLRMDSLQPEDTAVYYCAG, (SEQ ID NO: 84)
RDTISRDNTKNAGDLQMNSLKPEDSATYYCAV, (SEQ ID NO: 85)
RFVISKDNVKSTVFLQMNSLKPEDSAVYYCAL, (SEQ ID NO: 86)
RDTISKDHTKNAVDLQMNSLKPEDSATYYCAV,
or (SEQ ID NO: 87)
RFTVSRDYSKNTVYLQMNSLKPEDTAVYYCAA.
```

11. The single domain antibody of claim 1, further comprising an FR4 comprising an amino acid sequence of formula VII:

```
                                      (SEQ ID NO: 88)
X49-G-X50-G-T-X51-V-T-X52-S-S (VII)
``` wherein
X49 is W or S;
X50 is R or Q;
X51 is Q or E; and
X52 is V or I.

12. The single domain antibody of claim 11, wherein X49 is W; X50 is Q; X51 is Q; and/or X52 is V.

13. The single domain antibody of claim 11, wherein the FR4 comprises one of the following amino acid sequences:

```
                                      (SEQ ID NO: 89)
WGQGTQVTVSS, (SEQ ID NO: 90)
WGRGTQVTVSS, (SEQ ID NO: 91)
SGQGTQVTVSS,
or (SEQ ID NO: 92)
WGQGTEVTISS.
```

14. The single domain antibody of claim 1, comprising one of the following amino acid sequences:

```
                                                    (SEQ ID NO: 93)
QVKLEESGGGLVQAGGSLRLSCVASGRTINDYILGWFRQAPGKKREFVAA

IRGSGAIRGREGSTFYVDSVKGRYTISKDNAKNTVDLQMNSLKPEDSATY

YCAVDRFPTPEFSTQVGHYDYWGQGTQVTVSS;

(SEQ ID NO: 94)
QVQLVESGGGLVQAGGSLRLSCLASDRTVNNYIVGYFRQAPGKEREFVAA

IRGSGAIRGREGSTYYADSVKGRFSISKDNAKNTIYLQMNSLKPEDSAVY

YCALDRFPTPEFTTQVGHYDVWGRGTQVTVSS;

(SEQ ID NO: 95)
QVKLEESGGGLVQAGGSLRLSCVASGRTINDYILGWFRQAPGKKREFVAA

IRESGSSTYYADSVKGRYTISRNNTKNAVDLQMNSLKPEDSATYYCAVDQ

YPTPEFSTQVGHYDYWGQGTQVTVSS;

(SEQ ID NO: 96)
QVQLVESGGGLVQAGGSLRLSCAASGRTPRHYILGWFRQAPGKQREFVAA

IRESGSSTYYADSVKGRYTISRDNTKNAVDLQMNSLKPEDSATYYCAVDQ

YPTPEFSTQVGHYDYWGQGTQVTVSS;

(SEQ ID NO: 97)
QVQLVESGGGLVQAGGSLRLSCAASGRTFSVYAMGWFRQAPGKEREFVAA

ITSPGDSIPYAHSVKGRFTISRDNAKNTLYLQMNSLKPEDTAAYYCAATK

SGNYNYMGPDPKKYHYWGQGTQVTVSS;

(SEQ ID NO: 98)
QVKLEESGGGLVQAGGSLRLSCAASGRTFSVYAMGWFRQAPGKEREFVTA

ITSSGDSIPYAHSVKGRFTISRDNAKNTVYLQMNSLKPEDTAAYYCAATT

SGTYNYMGPDPKEYVYWGQGTQVTVSS;

(SEQ ID NO: 99)
QVKLEESGGGLVQAGGSLRLSCAASGRTFNDYAMGWFRQAPGKEREFVAA

AAQSGDSSAYARSVKGRFTISRDGAKNTAYLQMDSLKPEDTAAYYCAATT

RGSYEYMGPDPKKYEYWGQGTQVTVSS;

(SEQ ID NO: 100)
QVKLEESGGGLVQAGGSLRLSCAASGLTFSNYAMGWFRQAPGTEREFVGQ

ISQVDGFTYYEDSVKGRFTISRDNAKNTVYLQMNSLKPDDTAVYYCAAAL

AFPTTSSNTYAYSGQGTQVTVSS;

(SEQ ID NO: 101)
QVKLEESGGGLVQAGGSLRLSCSPSDRTFSAYAMGWFRQVPGREREFVAT

IRDSDASIYYTDSVKGRFTISRDNAKNTVYLQMNSLIPDDTAVYYCAARQ

YYSGRVYSTFREEYDYWGQGTQVTVSS;

(SEQ ID NO: 102)
QVKLEESGGGLVQAGGSLRLSCAAPRSGVVIAYMAWYRQAPEKQRELVAS

ISSGGTTNYAVFAKGRFTISADNAKNTVYLQMNSLKPEDTAVYICNAYAM

STETMVSQDYWGQGTQVTVSS;
```

-continued (SEQ ID NO: 103)
QVKLEESGGGLVQAGGSLRLSCAASGLTFSNYAMGWFRQAPGAEREFVGQ

ISQVDGFTYYEDSVKGRFTISRDNAKNTVYLQMSSLKPDDTAVYYCAATY

SGTYNYMGADPKEYVYWGQGTQVTVSS;

(SEQ ID NO: 104)
QVKLEESGGGPVQAGGSLRLSCLASGRFVNSPTMAWFRQAPGEERKFVAA

IRSRDDSTYYSNSVKGRFTISLDNAKNTAYLRMDSLQPEDTAVYYCAGDP

RTIDLSSRLLWGSWGQGTQVTVSS;

(SEQ ID NO: 105)
QVQLVESGGGLVQAGGSMRLSCAASGRTPRHYILGWFRQAPGKQREFVAA

IRESGSRTYYADSVRGRDTISRDNTKNAGDLQMNSLKPEDSATYYCAVDQ

YPTTEFSTQVGHYDYWGQGTEVTISS;

(SEQ ID NO: 106)
QVKLEESGGGLVQAGGSLRLSCAASGRTPRHYIVGWFRQAPGKEREFVAA

VRESGSSTEYAENVKGRFVISKDNVKSTVFLQMNSLKPEDSAVYYCALDR

FPTPEFSDRVGHYDLWGQGTQVTVSS;

(SEQ ID NO: 107)
QVQLVESGGGLVQAGGSMRLSCAASGRTPRHYILGWFRQAPGKQREFVAA

IRESGSRTYYADSVRGRYTISRDNTKNAVDLQMNSLKPEDSATYYCAVDQ

YPTPEFSTQVGHYDYWGQGTQVTVSS;

(SEQ ID NO: 108)
QVKLEESGGGLVQAGGSLRLSCAASGRTPRHYILGWFRQAPGKLPEFVAA

VREPGSSTYYADSVKGRDTISKDHTKNAVDLQMNSLKPEDSATYYCAVDP

YPTPEFTTHVGHYDYWGQGTQVTVSS; or (SEQ ID NO: 109)
QVKLEESGGGLVQAGDSLRLSCAASGRIFNHYVTSWFRQAPDQEREFVAG

VTAHAGVTADVESTDYSDSVKGRFTVSRDYSKNTVYLQMNSLKPEDTAVY

YCAAPSGFYRTIPHVHSNYDHWGQGTQVTVSS.

15. A pharmaceutical composition comprising at least one of the single domain antibodies as defined in claim 1.

16. The pharmaceutical composition of claim 15, further comprising at least one other single domain antibody as defined in claim 1.

17. The pharmaceutical composition of claim 15, further comprising a pharmaceutical carrier or excipient.

18. A method for treating a low-density lipid-cholesterol-related disease comprising administering to a subject in need thereof an effective amount of the single domain antibody as defined in claim 1 or a composition comprising at least the single domain antibody.

19. The method of claim 18, wherein the low-density lipid-cholesterol-related disease is hypercholesterolemia.

20. A nucleic acid molecule comprising a nucleotide sequence encoding the single domain antibody as defined in claim 1 or a vector comprising the nucleic acid molecule or a cell comprising the nucleic acid molecule or the vector.

21. A kit for (i) treating a low-density lipid-cholesterol-related disease in a subject; or (ii) detecting PCSK9 in a biological sample, comprising at least two of the single domain antibodies as defined in claim 1.

22. The kit of claim 21, wherein the low-density lipid-cholesterol-related disease is hypercholesterolemia.

\* \* \* \* \*

SEQUENCE LISTING

```
<160> NUMBER OF SEQ ID NOS: 150

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: Xaa can be any naturally occurring amino acid

<400> SEQUENCE: 1

Xaa Xaa Xaa Xaa Xaa
1               5

<210> SEQ ID NO 2
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(16)
<223> OTHER INFORMATION: Xaa can be any naturally occurring amino acid
```

```
<220> FEATURE:
<221> NAME/KEY: misc_feature
<222> LOCATION: (18)..(22)
<223> OTHER INFORMATION: Xaa can be any naturally occurring amino acid

<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Tyr Xaa Xaa Xaa Xaa Xaa Gly
            20

<210> SEQ ID NO 3
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: Xaa can be any naturally occurring amino acid

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Asp Tyr Ile Leu Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Asn Tyr Ile Val Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

His Tyr Ile Leu Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct
```

<400> SEQUENCE: 7

Val Tyr Ala Met Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asp Tyr Ala Met Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Asn Tyr Ala Met Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Ala Tyr Ala Met Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Ile Ala Tyr Met Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Ser Pro Thr Met Ala
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

```
<400> SEQUENCE: 13

His Tyr Ile Val Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

His Tyr Val Thr Ser
1               5

<210> SEQ ID NO 15
<211> LENGTH: 23
<212> TYPE: PRT
<213> ORGANISM: Artificial Sequence
<220> FEATURE:
<223> OTHER INFORMATION: Synthetic Construct

<400> SEQUENCE: 15

Ala Ile Arg Gly Ser Gly Ala Ile Arg Gly Arg Glu Gly Ser Thr Phe
1               5                   10                  15

Tyr Val Asp Ser Val Lys Gly
            20

<210> SEQ ID NO 16
<211> LENGTH: 23
<212> TYPE: PRT
<213> ORGANISM: Artificial Sequence
<220> FEATURE:
<223> OTHER INFORMATION: Synthetic Construct

<400> SEQUENCE: 16

Ala Ile Arg Gly Ser Gly Ala Ile Arg Gly Arg Glu Gly Ser Thr Tyr
1               5                   10                  15

Tyr Ala Asp Ser Val Lys Gly
            20

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Ala Ile Arg Glu Ser Gly Ser Ser Thr Tyr Tyr Ala Asp Ser Val Lys
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: Synthetic Construct

<400> SEQUENCE: 18

Ala Ile Thr Ser Pro Gly Asp Ser Ile Pro Tyr Ala His Ser Val Lys
1               5                   10                  15

Gly
```

<210> SEQ ID NO 19
<211> LENGTH: 17
<212> TYPE: PRT
<213> ORGANISM: Artificial Sequence
<220> FEATURE:
<223> OTHER INFORMATION: Synthetic Construct

<400> SEQUENCE: 19

Ala Ile Thr Ser Ser Gly Asp Ser Ile Pro Tyr Ala His Ser Val Lys
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Ala Ala Ala Gln Ser Gly Asp Ser Ser Ala Tyr Ala Arg Ser Val Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Gln Ile Ser Gln Val Asp Gly Phe Thr Tyr Tyr Glu Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

Thr Ile Arg Asp Ser Asp Ala Ser Ile Tyr Tyr Thr Asp Ser Val Lys
1               5                   10                  15

Gly

<210> SEQ ID NO 23
<211> LENGTH: 16
<212> TYPE: PRT
<213> ORGANISM: Artificial Sequence
<220> FEATURE:
<223> OTHER INFORMATION: Synthetic Construct

<400> SEQUENCE: 23

Ser Ile Ser Ser Gly Gly Thr Thr Asn Tyr Ala Val Phe Ala Lys Gly
1               5                   10                  15

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct -continued

```
<400> SEQUENCE: 24

Ala Ile Arg Ser Arg Asp Asp Ser Thr Tyr Tyr Ser Asn Ser Val Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Ala Ile Arg Glu Ser Gly Ser Arg Thr Tyr Tyr Ala Asp Ser Val Arg
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Ala Val Arg Glu Ser Gly Ser Ser Thr Glu Tyr Ala Glu Asn Val Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Ala Val Arg Glu Pro Gly Ser Ser Thr Tyr Tyr Ala Asp Ser Val Lys
1               5                   10                  15

Gly

<210> SEQ ID NO 28
<211> LENGTH: 23
<212> TYPE: PRT
<213> ORGANISM: Artificial Sequence
<220> FEATURE:
<223> OTHER INFORMATION: Synthetic Construct

<400> SEQUENCE: 28

Gly Val Thr Ala His Ala Gly Val Thr Ala Asp Val Glu Ser Thr Asp
1               5                   10                  15

Tyr Ser Asp Ser Val Lys Gly
            20

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 29

Asp Arg Phe Pro Thr Pro Glu Phe Ser Thr Gln Val Gly His Tyr Asp
1               5                   10                  15

Tyr

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Asp Arg Phe Pro Thr Pro Glu Phe Thr Thr Gln Val Gly His Tyr Asp
1               5                   10                  15

Val

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Asp Gln Tyr Pro Thr Pro Glu Phe Ser Thr Gln Val Gly His Tyr Asp
1               5                   10                  15

Tyr

<210> SEQ ID NO 32
<211> LENGTH: 18
<212> TYPE: PRT
<213> ORGANISM: Artificial Sequence
<220> FEATURE:
<223> OTHER INFORMATION: Synthetic Construct

<400> SEQUENCE: 32

Thr Lys Ser Gly Asn Tyr Asn Tyr Met Gly Pro Asp Pro Lys Lys Tyr
1               5                   10                  15

His Tyr

<210> SEQ ID NO 33
<211> LENGTH: 18
<212> TYPE: PRT
<213> ORGANISM: Artificial Sequence
<220> FEATURE:
<223> OTHER INFORMATION: Synthetic Construct

<400> SEQUENCE: 33

Thr Thr Ser Gly Thr Tyr Asn Tyr Met Gly Pro Asp Pro Lys Glu Tyr
1               5                   10                  15

Val Tyr

<210> SEQ ID NO 34
<211> LENGTH: 18
<212> TYPE: PRT
<213> ORGANISM: Artificial Sequence
<220> FEATURE:
<223> OTHER INFORMATION: Synthetic Construct
```

```
<400> SEQUENCE: 34

Thr Thr Arg Gly Ser Tyr Glu Tyr Met Gly Pro Asp Pro Lys Lys Tyr
1               5                   10                  15

Glu Tyr

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Ala Leu Ala Phe Pro Thr Thr Ser Ser Asn Thr Tyr Ala Tyr
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Synthetic Construct

<400> SEQUENCE: 36

Arg Gln Tyr Tyr Ser Gly Arg Val Tyr Ser Thr Phe Arg Glu Glu Tyr
1               5                   10                  15

Asp Tyr

<210> SEQ ID NO 37
<211> LENGTH: 13
<212> TYPE: PRT
<213> ORGANISM: Artificial Sequence
<220> FEATURE:
<223> OTHER INFORMATION: Synthetic Construct

<400> SEQUENCE: 37

Tyr Ala Met Ser Thr Glu Thr Met Val Ser Gln Asp Tyr
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Synthetic Construct

<400> SEQUENCE: 38

Thr Tyr Ser Gly Thr Tyr Asn Tyr Met Gly Ala Asp Pro Lys Glu Tyr
1               5                   10                  15

Val Tyr

<210> SEQ ID NO 39
<211> LENGTH: 15
<212> TYPE: PRT
<213> ORGANISM: Artificial Sequence
<220> FEATURE:
<223> OTHER INFORMATION: Synthetic Constructt

<400> SEQUENCE: 39

Asp Pro Arg Thr Ile Asp Leu Ser Ser Arg Leu Leu Trp Gly Ser
1               5                   10                  15
```

```
<210> SEQ ID NO 40
<211> LENGTH: 17
<212> TYPE: PRT
<213> ORGANISM: Artificial Sequence
<220> FEATURE:
<223> OTHER INFORMATION: Synthetic Construct

<400> SEQUENCE: 40

Asp Gln Tyr Pro Thr Thr Glu Phe Ser Thr Gln Val Gly His Tyr Asp
1               5                   10                  15

Tyr

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Asp Arg Phe Pro Thr Pro Glu Phe Ser Asp Arg Val Gly His Tyr Asp
1               5                   10                  15

Leu

<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Asp Pro Tyr Pro Thr Pro Glu Phe Thr Thr His Val Gly His Tyr Asp
1               5                   10                  15

Tyr

<210> SEQ ID NO 43
<211> LENGTH: 17
<212> TYPE: PRT
<213> ORGANISM: Artificial Sequence
<220> FEATURE:
<223> OTHER INFORMATION: Synthetic Construct

<400> SEQUENCE: 43

Pro Ser Gly Phe Tyr Arg Thr Ile Pro His Val His Ser Asn Tyr Asp
1               5                   10                  15

His

<210> SEQ ID NO 44
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
```

```
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (23)..(30)
<223> OTHER INFORMATION: Xaa can be any naturally occurring amino acid

<400> SEQUENCE: 44

Gln Val Xaa Leu Xaa Glu Ser Gly Gly Gly Xaa Val Gln Ala Gly Xaa
1               5                   10                  15

Ser Xaa Arg Leu Ser Cys Xaa Xaa Xaa Xaa Xaa Xaa Xaa Xaa
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Synthetic Construct

<400> SEQUENCE: 45

Gln Val Lys Leu Glu Glu Ser Gly Gly Gly Leu Val Gln Ala Gly Gly
1               5                   10                  15

Ser Leu Arg Leu Ser Cys Val Ala Ser Gly Arg Thr Ile Asn
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Glu Ser Gly Gly Gly Leu Val Gln Ala Gly Gly
1               5                   10                  15

Ser Leu Arg Leu Ser Cys Leu Ala Ser Asp Arg Thr Val Asn
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Pro Arg
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Synthetic Construct
```

```
<400> SEQUENCE: 48

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Synthetic Construct

<400> SEQUENCE: 49

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Synthetic Construct

<400> SEQUENCE: 50

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic Construct

<400> SEQUENCE: 51

Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Phe Ser
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic Construct

<400> SEQUENCE: 52

Gln Val Lys Leu Glu Glu Ser Gly Gly Gly Leu Val Gln Ala Gly Gly
1               5                   10                  15

Ser Leu Arg Leu Ser Cys Ser Pro Ser Asp Arg Thr Phe Ser
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Synthetic Construct
```

```
<400> SEQUENCE: 53

Gln Val Lys Leu Glu Glu Ser Gly Gly Gly Leu Val Gln Ala Gly Gly
1               5                   10                  15

Ser Leu Arg Leu Ser Cys Ala Ala Pro Arg Ser Gly Val Val
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Synthetic Construct

<400> SEQUENCE: 54

Gln Val Lys Leu Glu Glu Ser Gly Gly Gly Pro Val Gln Ala Gly Gly
1               5                   10                  15

Ser Leu Arg Leu Ser Cys Leu Ala Ser Gly Arg Phe Val Asn
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Synthetic Construct

<400> SEQUENCE: 55

Gln Val Gln Leu Val Glu Ser Gly Gly Gly Leu Val Gln Ala Gly Gly
1               5                   10                  15

Ser Met Arg Leu Ser Cys Ala Ala Ser Gly Arg Thr Pro Arg
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Synthetic Construct

<400> SEQUENCE: 56

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Pro Arg
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Synthetic Construct

<400> SEQUENCE: 57

Gln Val Lys Leu Glu Glu Ser Gly Gly Gly Leu Val Gln Ala Gly Asp
1               5                   10                  15

Ser Leu Arg Leu Ser Cys Ala Ala Ser Gly Arg Ile Phe Asn
            20                  25                  30

<210> SEQ ID NO 58
<211> LENGTH: 14
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 58

Xaa Xaa Arg Gln Xaa Pro Xaa Xaa Xaa Xaa Xaa Xaa Val Xaa
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Synthetic Construct

<400> SEQUENCE: 59

Trp Phe Arg Gln Ala Pro Gly Lys Lys Arg Glu Phe Val Ala
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Synthetic Construct

<400> SEQUENCE: 60

Tyr Phe Arg Gln Ala Pro Gly Lys Glu Arg Glu Phe Val Ala
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic Construct

<400> SEQUENCE: 61

Trp Phe Arg Gln Ala Pro Gly Lys Gln Arg Glu Phe Val Ala
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetic Construct

<400> SEQUENCE: 62

Trp Phe Arg Gln Ala Pro Gly Lys Glu Arg Glu Phe Val Ala
1               5                   10

<210> SEQ ID NO 63
<211> LENGTH: 14
<212> TYPE: PRT
<213> ORGANISM: Artificial Sequence
```

```
<220> FEATURE:
<223> OTHER INFORMATION: Synthetic Construct

<400> SEQUENCE: 63

Trp Phe Arg Gln Ala Pro Gly Lys Glu Arg Glu Phe Val Thr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

Trp Phe Arg Gln Ala Pro Gly Thr Glu Arg Glu Phe Val Gly
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic Construct

<400> SEQUENCE: 65

Trp Phe Arg Gln Val Pro Gly Arg Glu Arg Glu Phe Val Ala
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic Construct

<400> SEQUENCE: 66

Trp Tyr Arg Gln Ala Pro Glu Lys Gln Arg Glu Leu Val Ala
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetic Construct

<400> SEQUENCE: 67

Trp Phe Arg Gln Ala Pro Gly Ala Glu Arg Glu Phe Val Gly
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic Construct

<400> SEQUENCE: 68

Trp Phe Arg Gln Ala Pro Gly Glu Glu Arg Lys Phe Val Ala
1               5                   10

<210> SEQ ID NO 69
<211> LENGTH: 14
<212> TYPE: PRT
<213> ORGANISM: Artificial Sequence
```

<220> FEATURE:
<223> OTHER INFORMATION: Synthetic Construct

<400> SEQUENCE: 69

Trp Phe Arg Gln Ala Pro Gly Lys Leu Pro Glu Phe Val Ala
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic Construct

<400> SEQUENCE: 70

Trp Phe Arg Gln Ala Pro Asp Gln Glu Arg Glu Phe Val Ala
1               5                   10

<210> SEQ ID NO 71
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid

<400> SEQUENCE: 71

Arg Xaa Xaa Xaa Ser Xaa Xaa Xaa Lys Xaa Xaa Xaa Xaa Leu Xaa
1               5                   10                  15

Met Xaa Ser Leu Xaa Pro Xaa Asp Xaa Ala Xaa Tyr Xaa Cys Xaa Xaa
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Synthetic Construct

<400> SEQUENCE: 72

Arg Tyr Thr Ile Ser Lys Asp Asn Ala Lys Asn Thr Val Asp Leu Gln
1               5                   10                  15

Met Asn Ser Leu Lys Pro Glu Asp Ser Ala Thr Tyr Tyr Cys Ala Val
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Synthetic Construct

<400> SEQUENCE: 73

Arg Phe Ser Ile Ser Lys Asp Asn Ala Lys Asn Thr Ile Tyr Leu Gln
1               5                   10                  15

Met Asn Ser Leu Lys Pro Glu Asp Ser Ala Val Tyr Tyr Cys Ala Leu
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Synthetic Construct

<400> SEQUENCE: 74

Arg Tyr Thr Ile Ser Arg Asn Asn Thr Lys Asn Ala Val Asp Leu Gln
1               5                   10                  15

Met Asn Ser Leu Lys Pro Glu Asp Ser Ala Thr Tyr Tyr Cys Ala Val
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Synthetic Construct

<400> SEQUENCE: 75

Arg Tyr Thr Ile Ser Arg Asp Asn Thr Lys Asn Ala Val Asp Leu Gln
1               5                   10                  15

Met Asn Ser Leu Lys Pro Glu Asp Ser Ala Thr Tyr Tyr Cys Ala Val
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Synthetic Construct

```
<400> SEQUENCE: 76

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Ala Tyr Tyr Cys Ala Ala
                20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Synthetic Construct

<400> SEQUENCE: 77

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Ala Tyr Tyr Cys Ala Ala
                20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Synthetic Construct

<400> SEQUENCE: 78

Arg Phe Thr Ile Ser Arg Asp Gly Ala Lys Asn Thr Ala Tyr Leu Gln
1               5                   10                  15

Met Asp Ser Leu Lys Pro Glu Asp Thr Ala Ala Tyr Tyr Cys Ala Ala
                20                  25                  30

<210> SEQ ID NO 79
<211> LENGTH: 32
<212> TYPE: PRT
<213> ORGANISM: Artificial Sequence
<220> FEATURE:
<223> OTHER INFORMATION: Synthetic Construct

<400> SEQUENCE: 79

Arg Phe Thr Ile Ser Arg Asp Asn Ala Lys Asn Thr Val Tyr Leu Gln
1               5                   10                  15

Met Asn Ser Leu Lys Pro Asp Asp Thr Ala Val Tyr Tyr Cys Ala Ala
                20                  25                  30

<210> SEQ ID NO 80
<211> LENGTH: 32
<212> TYPE: PRT
<213> ORGANISM: Artificial Sequence
<220> FEATURE:
<223> OTHER INFORMATION: Synthetic Construct

<400> SEQUENCE: 80

Arg Phe Thr Ile Ser Arg Asp Asn Ala Lys Asn Thr Val Tyr Leu Gln
1               5                   10                  15

Met Asn Ser Leu Ile Pro Asp Asp Thr Ala Val Tyr Tyr Cys Ala Ala
                20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Synthetic Construct
```

```
<400> SEQUENCE: 81

Arg Phe Thr Ile Ser Ala Asp Asn Ala Lys Asn Thr Val Tyr Leu Gln
1               5                   10                  15

Met Asn Ser Leu Lys Pro Glu Asp Thr Ala Val Tyr Ile Cys Asn Ala
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Synthetic Construct

<400> SEQUENCE: 82

Arg Phe Thr Ile Ser Arg Asp Asn Ala Lys Asn Thr Val Tyr Leu Gln
1               5                   10                  15

Met Ser Ser Leu Lys Pro Asp Asp Thr Ala Val Tyr Tyr Cys Ala Ala
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Synthetic Construct

<400> SEQUENCE: 83

Arg Phe Thr Ile Ser Leu Asp Asn Ala Lys Asn Thr Ala Tyr Leu Arg
1               5                   10                  15

Met Asp Ser Leu Gln Pro Glu Asp Thr Ala Val Tyr Tyr Cys Ala Gly
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: Synthetic Construct

<400> SEQUENCE: 84

Arg Asp Thr Ile Ser Arg Asp Asn Thr Lys Asn Ala Gly Asp Leu Gln
1               5                   10                  15

Met Asn Ser Leu Lys Pro Glu Asp Ser Ala Thr Tyr Tyr Cys Ala Val
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: Synthetic Construct

<400> SEQUENCE: 85

Arg Phe Val Ile Ser Lys Asp Asn Val Lys Ser Thr Val Phe Leu Gln
1               5                   10                  15

Met Asn Ser Leu Lys Pro Glu Asp Ser Ala Val Tyr Tyr Cys Ala Leu
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Synthetic Construct
```

```
<400> SEQUENCE: 86

Arg Asp Thr Ile Ser Lys Asp His Thr Lys Asn Ala Val Asp Leu Gln
1               5                   10                  15

Met Asn Ser Leu Lys Pro Glu Asp Ser Ala Thr Tyr Tyr Cys Ala Val
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Synthetic Construct

<400> SEQUENCE: 87

Arg Phe Thr Val Ser Arg Asp Tyr Ser Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 88
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 88

Xaa Gly Xaa Gly Thr Xaa Val Thr Xaa Ser Ser
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthetic Construct

<400> SEQUENCE: 89

Trp Gly Gln Gly Thr Gln Val Thr Val Ser Ser
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Synthetic Construct

<400> SEQUENCE: 90

Trp Gly Arg Gly Thr Gln Val Thr Val Ser Ser
1               5                   10
```

<210> SEQ ID NO 91
<211> LENGTH: 11
<212> TYPE: PRT
<213> ORGANISM: Artificial Sequence
<220> FEATURE:
<223> OTHER INFORMATION: Synthetic Construct

<400> SEQUENCE: 91

Ser Gly Gln Gly Thr Gln Val Thr Val Ser Ser
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic Construct

<400> SEQUENCE: 92

Trp Gly Gln Gly Thr Glu Val Thr Ile Ser Ser
1               5                   10

<210> SEQ ID NO 93
<211> LENGTH: 132
<212> TYPE: PRT
<213> ORGANISM: Artificial Sequence
<220> FEATURE:
<223> OTHER INFORMATION: Synthetic Construct

<400> SEQUENCE: 93

Gln Val Lys Leu Glu Glu Ser Gly Gly Gly Leu Val Gln Ala Gly Gly
1               5                   10                  15

Ser Leu Arg Leu Ser Cys Val Ala Ser Gly Arg Thr Ile Asn Asp Tyr
            20                  25                  30

Ile Leu Gly Trp Phe Arg Gln Ala Pro Gly Lys Lys Arg Glu Phe Val
        35                  40                  45

Ala Ala Ile Arg Gly Ser Gly Ala Ile Arg Gly Arg Glu Gly Ser Thr
    50                  55                  60

Phe Tyr Val Asp Ser Val Lys Gly Arg Tyr Thr Ile Ser Lys Asp Asn
65                  70                  75                  80

Ala Lys Asn Thr Val Asp Leu Gln Met Asn Ser Leu Lys Pro Glu Asp
                85                  90                  95

Ser Ala Thr Tyr Tyr Cys Ala Val Asp Arg Phe Pro Thr Pro Glu Phe
            100                 105                 110

Ser Thr Gln Val Gly His Tyr Asp Tyr Trp Gly Gln Gly Thr Gln Val
        115                 120                 125

Thr Val Ser Ser
    130

<210> SEQ ID NO 94
<211> LENGTH: 132
<212> TYPE: PRT
<213> ORGANISM: Artificial Sequence
<220> FEATURE:
<223> OTHER INFORMATION: Synthetic Construct

<400> SEQUENCE: 94

Gln Val Gln Leu Val Glu Ser Gly Gly Gly Leu Val Gln Ala Gly Gly
1               5                   10                  15

Ser Leu Arg Leu Ser Cys Leu Ala Ser Asp Arg Thr Val Asn Asn Tyr
            20                  25                  30

-continued

Ile Val Gly Tyr Phe Arg Gln Ala Pro Gly Lys Glu Arg Glu Phe Val
            35                  40                  45

Ala Ala Ile Arg Gly Ser Gly Ala Ile Arg Gly Arg Glu Gly Ser Thr
 50                  55                  60

Tyr Tyr Ala Asp Ser Val Lys Gly Arg Phe Ser Ile Ser Lys Asp Asn
 65                  70                  75                  80

Ala Lys Asn Thr Ile Tyr Leu Gln Met Asn Ser Leu Lys Pro Glu Asp
                 85                  90                  95

Ser Ala Val Tyr Tyr Cys Ala Leu Asp Arg Phe Pro Thr Pro Glu Phe
                100                 105                 110

Thr Thr Gln Val Gly His Tyr Asp Val Trp Gly Arg Gly Thr Gln Val
            115                 120                 125

Thr Val Ser Ser
        130

<210> SEQ ID NO 95
<211> LENGTH: 126
<212> TYPE: PRT
<213> ORGANISM: Artificial Sequence
<220> FEATURE:
<223> OTHER INFORMATION: Synthetic Construct

<400> SEQUENCE: 95

Gln Val Lys Leu Glu Glu Ser Gly Gly Gly Leu Val Gln Ala Gly Gly
 1               5                  10                  15

Ser Leu Arg Leu Ser Cys Val Ala Ser Gly Arg Thr Ile Asn Asp Tyr
                 20                  25                  30

Ile Leu Gly Trp Phe Arg Gln Ala Pro Gly Lys Lys Arg Glu Phe Val
            35                  40                  45

Ala Ala Ile Arg Glu Ser Gly Ser Ser Thr Tyr Tyr Ala Asp Ser Val
 50                  55                  60

Lys Gly Arg Tyr Thr Ile Ser Arg Asn Asn Thr Lys Asn Ala Val Asp
 65                  70                  75                  80

Leu Gln Met Asn Ser Leu Lys Pro Glu Asp Ser Ala Thr Tyr Tyr Cys
                 85                  90                  95

Ala Val Asp Gln Tyr Pro Thr Pro Glu Phe Ser Thr Gln Val Gly His
                100                 105                 110

Tyr Asp Tyr Trp Gly Gln Gly Thr Gln Val Thr Val Ser Ser
            115                 120                 125

<210> SEQ ID NO 96
<211> LENGTH: 126
<212> TYPE: PRT
<213> ORGANISM: Artificial Sequence
<220> FEATURE:
<223> OTHER INFORMATION: Synthetic Construct

<400> SEQUENCE: 96

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Pro Arg His Tyr
                 20                  25                  30

Ile Leu Gly Trp Phe Arg Gln Ala Pro Gly Lys Gln Arg Glu Phe Val
            35                  40                  45

Ala Ala Ile Arg Glu Ser Gly Ser Ser Thr Tyr Tyr Ala Asp Ser Val
 50                  55                  60

Lys Gly Arg Tyr Thr Ile Ser Arg Asp Asn Thr Lys Asn Ala Val Asp
 65                  70                  75                  80

```
Leu Gln Met Asn Ser Leu Lys Pro Glu Asp Ser Ala Thr Tyr Tyr Cys
                 85                  90                  95

Ala Val Asp Gln Tyr Pro Thr Pro Glu Phe Ser Thr Val Gly His
            100                 105                 110

Tyr Asp Tyr Trp Gly Gln Gly Thr Gln Val Thr Val Ser Ser
        115                 120                 125

<210> SEQ ID NO 97
<211> LENGTH: 127
<212> TYPE: PRT
<213> ORGANISM: Artificial Sequence
<220> FEATURE:
<223> OTHER INFORMATION: Synthetic Construct

<400> SEQUENCE: 97

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Val Tyr
            20                  25                  30

Ala Met Gly Trp Phe Arg Gln Ala Pro Gly Lys Glu Arg Glu Phe Val
        35                  40                  45

Ala Ala Ile Thr Ser Pro Gly Asp Ser Ile Pro Tyr Ala His Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Ala Tyr Tyr Cys
                85                  90                  95

Ala Ala Thr Lys Ser Gly Asn Tyr Asn Tyr Met Gly Pro Asp Pro Lys
            100                 105                 110

Lys Tyr His Tyr Trp Gly Gln Gly Thr Gln Val Thr Val Ser Ser
        115                 120                 125

<210> SEQ ID NO 98
<211> LENGTH: 127
<212> TYPE: PRT
<213> ORGANISM: Artificial Sequence
<220> FEATURE:
<223> OTHER INFORMATION: Synthetic Construct

<400> SEQUENCE: 98

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Val Tyr
            20                  25                  30

Ala Met Gly Trp Phe Arg Gln Ala Pro Gly Lys Glu Arg Glu Phe Val
        35                  40                  45

Thr Ala Ile Thr Ser Ser Gly Asp Ser Ile Pro Tyr Ala His Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Thr Thr Ser Gly Thr Tyr Asn Tyr Met Gly Pro Asp Pro Lys
            100                 105                 110

Glu Tyr Val Tyr Trp Gly Gln Gly Thr Gln Val Thr Val Ser Ser
        115                 120                 125
```

<210> SEQ ID NO 99
<211> LENGTH: 127
<212> TYPE: PRT
<213> ORGANISM: Artificial Sequence
<220> FEATURE:
<223> OTHER INFORMATION: Synthetic Construct

<400> SEQUENCE: 99

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn Asp Tyr
            20                  25                  30

Ala Met Gly Trp Phe Arg Gln Ala Pro Gly Lys Glu Arg Glu Phe Val
        35                  40                  45

Ala Ala Ala Ala Gln Ser Gly Asp Ser Ser Ala Tyr Ala Arg Ser Val
    50                  55                  60

Lys Gly Arg Phe Thr Ile Ser Arg Asp Gly Ala Lys Asn Thr Ala Tyr
65                  70                  75                  80

Leu Gln Met Asp Ser Leu Lys Pro Glu Asp Thr Ala Ala Tyr Tyr Cys
                85                  90                  95

Ala Ala Thr Thr Arg Gly Ser Tyr Glu Tyr Met Gly Pro Asp Pro Lys
            100                 105                 110

Lys Tyr Glu Tyr Trp Gly Gln Gly Thr Gln Val Thr Val Ser Ser
        115                 120                 125
```

<210> SEQ ID NO 100
<211> LENGTH: 123
<212> TYPE: PRT
<213> ORGANISM: Artificial Sequence
<220> FEATURE:
<223> OTHER INFORMATION: Synthetic Construct

<400> SEQUENCE: 100

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Phe Ser Asn Tyr
            20                  25                  30

Ala Met Gly Trp Phe Arg Gln Ala Pro Gly Thr Glu Arg Glu Phe Val
        35                  40                  45

Gly Gln Ile Ser Gln Val Asp Gly Phe Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Ala Leu Ala Phe Pro Thr Thr Ser Ser Asn Thr Tyr Ala Tyr
            100                 105                 110

Ser Gly Gln Gly Thr Gln Val Thr Val Ser Ser
        115                 120
```

<210> SEQ ID NO 101
<211> LENGTH: 127
<212> TYPE: PRT
<213> ORGANISM: Artificial Sequence
<220> FEATURE:
<223> OTHER INFORMATION: Synthetic Construct

<400> SEQUENCE: 101

Gln Val Lys Leu Glu Glu Ser Gly Gly Gly Leu Val Gln Ala Gly Gly
1               5                   10                  15

Ser Leu Arg Leu Ser Cys Ser Pro Ser Asp Arg Thr Phe Ser Ala Tyr
            20                  25                  30

Ala Met Gly Trp Phe Arg Gln Val Pro Gly Arg Glu Arg Glu Phe Val
        35                  40                  45

Ala Thr Ile Arg Asp Ser Asp Ala Ser Ile Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Ile Pro Asp Asp Thr Ala Val Tyr Tyr Cys
                85                  90                  95

Ala Ala Arg Gln Tyr Tyr Ser Gly Arg Val Tyr Ser Thr Phe Arg Glu
            100                 105                 110

Glu Tyr Asp Tyr Trp Gly Gln Gly Thr Gln Val Thr Val Ser Ser
            115                 120                 125

<210> SEQ ID NO 102
<211> LENGTH: 121
<212> TYPE: PRT
<213> ORGANISM: Artificial Sequence
<220> FEATURE:
<223> OTHER INFORMATION: Synthetic Construct

<400> SEQUENCE: 102

Gln Val Lys Leu Glu Glu Ser Gly Gly Gly Leu Val Gln Ala Gly Gly
1               5                   10                  15

Ser Leu Arg Leu Ser Cys Ala Ala Pro Arg Ser Gly Val Val Ile Ala
            20                  25                  30

Tyr Met Ala Trp Tyr Arg Gln Ala Pro Glu Lys Gln Arg Glu Leu Val
        35                  40                  45

Ala Ser Ile Ser Ser Gly Gly Thr Thr Asn Tyr Ala Val Phe Ala Lys
    50                  55                  60

Gly Arg Phe Thr Ile Ser Ala Asp Asn Ala Lys Asn Thr Val Tyr Leu
65                  70                  75                  80

Gln Met Asn Ser Leu Lys Pro Glu Asp Thr Ala Val Tyr Ile Cys Asn
                85                  90                  95

Ala Tyr Ala Met Ser Thr Glu Thr Met Val Ser Gln Asp Tyr Trp Gly
            100                 105                 110

Gln Gly Thr Gln Val Thr Val Ser Ser
            115                 120

<210> SEQ ID NO 103
<211> LENGTH: 127
<212> TYPE: PRT
<213> ORGANISM: Artificial Sequence
<220> FEATURE:
<223> OTHER INFORMATION: Synthetic Construct

<400> SEQUENCE: 103

Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Phe Ser Asn Tyr
            20                  25                  30

Ala Met Gly Trp Phe Arg Gln Ala Pro Gly Ala Glu Arg Glu Phe Val
        35                  40                  45

Gly Gln Ile Ser Gln Val Gly Phe Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Asp Asp Thr Ala Val Tyr Tyr Cys
                85                  90                  95

Ala Ala Thr Tyr Ser Gly Thr Tyr Asn Tyr Met Gly Ala Asp Pro Lys
            100                 105                 110

Glu Tyr Val Tyr Trp Gly Gln Gly Thr Gln Val Thr Val Ser Ser
            115                 120                 125

<210> SEQ ID NO 104
<211> LENGTH: 124
<212> TYPE: PRT
<213> ORGANISM: Artificial Sequence
<220> FEATURE:
<223> OTHER INFORMATION: Synthetic Construct

<400> SEQUENCE: 104

Gln Val Lys Leu Glu Glu Ser Gly Gly Gly Pro Val Gln Ala Gly Gly
1               5                   10                  15

Ser Leu Arg Leu Ser Cys Leu Ala Ser Gly Arg Phe Val Asn Ser Pro
            20                  25                  30

Thr Met Ala Trp Phe Arg Gln Ala Pro Gly Glu Glu Arg Lys Phe Val
        35                  40                  45

Ala Ala Ile Arg Ser Arg Asp Asp Ser Thr Tyr Tyr Ser Asn Ser Val
    50                  55                  60

Lys Gly Arg Phe Thr Ile Ser Leu Asp Asn Ala Lys Asn Thr Ala Tyr
65                  70                  75                  80

Leu Arg Met Asp Ser Leu Gln Pro Glu Asp Thr Ala Val Tyr Tyr Cys
                85                  90                  95

Ala Gly Asp Pro Arg Thr Ile Asp Leu Ser Ser Arg Leu Leu Trp Gly
            100                 105                 110

Ser Trp Gly Gln Gly Thr Gln Val Thr Val Ser Ser
            115                 120

<210> SEQ ID NO 105
<211> LENGTH: 126
<212> TYPE: PRT
<213> ORGANISM: Artificial Sequence
<220> FEATURE:
<223> OTHER INFORMATION: Synthetic Construct

<400> SEQUENCE: 105

Gln Val Gln Leu Val Glu Ser Gly Gly Gly Leu Val Gln Ala Gly Gly
1               5                   10                  15

Ser Met Arg Leu Ser Cys Ala Ala Ser Gly Arg Thr Pro Arg His Tyr
            20                  25                  30

Ile Leu Gly Trp Phe Arg Gln Ala Pro Gly Lys Gln Arg Glu Phe Val
        35                  40                  45

Ala Ala Ile Arg Glu Ser Gly Ser Arg Thr Tyr Tyr Ala Asp Ser Val
    50                  55                  60

Arg Gly Arg Asp Thr Ile Ser Arg Asp Asn Lys Asn Ala Gly Asp
65                  70                  75                  80

Leu Gln Met Asn Ser Leu Lys Pro Glu Asp Ser Ala Thr Tyr Tyr Cys
                85                  90                  95

Ala Val Asp Gln Tyr Pro Thr Thr Glu Phe Ser Thr Gln Val Gly His
            100                 105                 110

Tyr Asp Tyr Trp Gly Gln Gly Thr Glu Val Thr Ile Ser Ser
        115                 120                 125

<210> SEQ ID NO 106
<211> LENGTH: 126
<212> TYPE: PRT
<213> ORGANISM: Artificial Sequence
<220> FEATURE:
<223> OTHER INFORMATION: Synthetic Construct

<400> SEQUENCE: 106

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Pro Arg His Tyr
            20                  25                  30

Ile Val Gly Trp Phe Arg Gln Ala Pro Gly Lys Glu Arg Glu Phe Val
        35                  40                  45

Ala Ala Val Arg Glu Ser Gly Ser Ser Thr Glu Tyr Ala Glu Asn Val
    50                  55                  60

Lys Gly Arg Phe Val Ile Ser Lys Asp Asn Val Lys Ser Thr Val Phe
65                  70                  75                  80

Leu Gln Met Asn Ser Leu Lys Pro Glu Asp Ser Ala Val Tyr Tyr Cys
                85                  90                  95

Ala Leu Asp Arg Phe Pro Thr Pro Glu Phe Ser Asp Arg Val Gly His
            100                 105                 110

Tyr Asp Leu Trp Gly Gln Gly Thr Gln Val Thr Val Ser Ser
        115                 120                 125

<210> SEQ ID NO 107
<211> LENGTH: 126
<212> TYPE: PRT
<213> ORGANISM: Artificial Sequence
<220> FEATURE:
<223> OTHER INFORMATION: Synthetic Construct

<400> SEQUENCE: 107

Gln Val Gln Leu Val Glu Ser Gly Gly Gly Leu Val Gln Ala Gly Gly
1               5                   10                  15

Ser Met Arg Leu Ser Cys Ala Ala Ser Gly Arg Thr Pro Arg His Tyr
            20                  25                  30

Ile Leu Gly Trp Phe Arg Gln Ala Pro Gly Lys Gln Arg Glu Phe Val
        35                  40                  45

Ala Ala Ile Arg Glu Ser Gly Ser Arg Thr Tyr Tyr Ala Asp Ser Val
    50                  55                  60

Arg Gly Arg Tyr Thr Ile Ser Arg Asp Asn Thr Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Gln Tyr Pro Thr Pro Glu Phe Ser Thr Gln Val Gly His
            100                 105                 110

Tyr Asp Tyr Trp Gly Gln Gly Thr Gln Val Thr Val Ser Ser
        115                 120                 125

<210> SEQ ID NO 108
<211> LENGTH: 126
<212> TYPE: PRT
<213> ORGANISM: Artificial Sequence
<220> FEATURE:
<223> OTHER INFORMATION: Synthetic Construct

<400> SEQUENCE: 108

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Pro Arg His Tyr
            20                  25                  30

Ile Leu Gly Trp Phe Arg Gln Ala Pro Gly Lys Leu Pro Glu Phe Val
        35                  40                  45

Ala Ala Val Arg Glu Pro Gly Ser Ser Thr Tyr Tyr Ala Asp Ser Val
    50                  55                  60

Lys Gly Arg Asp Thr Ile Ser Lys Asp His Thr Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Pro Tyr Pro Thr Pro Glu Phe Thr Thr His Val Gly His
            100                 105                 110

Tyr Asp Tyr Trp Gly Gln Gly Thr Gln Val Thr Val Ser Ser
        115                 120                 125

<210> SEQ ID NO 109
<211> LENGTH: 132
<212> TYPE: PRT
<213> ORGANISM: Artificial Sequence
<220> FEATURE:
<223> OTHER INFORMATION: Synthetic Construct

<400> SEQUENCE: 109

Gln Val Lys Leu Glu Glu Ser Gly Gly Gly Leu Val Gln Ala Gly Asp
1               5                   10                  15

Ser Leu Arg Leu Ser Cys Ala Ala Ser Gly Arg Ile Phe Asn His Tyr
            20                  25                  30

Val Thr Ser Trp Phe Arg Gln Ala Pro Asp Gln Glu Arg Glu Phe Val
        35                  40                  45

Ala Gly Val Thr Ala His Ala Gly Val Thr Ala Asp Val Glu Ser Thr
    50                  55                  60

Asp Tyr Ser Asp Ser Val Lys Gly Arg Phe Thr Val Ser Arg Asp Tyr
65                  70                  75                  80

Ser Lys Asn Thr Val Tyr Leu Gln Met Asn Ser Leu Lys Pro Glu Asp
                85                  90                  95

Thr Ala Val Tyr Tyr Cys Ala Ala Pro Ser Gly Phe Tyr Arg Thr Ile
            100                 105                 110

Pro His Val His Ser Asn Tyr Asp His Trp Gly Gln Gly Thr Gln Val
        115                 120                 125

Thr Val Ser Ser
    130

<210> SEQ ID NO 110
<211> LENGTH: 187
<212> TYPE: PRT
<213> ORGANISM: Artificial Sequence
<220> FEATURE:
<223> OTHER INFORMATION: Synthetic Construct

<400> SEQUENCE: 110

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
        35                  40                  45

Val Lys Leu Glu Glu Ser Gly Gly Leu Val Gln Ala Gly Gly Ser
50                  55                  60

Leu Arg Leu Ser Cys Val Ala Ser Gly Arg Thr Ile Asn Asp Tyr Ile
65                  70                  75                  80

Leu Gly Trp Phe Arg Gln Ala Pro Gly Lys Arg Glu Phe Val Ala
                85                  90                  95

Ala Ile Arg Gly Ser Gly Ala Ile Arg Gly Arg Glu Gly Ser Thr Phe
                100                 105                 110

Tyr Val Asp Ser Val Lys Gly Arg Tyr Thr Ile Ser Lys Asp Asn Ala
            115                 120                 125

Lys Asn Thr Val Asp Leu Gln Met Asn Ser Leu Lys Pro Glu Asp Ser
        130                 135                 140

Ala Thr Tyr Tyr Cys Ala Val Asp Arg Phe Pro Thr Pro Glu Phe Ser
145                 150                 155                 160

Thr Gln Val Gly His Tyr Asp Tyr Trp Gly Gln Gly Thr Gln Val Thr
                165                 170                 175

Val Ser Ser Gly Ser His His His His His His
            180                 185

<210> SEQ ID NO 111
<211> LENGTH: 187
<212> TYPE: PRT
<213> ORGANISM: Artificial Sequence
<220> FEATURE:
<223> OTHER INFORMATION: Synthetic Construct

<400> SEQUENCE: 111

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
        35                  40                  45

Val Gln Leu Val Glu Ser Gly Gly Gly Leu Val Gln Ala Gly Gly Ser
50                  55                  60

Leu Arg Leu Ser Cys Leu Ala Ser Asp Arg Thr Val Asn Asn Tyr Ile
65                  70                  75                  80

Val Gly Tyr Phe Arg Gln Ala Pro Gly Lys Glu Arg Glu Phe Val Ala
                85                  90                  95

Ala Ile Arg Gly Ser Gly Ala Ile Arg Gly Arg Glu Gly Ser Thr Tyr
                100                 105                 110

Tyr Ala Asp Ser Val Lys Gly Arg Phe Ser Ile Ser Lys Asp Asn Ala
            115                 120                 125

Lys Asn Thr Ile Tyr Leu Gln Met Asn Ser Leu Lys Pro Glu Asp Ser
        130                 135                 140

Ala Val Tyr Tyr Cys Ala Leu Asp Arg Phe Pro Thr Pro Glu Phe Thr
145                 150                 155                 160

Thr Gln Val Gly His Tyr Asp Val Trp Gly Arg Gly Thr Gln Val Thr
            165                 170                 175

Val Ser Ser Gly Ser His His His His His
        180                 185

<210> SEQ ID NO 112
<211> LENGTH: 181
<212> TYPE: PRT
<213> ORGANISM: Artificial Sequence
<220> FEATURE:
<223> OTHER INFORMATION: Synthetic Construct

<400> SEQUENCE: 112

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
        35                  40                  45

Val Lys Leu Glu Glu Ser Gly Gly Gly Leu Val Gln Ala Gly Gly Ser
    50                  55                  60

Leu Arg Leu Ser Cys Val Ala Ser Gly Arg Thr Ile Asn Asp Tyr Ile
65                  70                  75                  80

Leu Gly Trp Phe Arg Gln Ala Pro Gly Lys Lys Arg Glu Phe Val Ala
                85                  90                  95

Ala Ile Arg Glu Ser Gly Ser Ser Thr Tyr Tyr Ala Asp Ser Val Lys
            100                 105                 110

Gly Arg Tyr Thr Ile Ser Arg Asn Asn Thr Lys Asn Ala Val Asp Leu
        115                 120                 125

Gln Met Asn Ser Leu Lys Pro Glu Asp Ser Ala Thr Tyr Tyr Cys Ala
    130                 135                 140

Val Asp Gln Tyr Pro Thr Pro Glu Phe Ser Thr Gln Val Gly His Tyr
145                 150                 155                 160

Asp Tyr Trp Gly Gln Gly Thr Gln Val Thr Val Ser Ser Gly Ser His
                165                 170                 175

His His His His His
        180

<210> SEQ ID NO 113
<211> LENGTH: 181
<212> TYPE: PRT
<213> ORGANISM: Artificial Sequence
<220> FEATURE:
<223> OTHER INFORMATION: Synthetic Construct

<400> SEQUENCE: 113

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
        35                  40                  45

Val Gln Leu Val Glu Ser Gly Gly Gly Leu Val Gln Ala Gly Gly Ser
    50                  55                  60

Leu Arg Leu Ser Cys Ala Ala Ser Gly Arg Thr Pro Arg His Tyr Ile
65                  70                  75                  80

Leu Gly Trp Phe Arg Gln Ala Pro Gly Lys Gln Arg Glu Phe Val Ala
                85                  90                  95

```
Ala Ile Arg Glu Ser Gly Ser Ser Thr Tyr Tyr Ala Asp Ser Val Lys
            100                 105                 110

Gly Arg Tyr Thr Ile Ser Arg Asp Asn Thr Lys Asn Ala Val Asp Leu
        115                 120                 125

Gln Met Asn Ser Leu Lys Pro Glu Asp Ser Ala Thr Tyr Tyr Cys Ala
    130                 135                 140

Val Asp Gln Tyr Pro Thr Pro Glu Phe Ser Thr Gln Val Gly His Tyr
145                 150                 155                 160

Asp Tyr Trp Gly Gln Gly Thr Gln Val Thr Val Ser Ser Gly Ser His
                165                 170                 175

His His His His His
            180

<210> SEQ ID NO 114
<211> LENGTH: 182
<212> TYPE: PRT
<213> ORGANISM: Artificial Sequence
<220> FEATURE:
<223> OTHER INFORMATION: Synthetic Construct

<400> SEQUENCE: 114

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
        35                  40                  45

Val Gln Leu Val Glu Ser Gly Gly Gly Leu Val Gln Ala Gly Gly Ser
50                  55                  60

Leu Arg Leu Ser Cys Ala Ala Ser Gly Arg Thr Phe Ser Val Tyr Ala
65                  70                  75                  80

Met Gly Trp Phe Arg Gln Ala Pro Gly Lys Glu Arg Glu Phe Val Ala
                85                  90                  95

Ala Ile Thr Ser Pro Gly Asp Ser Ile Pro Tyr Ala His Ser Val Lys
            100                 105                 110

Gly Arg Phe Thr Ile Ser Arg Asp Asn Ala Lys Asn Thr Leu Tyr Leu
        115                 120                 125

Gln Met Asn Ser Leu Lys Pro Glu Asp Thr Ala Tyr Tyr Cys Ala
    130                 135                 140

Ala Thr Lys Ser Gly Asn Tyr Asn Tyr Met Gly Pro Asp Pro Lys Lys
145                 150                 155                 160

Tyr His Tyr Trp Gly Gln Gly Thr Gln Val Thr Val Ser Ser Gly Ser
                165                 170                 175

His His His His His His
            180

<210> SEQ ID NO 115
<211> LENGTH: 182
<212> TYPE: PRT
<213> ORGANISM: Artificial Sequence
<220> FEATURE:
<223> OTHER INFORMATION: Synthetic Construct

<400> SEQUENCE: 115

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30
```

```
Asp Gly Lys Pro Ile Pro Asn Pro Leu Leu Gly Leu Asp Ser Thr Gln
            35                  40                  45

Val Lys Leu Glu Glu Ser Gly Gly Leu Val Gln Ala Gly Gly Ser
 50                  55                  60

Leu Arg Leu Ser Cys Ala Ala Ser Gly Arg Thr Phe Ser Val Tyr Ala
 65                  70                  75                  80

Met Gly Trp Phe Arg Gln Ala Pro Gly Lys Glu Arg Glu Phe Val Thr
                 85                  90                  95

Ala Ile Thr Ser Ser Gly Asp Ser Ile Pro Tyr Ala His Ser Val Lys
            100                 105                 110

Gly Arg Phe Thr Ile Ser Arg Asp Asn Ala Lys Asn Thr Val Tyr Leu
            115                 120                 125

Gln Met Asn Ser Leu Lys Pro Glu Asp Thr Ala Ala Tyr Tyr Cys Ala
    130                 135                 140

Ala Thr Thr Ser Gly Thr Tyr Asn Tyr Met Gly Pro Asp Pro Lys Glu
145                 150                 155                 160

Tyr Val Tyr Trp Gly Gln Gly Thr Gln Val Thr Val Ser Ser Gly Ser
                165                 170                 175

His His His His His His
            180

<210> SEQ ID NO 116
<211> LENGTH: 193
<212> TYPE: PRT
<213> ORGANISM: Artificial Sequence
<220> FEATURE:
<223> OTHER INFORMATION: Synthetic Construct

<400> SEQUENCE: 116

Met Gly Thr Val Ser Ser Arg Arg Ser Trp Trp Pro Leu Pro Leu Leu
 1               5                  10                  15

Leu Leu Leu Leu Leu Leu Leu Gly Pro Ala Gly Ala Arg Ala Gln Glu
                20                  25                  30

Asp Gly Lys Pro Ile Pro Asn Pro Leu Leu Gly Leu Asp Ser Thr Gln
            35                  40                  45

Val Lys Leu Glu Glu Ser Gly Gly Leu Val Gln Ala Gly Gly Ser
 50                  55                  60

Leu Arg Leu Ser Cys Ala Ala Ser Gly Arg Thr Phe Asn Asp Tyr Ala
 65                  70                  75                  80

Met Gly Trp Phe Arg Gln Ala Pro Gly Lys Glu Arg Glu Phe Val Ala
                 85                  90                  95

Ala Ala Ala Gln Ser Gly Asp Ser Ser Ala Tyr Ala Arg Ser Val Lys
            100                 105                 110

Gly Arg Phe Thr Ile Ser Arg Asp Gly Ala Lys Asn Thr Ala Tyr Leu
            115                 120                 125

Gln Met Asp Ser Leu Lys Pro Glu Asp Thr Ala Ala Tyr Tyr Cys Ala
    130                 135                 140

Ala Thr Thr Arg Gly Ser Tyr Glu Tyr Met Gly Pro Asp Pro Lys Lys
145                 150                 155                 160

Tyr Glu Tyr Trp Gly Gln Gly Thr Gln Val Thr Val Ser Ser Gly Ser
                165                 170                 175

Glu Gln Lys Leu Ile Ser Glu Glu Asp Leu Asn His His His His His
            180                 185                 190

His
```

-continued

```
<210> SEQ ID NO 117
<211> LENGTH: 189
<212> TYPE: PRT
<213> ORGANISM: Artificial Sequence
<220> FEATURE:
<223> OTHER INFORMATION: Synthetic Construct

<400> SEQUENCE: 117

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
        35                  40                  45

Val Lys Leu Glu Glu Ser Gly Gly Gly Leu Val Gln Ala Gly Gly Ser
    50                  55                  60

Leu Arg Leu Ser Cys Ala Ala Ser Gly Leu Thr Phe Ser Asn Tyr Ala
65                  70                  75                  80

Met Gly Trp Phe Arg Gln Ala Pro Gly Thr Glu Arg Glu Phe Val Gly
                85                  90                  95

Gln Ile Ser Gln Val Asp Gly Phe Thr Tyr Tyr Glu Asp Ser Val Lys
            100                 105                 110

Gly Arg Phe Thr Ile Ser Arg Asp Asn Ala Lys Asn Thr Val Tyr Leu
        115                 120                 125

Gln Met Asn Ser Leu Lys Pro Asp Thr Ala Val Tyr Tyr Cys Ala
    130                 135                 140

Ala Ala Leu Ala Phe Pro Thr Thr Ser Ser Asn Thr Tyr Ala Tyr Ser
145                 150                 155                 160

Gly Gln Gly Thr Gln Val Thr Val Ser Ser Gly Ser Glu Gln Lys Leu
                165                 170                 175

Ile Ser Glu Glu Asp Leu Asn His His His His His His
            180                 185

<210> SEQ ID NO 118
<211> LENGTH: 182
<212> TYPE: PRT
<213> ORGANISM: Artificial Sequence
<220> FEATURE:
<223> OTHER INFORMATION: Synthetic Construct

<400> SEQUENCE: 118

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
        35                  40                  45

Val Lys Leu Glu Glu Ser Gly Gly Gly Leu Val Gln Ala Gly Gly Ser
    50                  55                  60

Leu Arg Leu Ser Cys Ser Pro Ser Asp Arg Thr Phe Ser Ala Tyr Ala
65                  70                  75                  80

Met Gly Trp Phe Arg Gln Val Pro Gly Arg Glu Arg Glu Phe Val Ala
                85                  90                  95

Thr Ile Arg Asp Ser Asp Ala Ser Ile Tyr Tyr Thr Asp Ser Val Lys
            100                 105                 110

Gly Arg Phe Thr Ile Ser Arg Asp Asn Ala Lys Asn Thr Val Tyr Leu
        115                 120                 125
```

Gln Met Asn Ser Leu Ile Pro Asp Asp Thr Ala Val Tyr Tyr Cys Ala
            130                 135                 140

Ala Arg Gln Tyr Tyr Ser Gly Arg Val Tyr Ser Thr Phe Arg Glu Glu
145                 150                 155                 160

Tyr Asp Tyr Trp Gly Gln Gly Thr Gln Val Thr Val Ser Ser Gly Ser
                165                 170                 175

His His His His His His
            180

<210> SEQ ID NO 119
<211> LENGTH: 176
<212> TYPE: PRT
<213> ORGANISM: Artificial Sequence
<220> FEATURE:
<223> OTHER INFORMATION: Synthetic Construct

<400> SEQUENCE: 119

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Gly Lys Pro Ile Pro Asn Pro Leu Leu Gly Leu Asp Ser Thr Gln
            35                  40                  45

Val Lys Leu Glu Glu Ser Gly Gly Gly Leu Val Gln Ala Gly Gly Ser
50                  55                  60

Leu Arg Leu Ser Cys Ala Ala Pro Arg Ser Gly Val Val Ile Ala Tyr
65                  70                  75                  80

Met Ala Trp Tyr Arg Gln Ala Pro Glu Lys Gln Arg Glu Leu Val Ala
                85                  90                  95

Ser Ile Ser Ser Gly Gly Thr Thr Asn Tyr Ala Val Phe Ala Lys Gly
            100                 105                 110

Arg Phe Thr Ile Ser Ala Asp Asn Ala Lys Asn Thr Val Tyr Leu Gln
            115                 120                 125

Met Asn Ser Leu Lys Pro Glu Asp Thr Ala Val Tyr Ile Cys Asn Ala
            130                 135                 140

Tyr Ala Met Ser Thr Glu Thr Met Val Ser Gln Asp Tyr Trp Gly Gln
145                 150                 155                 160

Gly Thr Gln Val Thr Val Ser Ser Gly Ser His His His His His His
                165                 170                 175

<210> SEQ ID NO 120
<211> LENGTH: 146
<212> TYPE: PRT
<213> ORGANISM: Artificial Sequence
<220> FEATURE:
<223> OTHER INFORMATION: Synthetic Construct

<400> SEQUENCE: 120

Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Phe Ser Asn Tyr
            20                  25                  30

Ala Met Gly Trp Phe Arg Gln Ala Pro Gly Ala Glu Arg Glu Phe Val
            35                  40                  45

Gly Gln Ile Ser Gln Val Asp Gly Phe Thr Tyr Tyr Glu Asp Ser Val
            50                  55                  60

Lys Gly Arg Phe Thr Ile Ser Arg Asp Asn Ala Lys Asn Thr Val Tyr
65                  70                  75                  80

```
Leu Gln Met Ser Ser Leu Lys Pro Asp Asp Thr Ala Val Tyr Tyr Cys
                85                  90                  95

Ala Ala Thr Tyr Ser Gly Thr Tyr Asn Tyr Met Gly Ala Asp Pro Lys
            100                 105                 110

Glu Tyr Val Tyr Trp Gly Gln Gly Thr Gln Val Thr Val Ser Ser Gly
        115                 120                 125

Ser Glu Gln Lys Leu Ile Ser Glu Glu Asp Leu Asn His His His His
    130                 135                 140

His His
145

<210> SEQ ID NO 121
<211> LENGTH: 132
<212> TYPE: PRT
<213> ORGANISM: Artificial Sequence
<220> FEATURE:
<223> OTHER INFORMATION: Synthetic Construct

<400> SEQUENCE: 121

Gln Val Lys Leu Glu Glu Ser Gly Gly Gly Pro Val Gln Ala Gly Gly
1               5                   10                  15

Ser Leu Arg Leu Ser Cys Leu Ala Ser Gly Arg Phe Val Asn Ser Pro
            20                  25                  30

Thr Met Ala Trp Phe Arg Gln Ala Pro Gly Glu Glu Arg Lys Phe Val
        35                  40                  45

Ala Ala Ile Arg Ser Arg Asp Asp Ser Thr Tyr Tyr Ser Asn Ser Val
    50                  55                  60

Lys Gly Arg Phe Thr Ile Ser Leu Asp Asn Ala Lys Asn Thr Ala Tyr
65                  70                  75                  80

Leu Arg Met Asp Ser Leu Gln Pro Glu Asp Thr Ala Val Tyr Tyr Cys
                85                  90                  95

Ala Gly Asp Pro Arg Thr Ile Asp Leu Ser Ser Arg Leu Leu Trp Gly
            100                 105                 110

Ser Trp Gly Gln Gly Thr Gln Val Thr Val Ser Ser Gly Ser His His
        115                 120                 125

His His His His
    130

<210> SEQ ID NO 122
<211> LENGTH: 134
<212> TYPE: PRT
<213> ORGANISM: Artificial Sequence
<220> FEATURE:
<223> OTHER INFORMATION: Synthetic Construct

<400> SEQUENCE: 122

Gln Val Gln Leu Val Glu Ser Gly Gly Gly Leu Val Gln Ala Gly Gly
1               5                   10                  15

Ser Met Arg Leu Ser Cys Ala Ala Ser Gly Arg Thr Pro Arg His Tyr
            20                  25                  30

Ile Leu Gly Trp Phe Arg Gln Ala Pro Gly Lys Gln Arg Glu Phe Val
        35                  40                  45

Ala Ala Ile Arg Glu Ser Gly Ser Arg Thr Tyr Tyr Ala Asp Ser Val
    50                  55                  60

Arg Gly Arg Asp Thr Ile Ser Arg Asp Asn Lys Asn Ala Gly Asp
65                  70                  75                  80

Leu Gln Met Asn Ser Leu Lys Pro Glu Asp Ser Ala Thr Tyr Tyr Cys
                85                  90                  95
```

```
Ala Val Asp Gln Tyr Pro Thr Thr Glu Phe Ser Thr Gln Val Gly His
            100                 105                 110

Tyr Asp Tyr Trp Gly Gln Gly Thr Glu Val Thr Ile Ser Ser Gly Ser
        115                 120                 125

His His His His His His
    130

<210> SEQ ID NO 123
<211> LENGTH: 134
<212> TYPE: PRT
<213> ORGANISM: Artificial Sequence
<220> FEATURE:
<223> OTHER INFORMATION: Synthetic Construct

<400> SEQUENCE: 123

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Pro Arg His Tyr
            20                  25                  30

Ile Val Gly Trp Phe Arg Gln Ala Pro Gly Lys Glu Arg Glu Phe Val
        35                  40                  45

Ala Ala Val Arg Glu Ser Gly Ser Ser Thr Glu Tyr Ala Glu Asn Val
    50                  55                  60

Lys Gly Arg Phe Val Ile Ser Lys Asp Asn Val Lys Ser Thr Val Phe
65                  70                  75                  80

Leu Gln Met Asn Ser Leu Lys Pro Glu Asp Ser Ala Val Tyr Tyr Cys
                85                  90                  95

Ala Leu Asp Arg Phe Pro Thr Pro Glu Phe Ser Asp Arg Val Gly His
            100                 105                 110

Tyr Asp Leu Trp Gly Gln Gly Thr Gln Val Thr Val Ser Ser Gly Ser
        115                 120                 125

His His His His His His
    130

<210> SEQ ID NO 124
<211> LENGTH: 134
<212> TYPE: PRT
<213> ORGANISM: Artificial Sequence
<220> FEATURE:
<223> OTHER INFORMATION: Synthetic Construct

<400> SEQUENCE: 124

Gln Val Gln Leu Val Glu Ser Gly Gly Gly Leu Val Gln Ala Gly Gly
1               5                   10                  15

Ser Met Arg Leu Ser Cys Ala Ala Ser Gly Arg Thr Pro Arg His Tyr
            20                  25                  30

Ile Leu Gly Trp Phe Arg Gln Ala Pro Gly Lys Gln Arg Glu Phe Val
        35                  40                  45

Ala Ala Ile Arg Glu Ser Gly Ser Arg Thr Tyr Tyr Ala Asp Ser Val
    50                  55                  60

Arg Gly Arg Tyr Thr Ile Ser Arg Asp Asn Thr Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Gln Tyr Pro Thr Pro Glu Phe Ser Thr Gln Val Gly His
            100                 105                 110
```

Tyr Asp Tyr Trp Gly Gln Gly Thr Gln Val Thr Val Ser Ser Gly Ser
            115                 120                 125

His His His His His His
    130

<210> SEQ ID NO 125
<211> LENGTH: 134
<212> TYPE: PRT
<213> ORGANISM: Artificial Sequence
<220> FEATURE:
<223> OTHER INFORMATION: Synthetic Construct

<400> SEQUENCE: 125

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Pro Arg His Tyr
            20                  25                  30

Ile Leu Gly Trp Phe Arg Gln Ala Pro Gly Lys Leu Pro Glu Phe Val
        35                  40                  45

Ala Ala Val Arg Glu Pro Gly Ser Ser Thr Tyr Tyr Ala Asp Ser Val
    50                  55                  60

Lys Gly Arg Asp Thr Ile Ser Lys Asp His Thr Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Pro Tyr Pro Thr Pro Glu Phe Thr Thr His Val Gly His
            100                 105                 110

Tyr Asp Tyr Trp Gly Gln Gly Thr Gln Val Thr Val Ser Ser Gly Ser
            115                 120                 125

His His His His His His
    130

<210> SEQ ID NO 126
<211> LENGTH: 140
<212> TYPE: PRT
<213> ORGANISM: Artificial Sequence
<220> FEATURE:
<223> OTHER INFORMATION: Synthetic Construct

<400> SEQUENCE: 126

Gln Val Lys Leu Glu Glu Ser Gly Gly Gly Leu Val Gln Ala Gly Asp
1               5                   10                  15

Ser Leu Arg Leu Ser Cys Ala Ala Ser Gly Arg Ile Phe Asn His Tyr
            20                  25                  30

Val Thr Ser Trp Phe Arg Gln Ala Pro Asp Gln Glu Arg Glu Phe Val
        35                  40                  45

Ala Gly Val Thr Ala His Ala Gly Val Thr Ala Asp Val Glu Ser Thr
    50                  55                  60

Asp Tyr Ser Asp Ser Val Lys Gly Arg Phe Thr Val Ser Arg Asp Tyr
65                  70                  75                  80

Ser Lys Asn Thr Val Tyr Leu Gln Met Asn Ser Leu Lys Pro Glu Asp
                85                  90                  95

Thr Ala Val Tyr Tyr Cys Ala Ala Pro Ser Gly Phe Tyr Arg Thr Ile
            100                 105                 110

Pro His Val His Ser Asn Tyr Asp His Trp Gly Gln Gly Thr Gln Val
            115                 120                 125

Thr Val Ser Ser Gly Ser His His His His His
    130                 135                 140

```
<210> SEQ ID NO 127
<211> LENGTH: 140
<212> TYPE: PRT
<213> ORGANISM: Artificial Sequence
<220> FEATURE:
<223> OTHER INFORMATION: Synthetic Construct

<400> SEQUENCE: 127
```

Gln Val Lys Leu Glu Glu Ser Gly Gly Gly Leu Val Gln Ala Gly Gly
1               5                   10                  15

Ser Leu Arg Leu Ser Cys Val Ala Ser Gly Arg Thr Ile Asn Asp Tyr
            20                  25                  30

Ile Leu Gly Trp Phe Arg Gln Ala Pro Gly Lys Lys Arg Glu Phe Val
        35                  40                  45

Ala Ala Ile Arg Gly Ser Gly Ala Ile Arg Gly Arg Glu Gly Ser Thr
    50                  55                  60

Phe Tyr Val Asp Ser Val Lys Gly Arg Tyr Thr Ile Ser Lys Asp Asn
65                  70                  75                  80

Ala Lys Asn Thr Val Asp Leu Gln Met Asn Ser Leu Lys Pro Glu Asp
                85                  90                  95

Ser Ala Thr Tyr Tyr Cys Ala Val Asp Arg Phe Pro Thr Pro Glu Phe
            100                 105                 110

Ser Thr Gln Val Gly His Tyr Asp Tyr Trp Gly Gln Gly Thr Gln Val
        115                 120                 125

Thr Val Ser Ser Gly Ser His His His His His His
    130                 135                 140

```
<210> SEQ ID NO 128
<211> LENGTH: 140
<212> TYPE: PRT
<213> ORGANISM: Artificial Sequence
<220> FEATURE:
<223> OTHER INFORMATION: Synthetic Construct

<400> SEQUENCE: 128
```

Gln Val Gln Leu Val Glu Ser Gly Gly Gly Leu Val Gln Ala Gly Gly
1               5                   10                  15

Ser Leu Arg Leu Ser Cys Leu Ala Ser Asp Arg Thr Val Asn Asn Tyr
            20                  25                  30

Ile Val Gly Tyr Phe Arg Gln Ala Pro Gly Lys Glu Arg Glu Phe Val
        35                  40                  45

Ala Ala Ile Arg Gly Ser Gly Ala Ile Arg Gly Arg Glu Gly Ser Thr
    50                  55                  60

Tyr Tyr Ala Asp Ser Val Lys Gly Arg Phe Ser Ile Ser Lys Asp Asn
65                  70                  75                  80

Ala Lys Asn Thr Ile Tyr Leu Gln Met Asn Ser Leu Lys Pro Glu Asp
                85                  90                  95

Ser Ala Val Tyr Tyr Cys Ala Leu Asp Arg Phe Pro Thr Pro Glu Phe
            100                 105                 110

Thr Thr Gln Val Gly His Tyr Asp Val Trp Gly Arg Gly Thr Gln Val
        115                 120                 125

Thr Val Ser Ser Gly Ser His His His His His His
    130                 135                 140

```
<210> SEQ ID NO 129
<211> LENGTH: 134
<212> TYPE: PRT
<213> ORGANISM: Artificial Sequence
```

<220> FEATURE:
<223> OTHER INFORMATION: Synthetic Construct

<400> SEQUENCE: 129

Gln Val Lys Leu Glu Glu Ser Gly Gly Gly Leu Val Gln Ala Gly Gly
1               5                   10                  15

Ser Leu Arg Leu Ser Cys Val Ala Ser Gly Arg Thr Ile Asn Asp Tyr
            20                  25                  30

Ile Leu Gly Trp Phe Arg Gln Ala Pro Gly Lys Lys Arg Glu Phe Val
        35                  40                  45

Ala Ala Ile Arg Glu Ser Gly Ser Ser Thr Tyr Tyr Ala Asp Ser Val
    50                  55                  60

Lys Gly Arg Tyr Thr Ile Ser Arg Asn Asn Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Gln Tyr Pro Thr Pro Glu Phe Ser Thr Gln Val Gly His
            100                 105                 110

Tyr Asp Tyr Trp Gly Gln Gly Thr Gln Val Thr Val Ser Ser Gly Ser
        115                 120                 125

His His His His His His
    130

<210> SEQ ID NO 130
<211> LENGTH: 134
<212> TYPE: PRT
<213> ORGANISM: Artificial Sequence
<220> FEATURE:
<223> OTHER INFORMATION: Synthetic Construct

<400> SEQUENCE: 130

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Pro Arg His Tyr
            20                  25                  30

Ile Leu Gly Trp Phe Arg Gln Ala Pro Gly Lys Gln Arg Glu Phe Val
        35                  40                  45

Ala Ala Ile Arg Glu Ser Gly Ser Ser Thr Tyr Tyr Ala Asp Ser Val
    50                  55                  60

Lys Gly Arg Tyr Thr Ile Ser Arg Asp Asn Thr Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Gln Tyr Pro Thr Pro Glu Phe Ser Thr Gln Val Gly His
            100                 105                 110

Tyr Asp Tyr Trp Gly Gln Gly Thr Gln Val Thr Val Ser Ser Gly Ser
        115                 120                 125

His His His His His His
    130

<210> SEQ ID NO 131
<211> LENGTH: 135
<212> TYPE: PRT
<213> ORGANISM: Artificial Sequence
<220> FEATURE:
<223> OTHER INFORMATION: Synthetic Construct

<400> SEQUENCE: 131

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Val Tyr
            20                  25                  30

Ala Met Gly Trp Phe Arg Gln Ala Pro Gly Lys Glu Arg Glu Phe Val
        35                  40                  45

Ala Ala Ile Thr Ser Pro Gly Asp Ser Ile Pro Tyr Ala His Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Ala Tyr Tyr Cys
                85                  90                  95

Ala Ala Thr Lys Ser Gly Asn Tyr Asn Tyr Met Gly Pro Asp Pro Lys
            100                 105                 110

Lys Tyr His Tyr Trp Gly Gln Gly Thr Gln Val Thr Val Ser Ser Gly
        115                 120                 125

Ser His His His His His
    130                 135
```

<210> SEQ ID NO 132
<211> LENGTH: 135
<212> TYPE: PRT
<213> ORGANISM: Artificial Sequence
<220> FEATURE:
<223> OTHER INFORMATION: Synthetic Construct

<400> SEQUENCE: 132

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Val Tyr
            20                  25                  30

Ala Met Gly Trp Phe Arg Gln Ala Pro Gly Lys Glu Arg Glu Phe Val
        35                  40                  45

Thr Ala Ile Thr Ser Ser Gly Asp Ser Ile Pro Tyr Ala His Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ala Tyr Tyr Cys
                85                  90                  95

Ala Ala Thr Thr Ser Gly Thr Tyr Asn Tyr Met Gly Pro Asp Pro Lys
            100                 105                 110

Glu Tyr Val Tyr Trp Gly Gln Gly Thr Gln Val Thr Val Ser Ser Gly
        115                 120                 125

Ser His His His His His
    130                 135
```

<210> SEQ ID NO 133
<211> LENGTH: 146
<212> TYPE: PRT
<213> ORGANISM: Artificial Sequence
<220> FEATURE:
<223> OTHER INFORMATION: Synthetic Construct -continued

<400> SEQUENCE: 133

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn Asp Tyr
            20                  25                  30

Ala Met Gly Trp Phe Arg Gln Ala Pro Gly Lys Glu Arg Glu Phe Val
        35                  40                  45

Ala Ala Ala Ala Gln Ser Gly Asp Ser Ser Ala Tyr Ala Arg Ser Val
    50                  55                  60

Lys Gly Arg Phe Thr Ile Ser Arg Asp Gly Ala Lys Asn Thr Ala Tyr
65                  70                  75                  80

Leu Gln Met Asp Ser Leu Lys Pro Glu Asp Thr Ala Ala Tyr Tyr Cys
                85                  90                  95

Ala Ala Thr Thr Arg Gly Ser Tyr Glu Tyr Met Gly Pro Asp Pro Lys
            100                 105                 110

Lys Tyr Glu Tyr Trp Gly Gln Gly Thr Gln Val Thr Val Ser Ser Gly
        115                 120                 125

Ser Glu Gln Lys Leu Ile Ser Glu Glu Asp Leu Asn His His His His
    130                 135                 140

His His
145

<210> SEQ ID NO 134
<211> LENGTH: 142
<212> TYPE: PRT
<213> ORGANISM: Artificial Sequence
<220> FEATURE:
<223> OTHER INFORMATION: Synthetic Construct

<400> SEQUENCE: 134

Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Phe Ser Asn Tyr
            20                  25                  30

Ala Met Gly Trp Phe Arg Gln Ala Pro Gly Thr Glu Arg Glu Phe Val
        35                  40                  45

Gly Gln Ile Ser Gln Val Asp Gly Phe Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Ala Leu Ala Phe Pro Thr Thr Ser Ser Asn Thr Tyr Ala Tyr
            100                 105                 110

Ser Gly Gln Gly Thr Gln Val Thr Val Ser Ser Gly Ser Glu Gln Lys
        115                 120                 125

Leu Ile Ser Glu Glu Asp Leu Asn His His His His His His
    130                 135                 140

<210> SEQ ID NO 135
<211> LENGTH: 135
<212> TYPE: PRT
<213> ORGANISM: Artificial Sequence
<220> FEATURE:
<223> OTHER INFORMATION: Synthetic Construct

<400> SEQUENCE: 135

```
Gln Val Lys Leu Glu Glu Ser Gly Gly Gly Leu Val Gln Ala Gly Gly
1               5                   10                  15

Ser Leu Arg Leu Ser Cys Ser Pro Ser Asp Arg Thr Phe Ser Ala Tyr
            20                  25                  30

Ala Met Gly Trp Phe Arg Gln Val Pro Gly Arg Glu Arg Glu Phe Val
        35                  40                  45

Ala Thr Ile Arg Asp Ser Asp Ala Ser Ile Tyr Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Ile Pro Asp Asp Thr Ala Val Tyr Tyr Cys
                85                  90                  95

Ala Ala Arg Gln Tyr Tyr Ser Gly Arg Val Tyr Ser Thr Phe Arg Glu
            100                 105                 110

Glu Tyr Asp Tyr Trp Gly Gln Gly Thr Gln Val Thr Val Ser Ser Gly
        115                 120                 125

Ser His His His His His His
    130                 135
```

<210> SEQ ID NO 136
<211> LENGTH: 129
<212> TYPE: PRT
<213> ORGANISM: Artificial Sequence
<220> FEATURE:
<223> OTHER INFORMATION: Synthetic Construct

<400> SEQUENCE: 136

```
Gln Val Lys Leu Glu Glu Ser Gly Gly Gly Leu Val Gln Ala Gly Gly
1               5                   10                  15

Ser Leu Arg Leu Ser Cys Ala Ala Pro Arg Ser Gly Val Val Ile Ala
            20                  25                  30

Tyr Met Ala Trp Tyr Arg Gln Ala Pro Glu Lys Gln Arg Glu Leu Val
        35                  40                  45

Ala Ser Ile Ser Ser Gly Gly Thr Thr Asn Tyr Ala Val Phe Ala Lys
    50                  55                  60

Gly Arg Phe Thr Ile Ser Ala Asp Asn Ala Lys Asn Thr Val Tyr Leu
65                  70                  75                  80

Gln Met Asn Ser Leu Lys Pro Glu Asp Thr Ala Val Tyr Ile Cys Asn
                85                  90                  95

Ala Tyr Ala Met Ser Thr Glu Thr Met Val Ser Gln Asp Tyr Trp Gly
            100                 105                 110

Gln Gly Thr Gln Val Thr Val Ser Ser Gly Ser His His His His His
        115                 120                 125

His
```

<210> SEQ ID NO 137
<211> LENGTH: 146
<212> TYPE: PRT
<213> ORGANISM: Artificial Sequence
<220> FEATURE:
<223> OTHER INFORMATION: Synthetic Construct -continued

<400> SEQUENCE: 137

Gln Val Lys Leu Glu Glu Ser Gly Gly Gly Leu Val Gln Ala Gly Gly
1               5                   10                  15

Ser Leu Arg Leu Ser Cys Ala Ala Ser Gly Leu Thr Phe Ser Asn Tyr
            20                  25                  30

Ala Met Gly Trp Phe Arg Gln Ala Pro Gly Ala Glu Arg Glu Phe Val
        35                  40                  45

Gly Gln Ile Ser Gln Val Asp Gly Phe Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Asp Asp Thr Ala Val Tyr Tyr Cys
                85                  90                  95

Ala Ala Thr Tyr Ser Gly Thr Tyr Asn Tyr Met Gly Ala Asp Pro Lys
            100                 105                 110

Glu Tyr Val Tyr Trp Gly Gln Gly Thr Gln Val Thr Val Ser Ser Gly
        115                 120                 125

Ser Glu Gln Lys Leu Ile Ser Glu Glu Asp Leu Asn His His His His
    130                 135                 140

His His
145

<210> SEQ ID NO 138
<211> LENGTH: 132
<212> TYPE: PRT
<213> ORGANISM: Artificial Sequence
<220> FEATURE:
<223> OTHER INFORMATION: Synthetic Construct

<400> SEQUENCE: 138

Gln Val Lys Leu Glu Glu Ser Gly Gly Gly Pro Val Gln Ala Gly Gly
1               5                   10                  15

Ser Leu Arg Leu Ser Cys Leu Ala Ser Gly Arg Phe Val Asn Ser Pro
            20                  25                  30

Thr Met Ala Trp Phe Arg Gln Ala Pro Gly Glu Glu Arg Lys Phe Val
        35                  40                  45

Ala Ala Ile Arg Ser Arg Asp Asp Ser Thr Tyr Tyr Ser Asn Ser Val
    50                  55                  60

Lys Gly Arg Phe Thr Ile Ser Leu Asp Asn Ala Lys Asn Thr Ala Tyr
65                  70                  75                  80

Leu Arg Met Asp Ser Leu Gln Pro Glu Asp Thr Ala Val Tyr Tyr Cys
                85                  90                  95

Ala Gly Asp Pro Arg Thr Ile Asp Leu Ser Ser Arg Leu Leu Trp Gly
            100                 105                 110

Ser Trp Gly Gln Gly Thr Gln Val Thr Val Ser Ser Gly Ser His His
        115                 120                 125

His His His His
    130

<210> SEQ ID NO 139
<211> LENGTH: 134
<212> TYPE: PRT
<213> ORGANISM: Artificial Sequence
<220> FEATURE:
<223> OTHER INFORMATION: Synthetic Construct

<400> SEQUENCE: 139

Gln Val Gln Leu Val Glu Ser Gly Gly Gly Leu Val Gln Ala Gly Gly
1               5                   10                  15

Ser Met Arg Leu Ser Cys Ala Ala Ser Gly Arg Thr Pro Arg His Tyr
            20                  25                  30

Ile Leu Gly Trp Phe Arg Gln Ala Pro Gly Lys Gln Arg Glu Phe Val
        35                  40                  45

Ala Ala Ile Arg Glu Ser Gly Ser Arg Thr Tyr Tyr Ala Asp Ser Val
    50                  55                  60

Arg Gly Arg Asp Thr Ile Ser Arg Asp Asn Lys Asn Ala Gly Asp
65                  70                  75                  80

Leu Gln Met Asn Ser Leu Lys Pro Glu Asp Ser Ala Thr Tyr Tyr Cys
                85                  90                  95

Ala Val Asp Gln Tyr Pro Thr Thr Glu Phe Ser Thr Gln Val Gly His
            100                 105                 110

Tyr Asp Tyr Trp Gly Gln Gly Thr Glu Val Thr Ile Ser Ser Gly Ser
        115                 120                 125

His His His His His His
    130

<210> SEQ ID NO 140
<211> LENGTH: 134
<212> TYPE: PRT
<213> ORGANISM: Artificial Sequence
<220> FEATURE:
<223> OTHER INFORMATION: Synthetic Construct

<400> SEQUENCE: 140

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Pro Arg His Tyr
            20                  25                  30

Ile Val Gly Trp Phe Arg Gln Ala Pro Gly Lys Glu Arg Glu Phe Val
        35                  40                  45

Ala Ala Val Arg Glu Ser Gly Ser Ser Thr Glu Tyr Ala Glu Asn Val
    50                  55                  60

Lys Gly Arg Phe Val Ile Ser Lys Asp Asn Val Lys Ser Thr Val Phe
65                  70                  75                  80

Leu Gln Met Asn Ser Leu Lys Pro Glu Asp Ser Ala Val Tyr Tyr Cys
                85                  90                  95

Ala Leu Asp Arg Phe Pro Thr Pro Glu Phe Ser Asp Arg Val Gly His
            100                 105                 110

Tyr Asp Leu Trp Gly Gln Gly Thr Gln Val Thr Val Ser Ser Gly Ser
        115                 120                 125

His His His His His His
    130

<210> SEQ ID NO 141
<211> LENGTH: 134
<212> TYPE: PRT
<213> ORGANISM: Artificial Sequence
<220> FEATURE:
<223> OTHER INFORMATION: Synthetic Construct -continued

<400> SEQUENCE: 141

```
Gln Val Gln Leu Val Glu Ser Gly Gly Gly Leu Val Gln Ala Gly Gly
1               5                   10                  15

Ser Met Arg Leu Ser Cys Ala Ala Ser Gly Arg Thr Pro Arg His Tyr
            20                  25                  30

Ile Leu Gly Trp Phe Arg Gln Ala Pro Gly Lys Gln Arg Glu Phe Val
        35                  40                  45

Ala Ala Ile Arg Glu Ser Gly Ser Arg Thr Tyr Tyr Ala Asp Ser Val
    50                  55                  60

Arg Gly Arg Tyr Thr Ile Ser Arg Asp Asn Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Gln Tyr Pro Thr Pro Glu Phe Ser Thr Gln Val Gly His
            100                 105                 110

Tyr Asp Tyr Trp Gly Gln Gly Thr Gln Val Thr Val Ser Ser Gly Ser
        115                 120                 125

His His His His His His
    130
```

<210> SEQ ID NO 142
<211> LENGTH: 134
<212> TYPE: PRT
<213> ORGANISM: Artificial Sequence
<220> FEATURE:
<223> OTHER INFORMATION: Synthetic Construct

<400> SEQUENCE: 142

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Pro Arg His Tyr
            20                  25                  30

Ile Leu Gly Trp Phe Arg Gln Ala Pro Gly Lys Leu Pro Glu Phe Val
        35                  40                  45

Ala Ala Val Arg Glu Pro Gly Ser Ser Thr Tyr Tyr Ala Asp Ser Val
    50                  55                  60

Lys Gly Arg Asp Thr Ile Ser Lys Asp His Thr Lys Asn Ala Val Asp
65                  70                  75                  80

Leu Gln Met Asn Ser Leu Lys Pro Glu Asp Ser Ala Thr Tyr Tyr Cys
                85                  90                  95

Ala Val Asp Pro Tyr Pro Thr Pro Glu Phe Thr Thr His Val Gly His
            100                 105                 110

Tyr Asp Tyr Trp Gly Gln Gly Thr Gln Val Thr Val Ser Ser Gly Ser
        115                 120                 125

His His His His His His
    130
```

<210> SEQ ID NO 143
<211> LENGTH: 140
<212> TYPE: PRT
<213> ORGANISM: Artificial Sequence
<220> FEATURE:
<223> OTHER INFORMATION: Synthetic Construct

<400> SEQUENCE: 143

Gln Val Lys Leu Glu Glu Ser Gly Gly Gly Leu Val Gln Ala Gly Asp
1               5                   10                  15

Ser Leu Arg Leu Ser Cys Ala Ala Ser Gly Arg Ile Phe Asn His Tyr
            20                  25                  30

Val Thr Ser Trp Phe Arg Gln Ala Pro Asp Gln Arg Glu Phe Val
        35                  40                  45

Ala Gly Val Thr Ala His Ala Gly Val Thr Ala Asp Val Glu Ser Thr
    50                  55                  60

Asp Tyr Ser Asp Ser Val Lys Gly Arg Phe Thr Val Ser Arg Asp Tyr
65              70                  75                  80

Ser Lys Asn Thr Val Tyr Leu Gln Met Asn Ser Leu Lys Pro Glu Asp
                85                  90                  95

Thr Ala Val Tyr Tyr Cys Ala Ala Pro Ser Gly Phe Tyr Arg Thr Ile
            100                 105                 110

Pro His Val His Ser Asn Tyr Asp His Trp Gly Gln Gly Thr Gln Val
        115                 120                 125

Thr Val Ser Ser Gly Ser His His His His His
    130                 135                 140

<210> SEQ ID NO 144
<211> LENGTH: 45
<212> TYPE: DNA
<213> ORGANISM: Artificial Sequence
<220> FEATURE:
<223> OTHER INFORMATION: Synthetic Construct

<400> SEQUENCE: 144
gcccagccgg ccatggccsm kgtgcagctg gtggaktctg gggga          45

<210> SEQ ID NO 145
<211> LENGTH: 42
<212> TYPE: DNA
<213> ORGANISM: Artificial Sequence
<220> FEATURE:
<223> OTHER INFORMATION: Synthetic Construct

<400> SEQUENCE: 145
cagccggcca tggcccaggt aaagctggag gagtctgggg ga             42

<210> SEQ ID NO 146
<211> LENGTH: 45
<212> TYPE: DNA
<213> ORGANISM: Artificial Sequence
<220> FEATURE:
<223> OTHER INFORMATION: Synthetic Construct

<400> SEQUENCE: 146
gcccagccgg ccatggccca ggctcaggta cagctggtgg agtct          45

<210> SEQ ID NO 147
<211> LENGTH: 21
<212> TYPE: DNA
<213> ORGANISM: Artificial Sequence
<220> FEATURE:
<223> OTHER INFORMATION: Synthetic Construct

<400> SEQUENCE: 147
cgccatcaag gtaccagttg a                                    21

```
<210> SEQ ID NO 148
<211> LENGTH: 29
<212> TYPE: DNA
<213> ORGANISM: Artificial Sequence
<220> FEATURE:
<223> OTHER INFORMATION: Synthetic Construct

<400> SEQUENCE: 148
ggggtacctg tcatccacgg accagctga                                              29

<210> SEQ ID NO 149
<211> LENGTH: 34
<212> TYPE: DNA
<213> ORGANISM: Artificial Sequence
<220> FEATURE:
<223> OTHER INFORMATION: Synthetic Construct

<400> SEQUENCE: 149
catgtgtaga ctcgcggccc agccggccat ggcc                                        34

<210> SEQ ID NO 150
<211> LENGTH: 47
<212> TYPE: DNA
<213> ORGANISM: Artificial Sequence
<220> FEATURE:
<223> OTHER INFORMATION: Synthetic Construct

<400> SEQUENCE: 150
catgtgtaga ttcctggccg gcctggcctg aggagacggt gacctgg                          47
```